US011638749B2

(12) United States Patent
Laddy et al.

(10) Patent No.: US 11,638,749 B2
(45) Date of Patent: May 2, 2023

(54) TUBERCULOSIS ANTIGEN CASSETTES

(71) Applicant: International AIDS Vaccine Initiative, Inc., New York, NY (US)

(72) Inventors: Dominick Laddy, New York, NY (US); Danilo Casimiro, New York, NY (US); Thomas Evans, New York, NY (US); Megan Fitzpatrick Forrest, New York, NY (US); Nathalie Cadieux, New York, NY (US)

(73) Assignee: International AIDS Vaccine Initiative, Inc., New York, NY (US)

( * ) Notice: Subject to any disclaimer, the term of this patent is extended or adjusted under 35 U.S.C. 154(b) by 0 days.

(21) Appl. No.: 16/756,206

(22) PCT Filed: Oct. 15, 2018

(86) PCT No.: PCT/US2018/055817
§ 371 (c)(1),
(2) Date: Apr. 15, 2020

(87) PCT Pub. No.: WO2019/079155
PCT Pub. Date: Apr. 25, 2019

(65) Prior Publication Data
US 2020/0282038 A1    Sep. 10, 2020

Related U.S. Application Data

(60) Provisional application No. 62/573,432, filed on Oct. 17, 2017.

(51) Int. Cl.
*A61K 39/04* (2006.01)
*C07K 14/35* (2006.01)

(52) U.S. Cl.
CPC .............. *A61K 39/04* (2013.01); *C07K 14/35* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 5,334,498 A | 8/1994 | Roizman et al. |
| 5,593,873 A | 1/1997 | Cochran et al. |
| 5,593,972 A | 1/1997 | Weiner et al. |
| 5,599,544 A | 2/1997 | Cochran et al. |
| 5,676,952 A | 10/1997 | Audonnet et al. |
| 5,720,957 A | 2/1998 | Jones et al. |
| 5,731,188 A | 3/1998 | Cochran et al. |
| 5,741,696 A | 4/1998 | Cochran et al. |
| 5,753,476 A | 5/1998 | Jones et al. |
| 5,804,372 A | 9/1998 | Cochran et al. |
| 5,837,532 A | 11/1998 | Preston et al. |
| 5,843,458 A | 12/1998 | Jones |
| 5,846,806 A | 12/1998 | Jones et al. |
| 5,853,733 A | 12/1998 | Cochran et al. |
| 5,874,279 A | 2/1999 | Cochran et al. |
| 5,906,935 A | 5/1999 | Jones et al. |
| 5,908,780 A | 6/1999 | Jones |
| 5,962,428 A | 10/1999 | Carrano |
| 6,033,671 A | 3/2000 | Frueh et al. |
| 6,103,531 A | 8/2000 | Sedmak et al. |
| 6,140,114 A | 10/2000 | Klatzman et al. |
| 6,410,033 B1 | 6/2002 | Cochran |
| 6,613,892 B2 | 9/2003 | Preston et al. |
| 6,740,324 B2 | 5/2004 | Schall et al. |
| 6,913,751 B2 | 7/2005 | Cochran et al. |
| 6,953,661 B1 | 10/2005 | Diefenbach et al. |
| 7,364,893 B2 | 4/2008 | Wild et al. |
| 7,749,745 B2 | 7/2010 | Johnson et al. |
| 7,892,564 B2 | 2/2011 | Wild et al. |
| 8,486,414 B2* | 7/2013 | Reed ............... G01N 33/5695 424/192.1 |
| 9,249,427 B2 | 2/2016 | Picker et al. |
| 2009/0304750 A1 | 12/2009 | Hone et al. |
| 2011/0117133 A1 | 5/2011 | Shafferman et al. |
| 2013/0136768 A1 | 5/2013 | Picker et al. |
| 2013/0209500 A1 | 8/2013 | Reed et al. |
| 2014/0004151 A1 | 1/2014 | Sette et al. |
| 2014/0141038 A1 | 5/2014 | Picker et al. |
| 2014/0377300 A1 | 12/2014 | Ravi et al. |
| 2015/0165014 A1 | 6/2015 | Tupin et al. |
| 2016/0228528 A1 | 8/2016 | Jungersen et al. |
| 2016/0331823 A1 | 11/2016 | Marchand et al. |

(Continued)

FOREIGN PATENT DOCUMENTS

| | | |
|---|---|---|
| WO | 94016737 | 8/1994 |
| WO | 2007058663 | 5/2007 |
| WO | 2008124647 | 10/2008 |

(Continued)

OTHER PUBLICATIONS

Angulo et al., "The Major Immediate-Early Gene ie3 of Mouse Cytomegalovirus Is Essential for Viral Growth", J. Virol., 2000, 74, 11129-11136.
Asanuma, H., et al., "Frequencies of memory T cells specific for varicella-zoster virus, herpes simplex virus, and cytomegalovirus by intracellular detection of cytokine expression", J Infect Dis, 2000, 181, p. 859-866.
Barnes et al., "Harnessing Endogenous miRNAs to Control Virus Tissue Tropism as a Strategy for Developing Attenuated Virus VaccinesCell Host Microbe", 2008, 4, 239-248.
Brown et al., "Endogenous microRNA can be broadly exploited to regulate transgene expression according to tissue, lineage and differentiation state", Nat. Biotechnol., 2007, 25, 1457-1467.
Dankner, W. M., et al., "Localization of human cytomegalovirus in peripheral blood leukocytes by in situ hybridization", J Infect Dis, 1990, 161, p. 31-36.

(Continued)

*Primary Examiner* — Brian Gangle
(74) *Attorney, Agent, or Firm* — Armstrong Teasdale LLP

(57) ABSTRACT

The present disclosure provides fusion proteins comprising *Mycobacterium tuberculosis* (Mtb) antigens, nucleic acid molecules encoding the same, vectors comprising nucleic acid molecules, compositions comprising the same, and methods of eliciting an immune response against tuberculosis.

6 Claims, No Drawings

Specification includes a Sequence Listing.

(56) References Cited

U.S. PATENT DOCUMENTS

| | | |
|---|---|---|
| 2017/0043003 A1 | 2/2017 | Aagaard et al. |
| 2017/0362284 A1 | 12/2017 | Anantha et al. |

FOREIGN PATENT DOCUMENTS

| | | |
|---|---|---|
| WO | 2014009438 | 1/2014 |
| WO | 2014063704 | 5/2014 |
| WO | 2014140301 | 9/2014 |
| WO | 2014210018 | 12/2014 |
| WO | 20170087921 | 5/2017 |
| WO | 2017218867 | 12/2017 |

OTHER PUBLICATIONS

Einhorn, L., et al., "Cytomegalovirus infection of human blood cells", J Infect Dis, 1984, 149, p. 207-214.

Gerna, G., et al., "Dendritic-cell infection by human cytomegalovirus is restricted to strains carrying functional UL131-128 genes and mediates efficient viral antigen presentation to CD8+ T cells", J Gen Virol, 2005, 86, p. 275-284.

Gnann, J. W. Jr., et al., "Inflammatory cells in transplanted kidneys are infected by human cytomegalovirus", Am J Pathol, 1988, 132, p. 239-248.

Hahn, G., et al., "Human cytomegalovirus UL131-128 genes are indispensable for virus growth in endothelial cells and virus transfer to leukocytes", J Virol, 2004, 78, p. 10023-10033.

Hansen et al., "Effector memory T cell responses are associated with protection of rhesus monkeys from mucosal simian immunodeficiency virus challenge", Nat. Med., 2009, 15, 293-299.

Hansen, S. G., et al., "Evasion of CD8+ T cells is critical for superinfection by cytomegalovirus", Science, 2010, 328, p. 102-106.

Hansen et al., "Profound early control of highly pathogenic SIV by an effector memory T-cell vaccine", Nature, 2011, 473, 523-527.

Hansen et al., "Immune clearance of highly pathogenic SIV infection", Nature, 2013, 502, 100-104.

Hansen et al., "Cytomegalovirus Vectors Violate CD8+ T Cell Epitope Recognition Paradigms", Science, 2013, 340, 1237874.

Hansen et al., "Broadly targeted CD8+ T cell responses restricted by major histocompatibility complex E", Science, 2016, 351, 714-720.

Harari, A., et al., "Functional heterogeneity of memory CD4+ T cell responses in different conditions of antigen exposure and persistence", J Immunol, 2005, 174, p. 1037-1045.

Harari, A., et al., "Distinct profiles of cytotoxic granules in memory CD8+ T cells correlate with function, differentiation stage, and antigen exposure", J Virol, 2009, 83, p. 2862-2871.

Howell, C. L., et al., "Comparison of rates of virus isolation from leukocyte populations separated from blood by conventional and Ficoll-Paque/Macrodex methods", J Clin Microbiol, 1979, 10, p. 533-537.

Jarvis, M. A., et al., "Mechanisms of human cytomegalovirus persistence and latency", Front Biosci., 2002, 7, d1575-1582.

Lee et al., "MicroRNA Regulation of Oncolytic Herpes Simplex Virus-1 for Selective Killing of Prostate Cancer Cells", Clin. Cancer Res., 2009, 15, 5126-5135.

Lilja, et al., "Efficient replication of rhesus cytomegalovirus variants in multiple rhesus and human cell types", Proc Natl Acad Sci USA, 2008, 105, p. 19950-19955.

Lilja, A. E., et al., "Functional genetic analysis of rhesus cytomegalovirus: Rh-1 is an epithelial cell tropism factor", J Virol, 2008, 82, p. 2170-2181.

Myerson, D., et al., "Widespread presence of histologically occult cytomegalovirus", Hum Pathol, 1984, 15, p. 430-439.

Perez et al., "MicroRNA-mediated species-specific attenuation of influenza A virus", Nat. Biotechnol., 2009, 27, 572-576.

Rue, C. A., et al., "A cyclooxygenase-2 homologue encoded by rhesus cytomegalovirus is a determinant for endothelial cell tropism", Journal of Virology, 2004, 78, p. 12529-12536.

Ryckman, B. J., et al., "Human cytomegalovirus entry into epithelial and endothelial cells depends on genes UL128 to UL150 and occurs by endocytosis and low-pH fusion", J Virol, 2006, 80, p. 710-722.

Ryckman, B. J., et al., "Characterization of the human cytomegalovirus gH/gL/UL128-131 complex that mediates entry into epithelial and endothelial cells", J Virol, 2008, 82, p. 60-70.

Schrier, R. D., et al., "Detection of human cytomegalovirus in peripheral blood lymphocytes in a natural infection", Science, 1985, 230, p. 1048-1051.

Sinzger, C., et al., "Fibroblasts, epithelial cells, endothelial cells and smooth muscle cells are major targets of human cytomegalovirus infection in lung and gastrointestinal tissues", J Gen Virol, 1995, 76, p. 741-750.

Snyder et al., "Cross-presentation of a spread-defective MCMV is sufficient to prime the majority of virus-specific CD8+ T cells", PLoS One, 2010, 5:e9681, doi:10.1371/journal.pone.0009681.

Sylwester, A. W., et al., "Broadly targeted human cytomegalovirus-specific CD4+ and CD8+ T cells dominate the memory compartments of exposed subjects", J Exp Med, 2005, 202, p. 673-685.

Wang, D., et al., "Human cytomegalovirus UL131 open reading frame is required for epithelial cell tropism", J Virol, 2005, 79, p. 10330-10338.

Wang, D., et al., "Human cytomegalovirus virion protein complex required for epithelial and endothelial cell tropism", Proc Natl Acad Sci USA, 2005, 102, p. 18153-18158.

Singh et al., "*Mycobacterium tuberculosis* controls microRNA-99b (miR-99b) expression in infected murine dendritic cells to modulate host immunity", J Biol Chem, 2012, 288(7), pp. 5056-5061.

McGregor et al., "Expression of the human cytomegalovirus UL97 gene in a chimeric guinea pig cytomegalovirus (GPCMV) results in viable virus with increased susceptibility to ganciclovir and maribavir", Antiviral Res, 2008, 78(3), pp. 250-259.

Hoft et al., "Safety and Immunogenicity of the Recombinant BCG Vaccine AERAS-422 in Healthy BCG-naive Adults: A Randomized, Active-controlled, First-in-human Phase 1 Trail", EBioMedicine, 2016, 7, pp. 278-286.

Velmurugan et al., "Nonclinical Development of BCG Replacement Vaccine Candidates", Vaccines, 2013, 1(2), pp. 120-138.

Graves et al., "Tuberculosis Vaccines: Review of Current Development Trends and Future Challenges", J Bioterr Biodef, 2011, S1-009.

da Costa et al., "Tuberculosis vaccines-state of the art, and novel approaches to vaccine development", Int J Infect Dis, 2015, 32, pp. 5-12.

Zvi et al., "Whole genome identification of *Mycobacterium tuberculosis* vaccine candidates by comprehensive data mining and bioinformatic analyses", BMC Med Genomics, 2008, 1(18), pp. 1-25.

De Sousa et al., "Immunogenicity of a Fusion Protein Containing Immunodominant Epitopes of Ag85C, MPT51, and HspX from *Mycobacterium tuberculosis* in Mice and Active TB Infection", Plos ONE, 2012, 7(10), e47781.

Langermans et al., "Protection of macaques against *Mycobacterium tuberculosis* infection by a subunit vaccine based on a fusion protein of antigen 85B and ESAT-6", Vaccine, 2005, 23, pp. 2740-2750.

Luo et al., "Fusion Protein Ag85B-MPT64(190-198)-Mtb8.4 Has Higher Immunogenicity Than Ag85B With Capacity to Boost BCG-primed Immunity Against *Mycobacterium tuberculosis* in Mice", Vaccine, 2009, 27, pp. 6179-6185.

Non-Final Office Action dated Feb. 28, 2018 for U.S. Appl. No. 15/628,921.

Final Office Action dated Jan. 25, 2019 for U.S. Appl. No. 15/628,921.

Non-Final Office Action dated Aug. 20, 2019 for U.S. Appl. No. 15/628,921.

Non-Final Office Action dated May 14, 2020 for U.S. Appl. No. 15/628,921.

Leung-Theung-Long et al., "A Novel MVA-Based Multiphasic Vaccine for Prevention or Treatment of Tuberculosis Induces Broad and Multifunctional Cell-Mediated Immunity in Mice and Primates", PLoS One, 2015, 10(11), e0143552.

Leung-Theung-Long, "MVA Technology in the Development of Highly Complexed TB Vaccine Candidates", TBVI Symposium, Les Diablerets, Feb. 3, 2016.

(56) References Cited

OTHER PUBLICATIONS

Final Office Action dated Dec. 4, 2020 for U.S. Appl. No. 15/628,921.
Notice of Allowance dated Apr. 2, 2021 in related U.S. Appl. No. 15/628,921.
Brennan, "The Enigmatic PE/PPE Multigene Family of Mycobacteria and Tuberculosis Vaccination", Infection and Immunity, 2017, 85(6), pp. 1-8.
Non-Final Office Action dated Sep. 12, 2022 in related U.S. Appl. No. 17/365,509.

* cited by examiner

SEQUENCE LISTING

<160> NUMBER OF SEQ ID NOS: 71

<210> SEQ ID NO 1
<211> LENGTH: 300
<212> TYPE: DNA
<213> ORGANISM: artificial sequence
<220> FEATURE:
<223> OTHER INFORMATION: Rv3872 (PE35)

<400> SEQUENCE: 1

```
atggagaaga tgagccacga ccccatcgcc gccgacatcg gcacccaggt gagcgacaac      60
gccctgcacg gcgtgaccgc cggcagcacc gccctgacca gcgtgaccgg cctggtgccc     120
gccggcgccg acgaggtgag cgcccaggcc gccaccgcct tcaccagcga gggcatccag     180
ctgctggcca gcaacgccag cgcccaggac cagctgcaca gggccggcga ggccgtgcag     240
gacgtggcca ggacctacag ccagatcgac gacggcgccg ccggcgtgtt cgccgagtga     300
```

<210> SEQ ID NO 2
<211> LENGTH: 99
<212> TYPE: PRT
<213> ORGANISM: artificial sequence
<220> FEATURE:
<223> OTHER INFORMATION: Rv3872 (PE35)

<400> SEQUENCE: 2

```
Met Glu Lys Met Ser His Asp Pro Ile Ala Ala Asp Ile Gly Thr Gln
1               5                   10                  15

Val Ser Asp Asn Ala Leu His Gly Val Thr Ala Gly Ser Thr Ala Leu
            20                  25                  30

Thr Ser Val Thr Gly Leu Val Pro Ala Gly Ala Asp Glu Val Ser Ala
        35                  40                  45

Gln Ala Ala Thr Ala Phe Thr Ser Glu Gly Ile Gln Leu Leu Ala Ser
    50                  55                  60

Asn Ala Ser Ala Gln Asp Gln Leu His Arg Ala Gly Glu Ala Val Gln
65                  70                  75                  80

Asp Val Ala Arg Thr Tyr Ser Gln Ile Asp Asp Gly Ala Ala Gly Val
                85                  90                  95

Phe Ala Glu
```

<210> SEQ ID NO 3
<211> LENGTH: 300
<212> TYPE: DNA
<213> ORGANISM: artificial sequence
<220> FEATURE:
<223> OTHER INFORMATION: Rv1788 (PE18)

<400> SEQUENCE: 3

```
atgagcttcg tgaccaccca gcccgaggcc ctggccgccg ccgccggcag cctgcagggc      60
atcggcagcg ccctgaacgc ccagaacgcc gccgccgcca ccccaccac cggcgtggtg     120 cccgccgccg ccgacgaggt gagcgccctg accgccgccc agttcgccgc ccacgcccag     180
atctaccagg ccgtgagcgc ccaggccgcc gccatccacg agatgttcgt gaacaccctg     240
cagatgagca gcggcagcta cgccgccacc gaggccgcca cgccgccgc cgccggctga     300
```

<210> SEQ ID NO 4
<211> LENGTH: 99
<212> TYPE: PRT
<213> ORGANISM: artificial sequence
<220> FEATURE:
<223> OTHER INFORMATION: Rv1788 (PE18)

<400> SEQUENCE: 4

Met Ser Phe Val Thr Thr Gln Pro Glu Ala Leu Ala Ala Ala Ala Gly
1               5                   10                  15

Ser Leu Gln Gly Ile Gly Ser Ala Leu Asn Ala Gln Asn Ala Ala Ala
            20                  25                  30

Ala Thr Pro Thr Thr Gly Val Val Pro Ala Ala Ala Asp Glu Val Ser
        35                  40                  45

Ala Leu Thr Ala Ala Gln Phe Ala Ala His Ala Gln Ile Tyr Gln Ala
    50                  55                  60

Val Ser Ala Gln Ala Ala Ala Ile His Glu Met Phe Val Asn Thr Leu
65                  70                  75                  80

Gln Met Ser Ser Gly Ser Tyr Ala Ala Thr Glu Ala Ala Asn Ala Ala
                85                  90                  95

Ala Ala Gly

<210> SEQ ID NO 5
<211> LENGTH: 234
<212> TYPE: DNA
<213> ORGANISM: artificial sequence
<220> FEATURE:
<223> OTHER INFORMATION: Rv3893c (PE36)

<400> SEQUENCE: 5
atggtgtgga gcgtgcagcc cgaggccgtg ctggccagcg ccgccgccga gagcgccatc      60
agcgccgaga ccgaggccgc cgccgccggc gccgccccg ccctgctgag caccaccccc     120
atgggcggcg accccgacag cgccatgttc agcgccgccc tgaacgcctg cggcgccagc     180
tacctgggcg tggtggccga gcacgccagc cagaggggcc tgttcgccgg ctga           234

<210> SEQ ID NO 6
<211> LENGTH: 77
<212> TYPE: PRT
<213> ORGANISM: artificial sequence
<220> FEATURE:
<223> OTHER INFORMATION: Rv3893c (PE36)

<400> SEQUENCE: 6

Met Val Trp Ser Val Gln Pro Glu Ala Val Leu Ala Ser Ala Ala Ala
1               5                   10                  15

Glu Ser Ala Ile Ser Ala Glu Thr Glu Ala Ala Ala Ala Gly Ala Ala
            20                  25                  30

Pro Ala Leu Leu Ser Thr Thr Pro Met Gly Gly Asp Pro Asp Ser Ala
        35                  40                  45

Met Phe Ser Ala Ala Leu Asn Ala Cys Gly Ala Ser Tyr Leu Gly Val
    50                  55                  60

Val Ala Glu His Ala Ser Gln Arg Gly Leu Phe Ala Gly
65                  70                  75

<210> SEQ ID NO 7
<211> LENGTH: 309
<212> TYPE: DNA
<213> ORGANISM: artificial sequence
<220> FEATURE:
<223> OTHER INFORMATION: Rv0285 (PE5)

<400> SEQUENCE: 7
atgaccctga gggtggtgcc cgagggcctg gccgccgcca cgccgccgt ggaggccctg       60 accgccaggc tggccgccgc ccacgccagc gccgccccg tgatcaccgc cgtggtgccc      120

-continued

```
cccgccgccg accccgtgag cctgcagacc gccgccggct tcagcgccca gggcgtggag      180
cacgccgtgg tgaccgccga gggcgtggag gagctgggca gggccggcgt gggcgtgggc      240
gagagcggcg ccagctacct ggccggcgac gccgccgccg ccgccaccta cggcgtggtg      300
ggcggctga                                                              309
```

<210> SEQ ID NO 8
<211> LENGTH: 102
<212> TYPE: PRT
<213> ORGANISM: artificial sequence
<220> FEATURE:
<223> OTHER INFORMATION: Rv0285 (PE5)

<400> SEQUENCE: 8

```
Met Thr Leu Arg Val Val Pro Glu Gly Leu Ala Ala Ala Ser Ala Ala
1               5                   10                  15

Val Glu Ala Leu Thr Ala Arg Leu Ala Ala Ala His Ala Ser Ala Ala
            20                  25                  30

Pro Val Ile Thr Ala Val Val Pro Ala Ala Asp Pro Val Ser Leu
        35                  40                  45

Gln Thr Ala Ala Gly Phe Ser Ala Gln Gly Val Glu His Ala Val Val
    50                  55                  60

Thr Ala Glu Gly Val Glu Glu Leu Gly Arg Ala Gly Val Gly Val Gly
65                  70                  75                  80

Glu Ser Gly Ala Ser Tyr Leu Ala Gly Asp Ala Ala Ala Ala Thr
                85                  90                  95

Tyr Gly Val Val Gly Gly
            100
```

<210> SEQ ID NO 9
<211> LENGTH: 303
<212> TYPE: DNA
<213> ORGANISM: artificial sequence
<220> FEATURE:
<223> OTHER INFORMATION: Rv1818c (PE_PGRS33)

<400> SEQUENCE: 9

```
atgagcttcg tggtgaccat ccccgaggcc ctggccgccg tggccaccga cctggccggc      60
atcggcagca ccatcggcac cgccaacgcc gccgccgccg tgcccaccac caccgtgctg      120
gccgccgccg ccgacgaggt gagcgccgcc atggccgccc tgttcagcgg ccacgcccag      180
gcctaccagg ccctgagcgc ccaggccgcc ctgttccacg agcagttcgt gagggccctg      240
accgccggcg ccggcagcta cgccgccgcc gaggccgcca cgccgccccc cctggagggc      300
tga                                                                    303
```

<210> SEQ ID NO 10
<211> LENGTH: 100
<212> TYPE: PRT
<213> ORGANISM: artificial sequence
<220> FEATURE:
<223> OTHER INFORMATION: Rv1818c (PE_PGRS33)

<400> SEQUENCE: 10

```
Met Ser Phe Val Val Thr Ile Pro Glu Ala Leu Ala Ala Val Ala Thr
1               5                   10                  15

Asp Leu Ala Gly Ile Gly Ser Thr Ile Gly Thr Ala Asn Ala Ala Ala
            20                  25                  30
```

```
Ala Val Pro Thr Thr Val Leu Ala Ala Ala Ala Asp Glu Val Ser
        35                  40                  45

Ala Ala Met Ala Ala Leu Phe Ser Gly His Ala Gln Ala Tyr Gln Ala
 50                  55                  60

Leu Ser Ala Gln Ala Ala Leu Phe His Glu Gln Phe Val Arg Ala Leu
 65                  70                  75                  80

Thr Ala Gly Ala Gly Ser Tyr Ala Ala Ala Glu Ala Ala Ser Ala Ala
                 85                  90                  95

Pro Leu Glu Gly
            100

<210> SEQ ID NO 11
<211> LENGTH: 333
<212> TYPE: DNA
<213> ORGANISM: artificial sequence
<220> FEATURE:
<223> OTHER INFORMATION: Rv0159c (PE3)

<400> SEQUENCE: 11
atgagctacg tgatcgccgc ccccgagatg ctggccacca ccgccgccga cgtggacggc    60
atcggcagcg ccatcagggc cgccagcgcc agcgccgccg ccccaccac cggcctgctg    120 gccgccgccg ccgacgaggt gagcagcgcc gccgccgccc tgttcagcga gtacgccagg    180
gagtgccagg aggtgctgaa gcaggccgcc gccttccacg gcgagttcac cagggccctg    240
gccgccgccg gcgccgccta cgcccaggcc gaggccagca acaccgccgc catgagcggc    300
accgccggca gcagcggcgc cctgggcagc tga                                333

<210> SEQ ID NO 12
<211> LENGTH: 110
<212> TYPE: PRT
<213> ORGANISM: artificial sequence
<220> FEATURE:
<223> OTHER INFORMATION: Rv0159c (PE3)

<400> SEQUENCE: 12

Met Ser Tyr Val Ile Ala Ala Pro Glu Met Leu Ala Thr Thr Ala Ala
 1               5                  10                  15

Asp Val Asp Gly Ile Gly Ser Ala Ile Arg Ala Ala Ser Ala Ser Ala
                 20                  25                  30

Ala Gly Pro Thr Thr Gly Leu Leu Ala Ala Ala Ala Asp Glu Val Ser
        35                  40                  45

Ser Ala Ala Ala Ala Leu Phe Ser Glu Tyr Ala Arg Glu Cys Gln Glu
 50                  55                  60

Val Leu Lys Gln Ala Ala Ala Phe His Gly Glu Phe Thr Arg Ala Leu
65                   70                  75                  80

Ala Ala Ala Gly Ala Ala Tyr Ala Gln Ala Glu Ala Ser Asn Thr Ala
                 85                  90                  95

Ala Met Ser Gly Thr Ala Gly Ser Ser Gly Ala Leu Gly Ser
            100                 105                 110

<210> SEQ ID NO 13
<211> LENGTH: 333
<212> TYPE: DNA
<213> ORGANISM: artificial sequence
<220> FEATURE:
<223> OTHER INFORMATION: Rv1172c (PE12)
```

<400> SEQUENCE: 13

```
atgagcttcg tgttcgccgc ccccgaggcc ctggccgccg ccgccgccga catggccggc      60
atcggcagca ccctgaacgc cgccaacgtg gtggccgccg tgcccaccac cggcgtgctg     120
gccgccgccg ccgacgaggt gagcacccag gtggccgccc tgctgagcgc ccacgcccag     180
ggctaccagc agctgagcag gcagatgatg accgccttcc acgaccagtt cgtgcaggcc     240
ctgagggcca gcgccgacgc ctacgccacc gccgaggcca gcgccgccca gaccatggtg     300
aacgccgtga acgccccggc cagggccctg tga                                  333
```

<210> SEQ ID NO 14
<211> LENGTH: 110
<212> TYPE: PRT
<213> ORGANISM: artificial sequence
<220> FEATURE:
<223> OTHER INFORMATION: Rv1172c (PE12)

<400> SEQUENCE: 14

```
Met Ser Phe Val Phe Ala Ala Pro Glu Ala Leu Ala Ala Ala Ala Ala
1               5                   10                  15

Asp Met Ala Gly Ile Gly Ser Thr Leu Asn Ala Ala Asn Val Val Ala
            20                  25                  30

Ala Val Pro Thr Thr Gly Val Leu Ala Ala Ala Ala Asp Glu Val Ser
        35                  40                  45

Thr Gln Val Ala Ala Leu Leu Ser Ala His Ala Gln Gly Tyr Gln Gln
    50                  55                  60

Leu Ser Arg Gln Met Met Thr Ala Phe His Asp Gln Phe Val Gln Ala
65                  70                  75                  80

Leu Arg Ala Ser Ala Asp Ala Tyr Ala Thr Ala Glu Ala Ser Ala Ala
                85                  90                  95

Gln Thr Met Val Asn Ala Val Asn Ala Pro Ala Arg Ala Leu
            100                 105                 110
```

<210> SEQ ID NO 15
<211> LENGTH: 2097
<212> TYPE: DNA
<213> ORGANISM: artificial sequence
<220> FEATURE:
<223> OTHER INFORMATION: Rv3872-Rv1788-Rv3893c-Rv0285-Rv1818c-Rv0159c-Rv1172c fusion protein

<400> SEQUENCE: 15

```
atggagaaga tgagccacga ccccatcgcc gccgacatcg gcacccaggt gagcgacaac      60
gccctgcacg gcgtgaccgc cggcagcacc gccctgacca gcgtgaccgg cctggtgccc     120 gccgcgccg acgaggtgag cgcccaggcc gccaccgcct tcaccagcga gggcatccag     180
ctgctggcca gcaacgccag cgcccaggac cagctgcaca gggccggcga ggccgtgcag     240
gacgtggcca ggacctacag ccagatcgac gacggcgccg ccggcgtgtt cgccgagatg     300
agcttcgtga ccacccagcc cgaggccctg gccgccgccg ccggcagcct gcagggcatc     360
ggcagcgccc tgaacgccca gaacgccgcc gccgccaccc ccaccaccgg cgtggtgccc     420
gccgccgccg acgaggtgag cgccctgacc gccgcccagt cgccgcccca cgcccagatc     480
taccaggccg tgagcgccca ggccgccgcc atccacgaga tgttcgtgaa cacccctgcag     540 atgagcagcg gcagctacgc cgccaccgag gccgccaacg ccgccgccgc cggcgccgcc     600
gccatggtgt ggagcgtgca gcccgaggcc gtgctggcca cgccgccgc cgagagcgcc     660
```

```
atcagcgccg agaccgaggc cgccgccgcc ggcgccgccc ccgccctgct gagcaccacc    720
cccatgggcg gcgaccccga cagcgccatg ttcagcgccg ccctgaacgc ctgcggcgcc    780
agctacctgg gcgtggtggc cgagcacgcc agccagaggg gcctgttcgc cggcatgacc    840
ctgagggtgg tgcccgaggg cctggccgcc gccagcgccg ccgtggaggc cctgaccgcc    900
aggctggccg ccgcccacgc cagcgccgcc cccgtgatca ccgccgtggt gccccccgcc    960
gccgaccccg tgagcctgca gaccgccgcc ggcttcagcg cccagggcgt ggagcacgcc   1020
gtggtgaccg ccgagggcgt ggaggagctg ggcagggccg gcgtgggcgt gggcgagagc   1080
ggcgccagct acctggccgg cgacgccgcc gccgccgcca cctacggcgt ggtgggcggc   1140
atgagcttcg tggtgaccat ccccgaggcc ctggccgccg tggccaccga cctggccggc   1200
atcggcagca ccatcggcac cgccaacgcc gccgccgccg tgcccaccac caccgtgctg   1260
gccgccgccg ccgacgaggt gagcgccgcc atggccgccc tgttcagcgg ccacgcccag   1320
gcctaccagg ccctgagcgc ccaggccgcc ctgttccacg agcagttcgt gagggccctg   1380
accgccggcg ccggcagcta cgccgccatg agctacgtga tcgccgcccc cgagatgctg   1440
gccaccaccg ccgccgacgt ggacggcatc ggcagcgcca tcagggccgc cagcgccagc   1500
gccgccggcc ccaccaccgg cctgctggcc gccgccgcca cgaggtgag cagcgccgcc   1560 gccgccctgt tcagcgagta cgccagggag tgccaggagg tgctgaagca ggccgccgcc   1620
ttccacggcg agttcaccag ggccctggcc gccgccggcg ccgcctacgc ccaggccgag   1680
gccagcaaca ccgccgccat gagcggcacc gccggcagca gcggcgccct gggcagcatg   1740
agcttcgtgt cgccgccccc cgaggccctg gccgccgccg ccgccgacat ggccggcatc   1800
ggcagcaccc tgaacgccgc caacgtggtg gccgccgtgc ccaccaccgg cgtgctggcc   1860
gccgccgccg acgaggtgag cacccaggtg gccgccctgc tgagcgccca cgcccagggc   1920
taccagcagc tgagcaggca gatgatgacc gccttccacg accagttcgt gcaggccctg   1980
agggccagcg ccgacgccta cgccaccgcc gaggccagcg ccgcccagac catggtgaac   2040
gccgtgaacg ccccgccag ggccctgtac ccctacgacg tgcccgacta cgcctga      2097
```

<210> SEQ ID NO 16
<211> LENGTH: 698
<212> TYPE: PRT
<213> ORGANISM: artificial sequence
<220> FEATURE:
<223> OTHER INFORMATION: Rv3872-Rv1788-Rv3893c-Rv0285-Rv1818c-Rv0159c-
      Rv1172c fusion protein

<400> SEQUENCE: 16

```
Met Glu Lys Met Ser His Asp Pro Ile Ala Ala Asp Ile Gly Thr Gln
1               5                   10                  15

Val Ser Asp Asn Ala Leu His Gly Val Thr Ala Gly Ser Thr Ala Leu
            20                  25                  30

Thr Ser Val Thr Gly Leu Val Pro Ala Gly Ala Asp Glu Val Ser Ala
        35                  40                  45

Gln Ala Ala Thr Ala Phe Thr Ser Glu Gly Ile Gln Leu Leu Ala Ser
    50                  55                  60

Asn Ala Ser Ala Gln Asp Gln Leu His Arg Ala Gly Glu Ala Val Gln
65                  70                  75                  80

Asp Val Ala Arg Thr Tyr Ser Gln Ile Asp Asp Gly Ala Ala Gly Val
                85                  90                  95

Phe Ala Glu Met Ser Phe Val Thr Gln Pro Glu Ala Leu Ala Ala
                100                 105                 110
```

```
Ala Ala Gly Ser Leu Gln Gly Ile Gly Ser Ala Leu Asn Ala Gln Asn
        115                 120                 125

Ala Ala Ala Ala Thr Pro Thr Thr Gly Val Val Pro Ala Ala Ala Asp
130                 135                 140

Glu Val Ser Ala Leu Thr Ala Ala Gln Phe Ala His Ala Gln Ile
145                 150                 155                 160

Tyr Gln Ala Val Ser Ala Gln Ala Ala Ile His Glu Met Phe Val
                    165                 170                 175

Asn Thr Leu Gln Met Ser Ser Gly Ser Tyr Ala Ala Thr Glu Ala Ala
                180                 185                 190

Asn Ala Ala Ala Ala Gly Ala Ala Met Val Trp Ser Val Gln Pro
                195                 200                 205

Glu Ala Val Leu Ala Ser Ala Ala Ala Glu Ser Ala Ile Ser Ala Glu
210                 215                 220

Thr Glu Ala Ala Ala Gly Ala Ala Pro Ala Leu Leu Ser Thr Thr
225                 230                 235                 240

Pro Met Gly Gly Asp Pro Asp Ser Ala Met Phe Ser Ala Ala Leu Asn
                245                 250                 255

Ala Cys Gly Ala Ser Tyr Leu Gly Val Val Ala Glu His Ala Ser Gln
        260                 265                 270

Arg Gly Leu Phe Ala Gly Met Thr Leu Arg Val Val Pro Glu Gly Leu
        275                 280                 285

Ala Ala Ala Ser Ala Ala Val Glu Ala Leu Thr Ala Arg Leu Ala Ala
        290                 295                 300

Ala His Ala Ser Ala Ala Pro Val Ile Thr Ala Val Val Pro Pro Ala
305                 310                 315                 320

Ala Asp Pro Val Ser Leu Gln Thr Ala Ala Gly Phe Ser Ala Gln Gly
                325                 330                 335

Val Glu His Ala Val Val Thr Ala Glu Gly Val Glu Leu Gly Arg
                340                 345                 350

Ala Gly Val Gly Val Gly Glu Ser Gly Ala Ser Tyr Leu Ala Gly Asp
        355                 360                 365

Ala Ala Ala Ala Ala Thr Tyr Gly Val Val Gly Gly Met Ser Phe Val
        370                 375                 380

Val Thr Ile Pro Glu Ala Leu Ala Ala Val Ala Thr Asp Leu Ala Gly
385                 390                 395                 400

Ile Gly Ser Thr Ile Gly Thr Ala Asn Ala Ala Ala Val Pro Thr
                405                 410                 415

Thr Thr Val Leu Ala Ala Ala Ala Asp Glu Val Ser Ala Ala Met Ala
                420                 425                 430

Ala Leu Phe Ser Gly His Ala Gln Ala Tyr Gln Ala Leu Ser Ala Gln
                435                 440                 445

Ala Ala Leu Phe His Glu Gln Phe Val Arg Ala Leu Thr Ala Gly Ala
        450                 455                 460

Gly Ser Tyr Ala Ala Met Ser Tyr Val Ile Ala Ala Pro Glu Met Leu
465                 470                 475                 480

Ala Thr Thr Ala Ala Asp Val Asp Gly Ile Gly Ser Ala Ile Arg Ala
                485                 490                 495

Ala Ser Ala Ser Ala Ala Gly Pro Thr Thr Gly Leu Leu Ala Ala Ala
                500                 505                 510

Ala Asp Glu Val Ser Ser Ala Ala Ala Leu Phe Ser Glu Tyr Ala
                515                 520                 525
```

-continued

```
Arg Glu Cys Gln Glu Val Leu Lys Gln Ala Ala Ala Phe His Gly Glu
    530                 535                 540
Phe Thr Arg Ala Leu Ala Ala Ala Gly Ala Ala Tyr Ala Gln Ala Glu
545                 550                 555                 560
Ala Ser Asn Thr Ala Ala Met Ser Gly Thr Ala Gly Ser Ser Gly Ala
                565                 570                 575
Leu Gly Ser Met Ser Phe Val Phe Ala Ala Pro Glu Ala Leu Ala Ala
            580                 585                 590
Ala Ala Ala Asp Met Ala Gly Ile Gly Ser Thr Leu Asn Ala Ala Asn
        595                 600                 605
Val Val Ala Ala Val Pro Thr Thr Gly Val Leu Ala Ala Ala Ala Asp
610                 615                 620
Glu Val Ser Thr Gln Val Ala Ala Leu Leu Ser Ala His Ala Gln Gly
625                 630                 635                 640
Tyr Gln Gln Leu Ser Arg Gln Met Met Thr Ala Phe His Asp Gln Phe
                645                 650                 655
Val Gln Ala Leu Arg Ala Ser Ala Asp Ala Tyr Ala Thr Ala Glu Ala
            660                 665                 670
Ser Ala Ala Gln Thr Met Val Asn Ala Val Asn Ala Pro Ala Arg Ala
        675                 680                 685
Leu Tyr Pro Tyr Asp Val Pro Asp Tyr Ala
    690                 695
```

```
<210> SEQ ID NO 17
<211> LENGTH: 9
<212> TYPE: PRT
<213> ORGANISM: artificial sequence
<220> FEATURE:
<223> OTHER INFORMATION: Hemagglutinin tag

<400> SEQUENCE: 17

Tyr Pro Tyr Asp Val Pro Asp Tyr Ala
1               5

<210> SEQ ID NO 18
<211> LENGTH: 543
<212> TYPE: DNA
<213> ORGANISM: artificial sequence
<220> FEATURE:
<223> OTHER INFORMATION: Rv3873 (PPE68)

<400> SEQUENCE: 18
atgctgtggc acgccatgcc ccccgagctg aacaccgcca ggctgatggc cggcgccggc      60
cccgccccca tgctggccgc cgccgccggc tggcagaccc tgagcgccgc cctggacgcc     120
caggccgtgg agctgaccgc caggctgaac agcctgggcg aggcctggac cggcggcggc     180
agcgacaagg ccctggccgc cgccacccccc atggtggtgt ggctgcagac cgccagcacc     240
caggccaaga ccagggccat gcaggccacc gccaggccg ccgcctacac ccaggccatg      300
gccaccaccc ccagcctgcc cgagatcgcc gccaaccaca tcacccaggc cgtgctgacc     360
gccaccaact tcttcggcat caacaccatc cccatcgccc tgaccgagat ggactacttc     420
atcaggatgt ggaaccaggc cgccctggcc atggaggtgt accaggccga gaccgccgtg     480 aacacccctgt tcgagaagct ggagcccatg gccagcatcc tggaccccgg cgccagccag     540
tga                                                                   543

<210> SEQ ID NO 19
<211> LENGTH: 180
```

<212> TYPE: PRT
<213> ORGANISM: artificial sequence
<220> FEATURE:
<223> OTHER INFORMATION: Rv3873 (PPE68)

<400> SEQUENCE: 19

```
Met Leu Trp His Ala Met Pro Pro Glu Leu Asn Thr Ala Arg Leu Met
1               5                   10                  15

Ala Gly Ala Gly Pro Ala Pro Met Leu Ala Ala Ala Gly Trp Gln
            20                  25                  30

Thr Leu Ser Ala Ala Leu Asp Ala Gln Ala Val Glu Leu Thr Ala Arg
        35                  40                  45

Leu Asn Ser Leu Gly Glu Ala Trp Thr Gly Gly Ser Asp Lys Ala
    50                  55                  60

Leu Ala Ala Ala Thr Pro Met Val Val Trp Leu Gln Thr Ala Ser Thr
65                  70                  75                  80

Gln Ala Lys Thr Arg Ala Met Gln Ala Thr Ala Gln Ala Ala Tyr
                85                  90                  95

Thr Gln Ala Met Ala Thr Thr Pro Ser Leu Pro Glu Ile Ala Ala Asn
                100                 105                 110

His Ile Thr Gln Ala Val Leu Thr Ala Thr Asn Phe Phe Gly Ile Asn
            115                 120                 125

Thr Ile Pro Ile Ala Leu Thr Glu Met Asp Tyr Phe Ile Arg Met Trp
130                 135                 140

Asn Gln Ala Ala Leu Ala Met Glu Val Tyr Gln Ala Glu Thr Ala Val
145                 150                 155                 160

Asn Thr Leu Phe Glu Lys Leu Glu Pro Met Ala Ser Ile Leu Asp Pro
                165                 170                 175

Gly Ala Ser Gln
            180
```

<210> SEQ ID NO 20
<211> LENGTH: 543
<212> TYPE: DNA
<213> ORGANISM: artificial sequence
<220> FEATURE:
<223> OTHER INFORMATION: Rv1387 (PPE20)

<400> SEQUENCE: 20

```
atgaccgagc cctggatcgc cttcccccc  gaggtgcaca gcgccatgct gaactacggc    60
gccggcgtgg gccccatgct gatcagcgcc acccagaacg gcgagctgag cgcccagtac   120
gccgaggccg ccagcgaggt ggaggagctg ctgggcgtgg tggccagcga gggctggcag   180
ggccaggccg ccgaggcctt cgtggccgcc tacatgccct tcctggcctg gctgatccag   240
gccagcgccc actgcgtgga gatggccgcc cagcagcacg tggtgatcga ggcctacacc   300
gccgccgtgg agctgatgcc cacccaggtg gagctggccg ccaaccagat caagctggcc   360
gtgctggtgg ccaccaactt cttcggcatc aacaccatcc ccatcgccat caacgaggcc   420
gagtacgtgg agatgtgggt gagggccgcc accaccatgg ccacctacag caccgtgagc   480
aggagcgccc tgagcgccat gccccacacc agcccccccc ccctgatcct gaagagcgac   540
tga                                                                 543
```

<210> SEQ ID NO 21
<211> LENGTH: 180
<212> TYPE: PRT
<213> ORGANISM: artificial sequence
<220> FEATURE:

<223> OTHER INFORMATION: Rv1387 (PPE20)

<400> SEQUENCE: 21

```
Met Thr Glu Pro Trp Ile Ala Phe Pro Pro Glu Val His Ser Ala Met
1               5                   10                  15

Leu Asn Tyr Gly Ala Gly Val Gly Pro Met Leu Ile Ser Ala Thr Gln
            20                  25                  30

Asn Gly Glu Leu Ser Ala Gln Tyr Ala Glu Ala Ala Ser Glu Val Glu
        35                  40                  45

Glu Leu Leu Gly Val Val Ala Ser Glu Gly Trp Gln Gly Gln Ala Ala
    50                  55                  60

Glu Ala Phe Val Ala Ala Tyr Met Pro Phe Leu Ala Trp Leu Ile Gln
65                  70                  75                  80

Ala Ser Ala Asp Cys Val Glu Met Ala Ala Gln Gln His Val Val Ile
                85                  90                  95

Glu Ala Tyr Thr Ala Ala Val Glu Leu Met Pro Thr Gln Val Glu Leu
            100                 105                 110

Ala Ala Asn Gln Ile Lys Leu Ala Val Leu Val Ala Thr Asn Phe Phe
        115                 120                 125

Gly Ile Asn Thr Ile Pro Ile Ala Ile Asn Glu Ala Glu Tyr Val Glu
    130                 135                 140

Met Trp Val Arg Ala Ala Thr Thr Met Ala Thr Tyr Ser Thr Val Ser
145                 150                 155                 160

Arg Ser Ala Leu Ser Ala Met Pro His Thr Ser Pro Pro Leu Ile
                165                 170                 175

Leu Lys Ser Asp
            180
```

<210> SEQ ID NO 22
<211> LENGTH: 543
<212> TYPE: DNA
<213> ORGANISM: artificial sequence
<220> FEATURE:
<223> OTHER INFORMATION: Rv3892c (PPE69)

<400> SEQUENCE: 22

```
atgcccgacc ccggctgggc cgccaggacc cccgaggcca acgacctgct gctgaccgcc      60
ggcaccggcg tgggcaccca cctggccaac cagaccgcct ggaccaccct gggcgccagc     120
caccacgcca gcggcgtggc cagcgccatc aacaccgccg ccaccgccgc cagctggctg     180
ggcgtgggca cgccgccag cgccctgaac gtgaccatgc tgaacgccac cctgcacggc     240
ctggccggct gggtggacgt gaagcccgcc gtggtgagca ccgccatcgc cgccttcgag     300
accgccaacg ccgccatgag gcccgccccc gagtgcatgg agaacaggga cgagtggggc     360
gtggacaacg ccatcaaccc cagcgtgctg tggaccctga ccccaggat cgtgagcctg     420
gacgtggagt acttcggcgt gatgtggccc aacaacgccg ccgtgggcgc cacctacggc     480
ggcgtgctgg ccgccctggc cgagagcctg gccatccccc ccccgtggc caccatgggc     540
tga                                                                  543
```

<210> SEQ ID NO 23
<211> LENGTH: 180
<212> TYPE: PRT
<213> ORGANISM: artificial sequence
<220> FEATURE:
<223> OTHER INFORMATION: Rv3892c (PPE69)

<400> SEQUENCE: 23

Met Pro Asp Pro Gly Trp Ala Ala Arg Thr Pro Glu Ala Asn Asp Leu
1               5                   10                  15

Leu Leu Thr Ala Gly Thr Gly Val Gly Thr His Leu Ala Asn Gln Thr
            20                  25                  30

Ala Trp Thr Thr Leu Gly Ala Ser His His Ala Ser Gly Val Ala Ser
        35                  40                  45

Ala Ile Asn Thr Ala Ala Thr Ala Ala Ser Trp Leu Gly Val Gly Ser
    50                  55                  60

Ala Ala Ser Ala Leu Asn Val Thr Met Leu Asn Ala Thr Leu His Gly
65                  70                  75                  80

Leu Ala Gly Trp Val Asp Val Lys Pro Ala Val Val Ser Thr Ala Ile
                85                  90                  95

Ala Ala Phe Glu Thr Ala Asn Ala Ala Met Arg Pro Ala Pro Glu Cys
            100                 105                 110

Met Glu Asn Arg Asp Glu Trp Gly Val Asp Asn Ala Ile Asn Pro Ser
        115                 120                 125

Val Leu Trp Thr Leu Thr Pro Arg Ile Val Ser Leu Asp Val Glu Tyr
    130                 135                 140

Phe Gly Val Met Trp Pro Asn Asn Ala Ala Val Gly Ala Thr Tyr Gly
145                 150                 155                 160

Gly Val Leu Ala Ala Leu Ala Glu Ser Leu Ala Ile Pro Pro Val
                165                 170                 175

Ala Thr Met Gly
            180

<210> SEQ ID NO 24
<211> LENGTH: 543
<212> TYPE: DNA
<213> ORGANISM: artificial sequence
<220> FEATURE:
<223> OTHER INFORMATION: Rv1789 (PPE26)

<400> SEQUENCE: 24
atggacttcg gcgccctgcc ccccgaggtg aacagcgtga ggatgtacgc cggccccggc      60
agcgccccca tggtggccgc cgccagcgcc tggaacggcc tggccgccga gctgagcagc     120
gccgccaccg gctacgagac cgtgatcacc cagctgagca gcgagggctg gctgggcccc     180
gccagcgccg ccatggccga ggccgtggcc ccctacgtgg cctggatgag cgccgccgcc     240
gcccaggccg agcaggccgc cacccaggcc agggccgccg ccgccgcctt cgaggccgcc     300
ttcgccgcca ccgtgccccc ccccctgatc gccgccaaca gggccagcct gatgcagctg     360
atcagcacca acgtgttcgg ccagaacacc agcgccatcg ccgccgccga ggcccagtac     420
ggcgagatgt gggcccagga cagcgccgcc atgtacgcct acgccggcag cagcgccagc     480
gccagcgccg tgaccccctt cagcaccccc cccagatcg ccaaccccac cgcccagggc     540
tga                                                                   543

<210> SEQ ID NO 25
<211> LENGTH: 180
<212> TYPE: PRT
<213> ORGANISM: artificial sequence
<220> FEATURE:
<223> OTHER INFORMATION: Rv1789 (PPE26)

<400> SEQUENCE: 25

Met Asp Phe Gly Ala Leu Pro Pro Glu Val Asn Ser Val Arg Met Tyr
1               5                   10                  15

Ala Gly Pro Gly Ser Ala Pro Met Val Ala Ala Ser Ala Trp Asn
            20                  25                  30

Gly Leu Ala Ala Glu Leu Ser Ser Ala Ala Thr Gly Tyr Glu Thr Val
        35                  40                  45

Ile Thr Gln Leu Ser Ser Glu Gly Trp Leu Gly Pro Ala Ser Ala Ala
    50                  55                  60

Met Ala Glu Ala Val Ala Pro Tyr Val Ala Trp Met Ser Ala Ala Ala
65                  70                  75                  80

Ala Gln Ala Glu Gln Ala Ala Thr Gln Ala Arg Ala Ala Ala Ala Ala
                85                  90                  95

Phe Glu Ala Ala Phe Ala Ala Thr Val Pro Pro Leu Ile Ala Ala
            100                 105                 110

Asn Arg Ala Ser Leu Met Gln Leu Ile Ser Thr Asn Val Phe Gly Gln
        115                 120                 125

Asn Thr Ser Ala Ile Ala Ala Glu Ala Gln Tyr Gly Glu Met Trp
    130                 135                 140

Ala Gln Asp Ser Ala Ala Met Tyr Ala Tyr Ala Gly Ser Ser Ala Ser
145                 150                 155                 160

Ala Ser Ala Val Thr Pro Phe Ser Thr Pro Pro Gln Ile Ala Asn Pro
                165                 170                 175

Thr Ala Gln Gly
            180

<210> SEQ ID NO 26
<211> LENGTH: 543
<212> TYPE: DNA
<213> ORGANISM: artificial sequence
<220> FEATURE:
<223> OTHER INFORMATION: Rv1800 (PPE28)

<400> SEQUENCE: 26
atgctgccca acttcgccgt gctgcccccc gaggtgaaca gcgccagggt gttcgccggc      60
gccggcagcg cccccatgct ggccgccgcc gccgcctggg acgacctggc cagcgagctg     120
cactgcgccg ccatgagctt cggcagcgtg accagcggcc tggtggtggg ctggtggcag     180
ggcagcgcca cgccgccat ggtggacgcc gccgccagct acatcggctg gctgagcacc      240
agcgccgccc acgccgaggg cgccgccggc ctggccaggg ccgccgtgag cgtgttcgag     300
gaggccctgg ccgccaccgt gcaccccgcc atggtggccg ccaacagggc ccaggtggcc     360
agcctggtgg ccagcaacct gttcggccag aacgcccccg ccatcgccgc cctggagagc     420
ctgtacgagt gcatgtgggc ccaggacgcc gccgccatgg ccggctacta cgtgggcgcc     480
agcgccgtgg ccacccagct ggccagctgg ctgcagaggc tgcagagcat ccccggcgcc     540
tga                                                                  543

<210> SEQ ID NO 27
<211> LENGTH: 180
<212> TYPE: PRT
<213> ORGANISM: artificial sequence
<220> FEATURE:
<223> OTHER INFORMATION: Rv1800 (PPE28)

<400> SEQUENCE: 27

```
Met Leu Pro Asn Phe Ala Val Leu Pro Pro Glu Val Asn Ser Ala Arg
1               5                   10                  15

Val Phe Ala Gly Ala Gly Ser Ala Pro Met Leu Ala Ala Ala Ala
            20                  25                  30

Trp Asp Asp Leu Ala Ser Glu Leu His Cys Ala Ala Met Ser Phe Gly
                35                  40                  45

Ser Val Thr Ser Gly Leu Val Val Gly Trp Trp Gln Gly Ser Ala Ser
    50                  55                  60

Ala Ala Met Val Asp Ala Ala Ala Ser Tyr Ile Gly Trp Leu Ser Thr
65                  70                  75                  80

Ser Ala Ala His Ala Glu Gly Ala Ala Gly Leu Ala Arg Ala Ala Val
                85                  90                  95

Ser Val Phe Glu Glu Ala Leu Ala Ala Thr Val His Pro Ala Met Val
            100                 105                 110

Ala Ala Asn Arg Ala Gln Val Ala Ser Leu Val Ala Ser Asn Leu Phe
            115                 120                 125

Gly Gln Asn Ala Pro Ala Ile Ala Ala Leu Glu Ser Leu Tyr Glu Cys
    130                 135                 140

Met Trp Ala Gln Asp Ala Ala Ala Met Ala Gly Tyr Tyr Val Gly Ala
145                 150                 155                 160

Ser Ala Val Ala Thr Gln Leu Ala Ser Trp Leu Gln Arg Leu Gln Ser
                165                 170                 175

Ile Pro Gly Ala
            180
```

<210> SEQ ID NO 28
<211> LENGTH: 543
<212> TYPE: DNA
<213> ORGANISM: artificial sequence
<220> FEATURE:
<223> OTHER INFORMATION: Rv1039c (PPE15)

<400> SEQUENCE: 28

```
atggacttcg gcgccctgcc ccccgagatc aacagcgcca ggatgtacgc cggcgccggc      60
gccggcccca tgatggccgc cggcgccgcc tggaacggcc tggccgccga gctgggcacc     120
accgccgcca gctacgagag cgtgatcacc aggctgacca ccgagagctg gatgggcccc     180
gccagcatgg ccatggtggc cgccgcccag ccctacctgg cctggctgac ctacaccgcc     240
gaggccgccg cccacgccgg cagccaggcc atggccagcg ccgccgccta cgaggccgcc     300
tacgccatga ccgtgccccc cgaggtggtg ccgccaaca gggccctgct ggccgccctg     360
gtggccacca acgtgctggg catcaacacc cccgccatca tggccaccga ggccctgtac     420
gccgagatgt gggcccagga cgccctggcc atgtacggct acgccgccgc cagcggcgcc     480
gccggcatgc tgcagcccct gagcccccc agccagacca ccaaccccgg cggcctggcc     540
tga                                                                    543
```

<210> SEQ ID NO 29
<211> LENGTH: 180
<212> TYPE: PRT
<213> ORGANISM: artificial sequence
<220> FEATURE:
<223> OTHER INFORMATION: Rv1039c (PPE15)

<400> SEQUENCE: 29

| | | | | | | | | | | | | | | | |
|---|---|---|---|---|---|---|---|---|---|---|---|---|---|---|---|
| Met | Asp | Phe | Gly | Ala | Leu | Pro | Pro | Glu | Ile | Asn | Ser | Ala | Arg | Met | Tyr |
| 1 | | | | 5 | | | | | 10 | | | | | 15 | |

| Ala | Gly | Ala | Gly | Ala | Gly | Pro | Met | Met | Ala | Ala | Gly | Ala | Ala | Trp | Asn |
|---|---|---|---|---|---|---|---|---|---|---|---|---|---|---|---|
| | | | 20 | | | | | 25 | | | | | 30 | | |

| Gly | Leu | Ala | Ala | Glu | Leu | Gly | Thr | Thr | Ala | Ala | Ser | Tyr | Glu | Ser | Val |
|---|---|---|---|---|---|---|---|---|---|---|---|---|---|---|---|
| | | | | 35 | | | | | 40 | | | | | 45 | |

| Ile | Thr | Arg | Leu | Thr | Thr | Glu | Ser | Trp | Met | Gly | Pro | Ala | Ser | Met | Ala |
|---|---|---|---|---|---|---|---|---|---|---|---|---|---|---|---|
| | 50 | | | | | 55 | | | | | 60 | | | | |

| Met | Val | Ala | Ala | Ala | Gln | Pro | Tyr | Leu | Ala | Trp | Leu | Thr | Tyr | Thr | Ala |
|---|---|---|---|---|---|---|---|---|---|---|---|---|---|---|---|
| 65 | | | | | 70 | | | | | 75 | | | | | 80 |

| Glu | Ala | Ala | Ala | His | Ala | Gly | Ser | Gln | Ala | Met | Ala | Ser | Ala | Ala | Ala |
|---|---|---|---|---|---|---|---|---|---|---|---|---|---|---|---|
| | | | | 85 | | | | | 90 | | | | | 95 | |

| Tyr | Glu | Ala | Ala | Tyr | Ala | Met | Thr | Val | Pro | Pro | Glu | Val | Val | Ala | Ala |
|---|---|---|---|---|---|---|---|---|---|---|---|---|---|---|---|
| | | | 100 | | | | | 105 | | | | | 110 | | |

| Asn | Arg | Ala | Leu | Leu | Ala | Ala | Leu | Val | Ala | Thr | Asn | Val | Leu | Gly | Ile |
|---|---|---|---|---|---|---|---|---|---|---|---|---|---|---|---|
| | | | | 115 | | | | | 120 | | | | | 125 | |

| Asn | Thr | Pro | Ala | Ile | Met | Ala | Thr | Glu | Ala | Leu | Tyr | Ala | Glu | Met | Trp |
|---|---|---|---|---|---|---|---|---|---|---|---|---|---|---|---|
| | 130 | | | | | 135 | | | | | 140 | | | | |

| Ala | Gln | Asp | Ala | Leu | Ala | Met | Tyr | Gly | Tyr | Ala | Ala | Ala | Ser | Gly | Ala |
|---|---|---|---|---|---|---|---|---|---|---|---|---|---|---|---|
| 145 | | | | | 150 | | | | | 155 | | | | | 160 |

| Ala | Gly | Met | Leu | Gln | Pro | Leu | Ser | Pro | Pro | Ser | Gln | Thr | Thr | Asn | Pro |
|---|---|---|---|---|---|---|---|---|---|---|---|---|---|---|---|
| | | | | 165 | | | | | 170 | | | | | 175 | |

| Gly | Gly | Leu | Ala |
|---|---|---|---|
| | | | 180 |

<210> SEQ ID NO 30
<211> LENGTH: 1650
<212> TYPE: DNA
<213> ORGANISM: artificial sequence
<220> FEATURE:
<223> OTHER INFORMATION: Rv3873-Rv1387-Rv3892c fusion protein

<400> SEQUENCE: 30

| | | |
|---|---|---|
| atgctgtggc acgccatgcc ccccgagctg aacaccgcca ggctgatggc cggcgccggc | 60 |
| cccgccccca tgctggccgc cgccgccggc tggcagaccc tgagcgccgc cctggacgcc | 120 |
| caggccgtgg agctgaccgc caggctgaac agcctgggcg aggcctggac cggcggcggc | 180 |
| agcgacaagg ccctggccgc cgccacccc atggtggtgt ggctgcagac cgccagcacc | 240 |
| caggccaaga ccagggccat gcaggccacc gcccaggccg ccgcctacac ccaggccatg | 300 |
| gccaccaccc ccagcctgcc cgagatcgcc gccaaccaca tcacccaggc cgtgctgacc | 360 |
| gccaccaact tcttcggcat caacaccatc cccatcgccc tgaccgagat ggactacttc | 420 |
| atcaggatgt ggaaccaggc cgccctggcc atggaggtgt accaggccga ccgccgtg | 480 |
| aacaccctgt tcgagaagct ggagcccatg ccagcatcc tggaccccgg cgccagccag | 540 |
| atgaccgagc cctggatcgc cttcccccc gaggtgcaca gcgccatgct gaactacggc | 600 |
| gccggcgtgg gccccatgct gatcagcgcc acccagaacg cgagctgag cgccagtac | 660 |
| gccgaggccg ccagcgaggt ggaggagctg ctgggcgtgg tggccagcga gggctggcag | 720 |
| ggccaggccg ccgaggcctt cgtggccgcc tacatgccct tcctggcctg gctgatccag | 780 |
| gccagcgccg actgcgtgga gatggccgcc agcagcacg tggtgatcga ggcctacacc | 840 |
| gccgccgtgg agctgatgcc cacccaggtg agctggccg ccaaccagat caagctggcc | 900 |

```
gtgctggtgg ccaccaactt cttcggcatc aacaccatcc ccatcgccat caacgaggcc    960
gagtacgtgg agatgtgggt gagggccgcc accaccatgg ccacctacag caccgtgagc   1020
aggagcgccc tgagcgccat gccccacacc agccccccc ccctgatcct gaagagcgac    1080
atgcccgacc ccggctgggc cgccaggacc cccgaggcca acgacctgct gctgaccgcc   1140
ggcaccggcg tgggcaccca cctggccaac cagaccgcct ggaccaccct gggcgccagc   1200
caccacgcca gcggcgtggc cagcgccatc aacaccgccg ccaccgccgc cagctggctg   1260
ggcgtgggca gcgccgccag cgccctgaac gtgaccatgc tgaacgccac cctgcacggc   1320
ctggccggct gggtggacgt gaagcccgcc gtggtgagca ccgccatcgc cgccttcgag   1380
accgccaacg ccgccatgag gcccgccccc gagtgcatgg agaacaggga cgagtggggc   1440
gtggacaacg ccatcaaccc cagcgtgctg tggaccctga cccccaggat cgtgagcctg   1500
gacgtggagt acttcggcgt gatgtggccc aacaacgccg ccgtgggcgc cacctacggc   1560
ggcgtgctgg ccgccctggc cgagagcctg gccatccccc ccccgtggc caccatgggc    1620 tacccctacg acgtgcccga ctacgcctga                                    1650

<210> SEQ ID NO 31
<211> LENGTH: 549
<212> TYPE: PRT
<213> ORGANISM: artificial sequence
<220> FEATURE:
<223> OTHER INFORMATION: Rv3873-Rv1387-Rv3892c fusion protein

<400> SEQUENCE: 31

Met Leu Trp His Ala Met Pro Pro Glu Leu Asn Thr Ala Arg Leu Met
1               5                   10                  15

Ala Gly Ala Gly Pro Ala Pro Met Leu Ala Ala Ala Gly Trp Gln
            20                  25                  30

Thr Leu Ser Ala Ala Leu Asp Ala Gln Ala Val Glu Leu Thr Ala Arg
        35                  40                  45

Leu Asn Ser Leu Gly Glu Ala Trp Thr Gly Gly Ser Asp Lys Ala
    50                  55                  60

Leu Ala Ala Ala Thr Pro Met Val Val Trp Leu Gln Thr Ala Ser Thr
65                  70                  75                  80

Gln Ala Lys Thr Arg Ala Met Gln Ala Thr Ala Gln Ala Ala Tyr
                85                  90                  95

Thr Gln Ala Met Ala Thr Thr Pro Ser Leu Pro Glu Ile Ala Ala Asn
            100                 105                 110

His Ile Thr Gln Ala Val Leu Thr Ala Thr Asn Phe Phe Gly Ile Asn
        115                 120                 125

Thr Ile Pro Ile Ala Leu Thr Glu Met Asp Tyr Phe Ile Arg Met Trp
    130                 135                 140

Asn Gln Ala Ala Leu Ala Met Glu Val Tyr Gln Ala Glu Thr Ala Val
145                 150                 155                 160

Asn Thr Leu Phe Glu Lys Leu Glu Pro Met Ala Ser Ile Leu Asp Pro
                165                 170                 175

Gly Ala Ser Gln Met Thr Glu Pro Trp Ile Ala Phe Pro Pro Glu Val
            180                 185                 190

His Ser Ala Met Leu Asn Tyr Gly Ala Gly Val Gly Pro Met Leu Ile
        195                 200                 205

Ser Ala Thr Gln Asn Gly Glu Leu Ser Ala Gln Tyr Ala Glu Ala Ala
    210                 215                 220
```

Ser Glu Val Glu Glu Leu Leu Gly Val Val Ala Ser Glu Gly Trp Gln
225                 230                 235                 240

Gly Gln Ala Ala Glu Ala Phe Val Ala Ala Tyr Met Pro Phe Leu Ala
            245                 250                 255

Trp Leu Ile Gln Ala Ser Ala Asp Cys Val Glu Met Ala Ala Gln Gln
                260                 265                 270

His Val Val Ile Glu Ala Tyr Thr Ala Ala Val Glu Leu Met Pro Thr
            275                 280                 285

Gln Val Glu Leu Ala Ala Asn Gln Ile Lys Leu Ala Val Leu Val Ala
        290                 295                 300

Thr Asn Phe Phe Gly Ile Asn Thr Ile Pro Ile Ala Ile Asn Glu Ala
305                 310                 315                 320

Glu Tyr Val Glu Met Trp Val Arg Ala Thr Thr Met Ala Thr Tyr
                325                 330                 335

Ser Thr Val Ser Arg Ser Ala Leu Ser Ala Met Pro His Thr Ser Pro
                340                 345                 350

Pro Pro Leu Ile Leu Lys Ser Asp Met Pro Asp Pro Gly Trp Ala Ala
            355                 360                 365

Arg Thr Pro Glu Ala Asn Asp Leu Leu Leu Thr Ala Gly Thr Gly Val
        370                 375                 380

Gly Thr His Leu Ala Asn Gln Thr Ala Trp Thr Thr Leu Gly Ala Ser
385                 390                 395                 400

His His Ala Ser Gly Val Ala Ser Ala Ile Asn Thr Ala Ala Thr Ala
                405                 410                 415

Ala Ser Trp Leu Gly Val Gly Ser Ala Ala Ser Ala Leu Asn Val Thr
                420                 425                 430

Met Leu Asn Ala Thr Leu His Gly Leu Ala Gly Trp Val Asp Val Lys
            435                 440                 445

Pro Ala Val Val Ser Thr Ala Ile Ala Ala Phe Glu Thr Ala Asn Ala
450                 455                 460

Ala Met Arg Pro Ala Pro Glu Cys Met Glu Asn Arg Asp Glu Trp Gly
465                 470                 475                 480

Val Asp Asn Ala Ile Asn Pro Ser Val Leu Trp Thr Leu Thr Pro Arg
                485                 490                 495

Ile Val Ser Leu Asp Val Glu Tyr Phe Gly Val Met Trp Pro Asn Asn
                500                 505                 510

Ala Ala Val Gly Ala Thr Tyr Gly Gly Val Leu Ala Ala Leu Ala Glu
            515                 520                 525

Ser Leu Ala Ile Pro Pro Val Ala Thr Met Gly Tyr Pro Tyr Asp
        530                 535                 540

Val Pro Asp Tyr Ala
545

<210> SEQ ID NO 32
<211> LENGTH: 1650
<212> TYPE: DNA
<213> ORGANISM: artificial sequence
<220> FEATURE:
<223> OTHER INFORMATION: Rv1789-Rv1800-Rv1039c fusion protein

<400> SEQUENCE: 32
atggacttcg gcgccctgcc ccccgaggtg aacagcgtga ggatgtacgc cggccccggc    60
agcgccccca tggtggccgc cgccagcgcc tggaacggcc tggccgccga gctgagcagc    120
gccgccaccg gctacgagac cgtgatcacc cagctgagca gcgagggctg gctgggcccc    180

```
gccagcgccg ccatggccga ggccgtggcc ccctacgtgg cctggatgag cgccgccgcc    240
gcccaggccg agcaggccgc cacccaggcc agggccgccg ccgccgcctt cgaggccgcc    300
ttcgccgcca ccgtgccccc ccccctgatc gccgccaaca gggccagcct gatgcagctg    360
atcagcacca acgtgttcgg ccagaacacc agcgccatcg ccgccgccga ggcccagtac    420
ggcgagatgt gggcccagga cagcgccgcc atgtacgcct acgccggcag cagcgccagc    480
gccagcgccg tgaccccctt cagcaccccc ccccagatcg ccaaccccac cgcccagggc    540
atgctgccca acttcgccgt gctgcccccc gaggtgaaca gcgccagggt gttcgccggc    600
gccggcagcg cccccatgct ggccgccgcc gccgcctggg acgacctggc cagcgagctg    660
cactgcgccg ccatgagctt cggcagcgtg accagcggcc tggtggtggg ctggtggcag    720
ggcagcgcca gcgccgccat ggtggacgcc gccgccagct acatcggctg gctgagcacc    780
agcgccgccc acgccgaggg cgccgccggc ctggccaggg ccgccgtgag cgtgttcgag    840
gaggccctgg ccgccaccgt gcacccgcc atggtggccg ccaacagggc ccaggtggcc    900
agcctggtgg ccagcaacct gttcggccag aacgcccccg ccatcgccgc cctggagagc    960
ctgtacgagt gcatgtgggc ccaggacgcc gccgccatgg ccggctacta cgtgggcgcc   1020
agcgccgtgg ccacccagct ggccagctgg ctgcagaggc tgcagagcat ccccggcgcc   1080
atggacttcg gcgccctgcc ccccgagatc aacagcgcca ggatgtacgc cggcgccggc   1140
gccggcccca tgatggccgc cggcgccgcc tggaacggcc tggccgccga gctgggcacc   1200
accgccgcca gctacgagag cgtgatcacc aggctgacca ccgagagctg gatgggcccc   1260
gccagcatgg ccatggtggc cgccgcccag ccctacctgg cctggctgac ctacaccgcc   1320
gaggccgccg cccacgccgg cagccaggcc atggccagcg ccgccgccta cgaggccgcc   1380
tacgccatga ccgtgccccc cgaggtggtg gccgccaaca gggccctgct ggccgccctg   1440
gtggccacca acgtgctggg catcaacacc cccgccatca tggccaccga ggccctgtac   1500
gccgagatgt gggcccagga cgccctggcc atgtacggct acgccgccgc cagcggcgcc   1560
gccggcatgc tgcagcccct gagccccccc agccagacca ccaaccccgg cggcctggcc   1620 taccccctacg acgtgcccga ctacgcctga                                   1650
```

<210> SEQ ID NO 33
<211> LENGTH: 549
<212> TYPE: PRT
<213> ORGANISM: artificial sequence
<220> FEATURE:
<223> OTHER INFORMATION: Rv1789-Rv1800-Rv1039c fusion protein

<400> SEQUENCE: 33

```
Met Asp Phe Gly Ala Leu Pro Pro Glu Val Asn Ser Val Arg Met Tyr
1               5                   10                  15

Ala Gly Pro Gly Ser Ala Pro Met Val Ala Ala Ala Ser Ala Trp Asn
            20                  25                  30

Gly Leu Ala Ala Glu Leu Ser Ser Ala Ala Thr Gly Tyr Glu Thr Val
        35                  40                  45

Ile Thr Gln Leu Ser Ser Glu Gly Trp Leu Gly Pro Ala Ser Ala Ala
    50                  55                  60

Met Ala Glu Ala Val Ala Pro Tyr Val Ala Trp Met Ser Ala Ala Ala
65                  70                  75                  80

Ala Gln Ala Glu Gln Ala Ala Thr Gln Ala Arg Ala Ala Ala Ala Ala
                85                  90                  95
```

```
Phe Glu Ala Ala Phe Ala Ala Thr Val Pro Pro Pro Leu Ile Ala Ala
                100                 105                 110

Asn Arg Ala Ser Leu Met Gln Leu Ile Ser Thr Asn Val Phe Gly Gln
            115                 120                 125

Asn Thr Ser Ala Ile Ala Ala Glu Ala Gln Tyr Gly Glu Met Trp
        130                 135                 140

Ala Gln Asp Ser Ala Ala Met Tyr Ala Tyr Ala Gly Ser Ser Ala Ser
145                 150                 155                 160

Ala Ser Ala Val Thr Pro Phe Ser Thr Pro Pro Gln Ile Ala Asn Pro
                165                 170                 175

Thr Ala Gln Gly Met Leu Pro Asn Phe Ala Val Leu Pro Pro Glu Val
            180                 185                 190

Asn Ser Ala Arg Val Phe Ala Gly Ala Gly Ser Ala Pro Met Leu Ala
            195                 200                 205

Ala Ala Ala Ala Trp Asp Asp Leu Ala Ser Glu Leu His Cys Ala Ala
            210                 215                 220

Met Ser Phe Gly Ser Val Thr Ser Gly Leu Val Val Gly Trp Trp Gln
225                 230                 235                 240

Gly Ser Ala Ser Ala Ala Met Val Asp Ala Ala Ser Tyr Ile Gly
            245                 250                 255

Trp Leu Ser Thr Ser Ala Ala His Ala Glu Gly Ala Ala Gly Leu Ala
            260                 265                 270

Arg Ala Ala Val Ser Val Phe Glu Glu Ala Leu Ala Ala Thr Val His
            275                 280                 285

Pro Ala Met Val Ala Ala Asn Arg Ala Gln Val Ala Ser Leu Val Ala
290                 295                 300

Ser Asn Leu Phe Gly Gln Asn Ala Pro Ala Ile Ala Ala Leu Glu Ser
305                 310                 315                 320

Leu Tyr Glu Cys Met Trp Ala Gln Asp Ala Ala Ala Met Ala Gly Tyr
                325                 330                 335

Tyr Val Gly Ala Ser Ala Val Ala Thr Gln Leu Ala Ser Trp Leu Gln
            340                 345                 350

Arg Leu Gln Ser Ile Pro Gly Ala Met Asp Phe Gly Ala Leu Pro Pro
            355                 360                 365

Glu Ile Asn Ser Ala Arg Met Tyr Ala Gly Ala Gly Ala Gly Pro Met
370                 375                 380

Met Ala Ala Gly Ala Ala Trp Asn Gly Leu Ala Ala Glu Leu Gly Thr
385                 390                 395                 400

Thr Ala Ala Ser Tyr Glu Ser Val Ile Thr Arg Leu Thr Thr Glu Ser
            405                 410                 415

Trp Met Gly Pro Ala Ser Met Ala Met Val Ala Ala Ala Gln Pro Tyr
            420                 425                 430

Leu Ala Trp Leu Thr Tyr Thr Ala Glu Ala Ala His Ala Gly Ser
            435                 440                 445

Gln Ala Met Ala Ser Ala Ala Ala Tyr Glu Ala Ala Tyr Ala Met Thr
            450                 455                 460

Val Pro Pro Glu Val Val Ala Ala Asn Arg Ala Leu Leu Ala Ala Leu
465                 470                 475                 480

Val Ala Thr Asn Val Leu Gly Ile Asn Thr Pro Ala Ile Met Ala Thr
            485                 490                 495

Glu Ala Leu Tyr Ala Glu Met Trp Ala Gln Asp Ala Leu Ala Met Tyr
                500                 505                 510
```

```
Gly Tyr Ala Ala Ala Ser Gly Ala Ala Gly Met Leu Gln Pro Leu Ser
            515                 520                 525

Pro Pro Ser Gln Thr Thr Asn Pro Gly Gly Leu Ala Tyr Pro Tyr Asp
        530                 535                 540

Val Pro Asp Tyr Ala
545

<210> SEQ ID NO 34
<211> LENGTH: 363
<212> TYPE: DNA
<213> ORGANISM: artificial sequence
<220> FEATURE:
<223> OTHER INFORMATION: Rv3017c (esxQ)

<400> SEQUENCE: 34
gtgagccaga gcatgtacag ctaccccgcc atgaccgcca acgtgggcga catggccggc      60
tacaccggca ccacccagag cctgggcgcc gacatcgcca gcgagaggac cgcccccagc    120
agggcctgcc agggcgacct gggcatgagc caccaggact ggcaggccca gtggaaccag    180
gccatggagg ccctggccag ggcctacagg aggtgcagga gggccctgag gcagatcggc    240
gtgctggaga ggcccgtggg cgacagcagc gactgcggca ccatcagggt gggcagcttc    300
aggggcaggt ggctggaccc caggcacgcc ggccccgcca ccgccgccga cgccggcgac    360
tga                                                                 363

<210> SEQ ID NO 35
<211> LENGTH: 120
<212> TYPE: PRT
<213> ORGANISM: artificial sequence
<220> FEATURE:
<223> OTHER INFORMATION: Rv3017c (esxQ)

<400> SEQUENCE: 35

Val Ser Gln Ser Met Tyr Ser Tyr Pro Ala Met Thr Ala Asn Val Gly
1               5                   10                  15

Asp Met Ala Gly Tyr Thr Gly Thr Thr Gln Ser Leu Gly Ala Asp Ile
            20                  25                  30

Ala Ser Glu Arg Thr Ala Pro Ser Arg Ala Cys Gln Gly Asp Leu Gly
        35                  40                  45

Met Ser His Gln Asp Trp Gln Ala Gln Trp Asn Gln Ala Met Glu Ala
    50                  55                  60

Leu Ala Arg Ala Tyr Arg Arg Cys Arg Arg Ala Leu Arg Gln Ile Gly
65                  70                  75                  80

Val Leu Glu Arg Pro Val Gly Asp Ser Ser Asp Cys Gly Thr Ile Arg
                85                  90                  95

Val Gly Ser Phe Arg Gly Arg Trp Leu Asp Pro Arg His Ala Gly Pro
            100                 105                 110

Ala Thr Ala Ala Asp Ala Gly Asp
        115                 120

<210> SEQ ID NO 36
<211> LENGTH: 294
<212> TYPE: DNA
<213> ORGANISM: artificial sequence
<220> FEATURE:
<223> OTHER INFORMATION: Rv3020c (esxS)
```

<400> SEQUENCE: 36

```
atgagcctgc tggacgccca catcccccag ctgatcgcca gccacaccgc cttcgccgcc    60
aaggccggcc tgatgaggca ccatcggc caggccgagc agcaggccat gagcgcccag    120
gccttccacc agggcgagag cgccgccgcc ttccagggcg cccacgccag gttcgtggcc   180
gccgccgcca aggtgaacac cctgctggac atcgcccagg ccaacctggg cgaggccgcc   240
ggcacctacg tggccgccga cgccgccgcc gccagcagct acaccggctt ctga          294
```

<210> SEQ ID NO 37
<211> LENGTH: 97
<212> TYPE: PRT
<213> ORGANISM: artificial sequence
<220> FEATURE:
<223> OTHER INFORMATION: Rv3020c (esxS)

<400> SEQUENCE: 37

```
Met Ser Leu Leu Asp Ala His Ile Pro Gln Leu Ile Ala Ser His Thr
1               5                   10                  15

Ala Phe Ala Ala Lys Ala Gly Leu Met Arg His Thr Ile Gly Gln Ala
            20                  25                  30

Glu Gln Gln Ala Met Ser Ala Gln Ala Phe His Gln Gly Glu Ser Ala
        35                  40                  45

Ala Ala Phe Gln Gly Ala His Ala Arg Phe Val Ala Ala Ala Lys
    50                  55                  60

Val Asn Thr Leu Leu Asp Ile Ala Gln Ala Asn Leu Gly Glu Ala Ala
65                  70                  75                  80

Gly Thr Tyr Val Ala Ala Asp Ala Ala Ala Ser Ser Tyr Thr Gly
                85                  90                  95

Phe
```

<210> SEQ ID NO 38
<211> LENGTH: 291
<212> TYPE: DNA
<213> ORGANISM: artificial sequence
<220> FEATURE:
<223> OTHER INFORMATION: Rv3019c (esxR)

<400> SEQUENCE: 38

```
atgagccaga tcatgtacaa ctaccccgcc atgatggccc acgccggcga catggccggc    60
tacgccggca ccctgcagag cctgggcgcc gacatcgcca gcgagcaggc cgtgctgagc   120
agcgcctggc agggcgacac cggcatcacc taccagggct ggcagaccca gtggaaccag   180
gccctggagg acctggtgag gcctaccag agcatgagcg gcacccacga gagcaacacc   240
atggccatgc tggccaggga cggcgccgag gccgccaagt ggggcggctg a             291
```

<210> SEQ ID NO 39
<211> LENGTH: 96
<212> TYPE: PRT
<213> ORGANISM: artificial sequence
<220> FEATURE:
<223> OTHER INFORMATION: Rv3019c (esxR)

<400> SEQUENCE: 39

```
Met Ser Gln Ile Met Tyr Asn Tyr Pro Ala Met Met Ala His Ala Gly
1               5                   10                  15

Asp Met Ala Gly Tyr Ala Gly Thr Leu Gln Ser Leu Gly Ala Asp Ile
            20                  25                  30
```

```
Ala Ser Glu Gln Ala Val Leu Ser Ala Trp Gln Gly Asp Thr Gly
         35                  40                  45

Ile Thr Tyr Gln Gly Trp Gln Thr Gln Trp Asn Gln Ala Leu Glu Asp
 50                  55                  60

Leu Val Arg Ala Tyr Gln Ser Met Ser Gly Thr His Glu Ser Asn Thr
 65                  70                  75                  80

Met Ala Met Leu Ala Arg Asp Gly Ala Glu Ala Lys Trp Gly Gly
                 85                  90                  95

<210> SEQ ID NO 40
<211> LENGTH: 324
<212> TYPE: DNA
<213> ORGANISM: artificial sequence
<220> FEATURE:
<223> OTHER INFORMATION: Rv3891c (esxD)

<400> SEQUENCE: 40
gtggccgaca ccatccaggt gaccccccag atgctgagga gcaccgccaa cgacatccag    60
gccaacatgg agcaggccat gggcatcgcc aagggctacc tggccaacca ggagaacgtg   120
atgaaccccg ccacctggag cggcaccggc gtggtggcca gccacatgac cgccaccgag   180
atcaccaacg agctgaacaa ggtgctgacc ggcggcacca ggctggccga gggcctggtg   240
caggccgccg ccctgatgga gggccacgag gccgacagcc agaccgcctt ccaggccctg   300
ttcggcgcca gccacggcag ctga                                          324

<210> SEQ ID NO 41
<211> LENGTH: 107
<212> TYPE: PRT
<213> ORGANISM: artificial sequence
<220> FEATURE:
<223> OTHER INFORMATION: Rv3891c (esxD)

<400> SEQUENCE: 41

Val Ala Asp Thr Ile Gln Val Thr Pro Gln Met Leu Arg Ser Thr Ala
 1               5                  10                  15

Asn Asp Ile Gln Ala Asn Met Glu Gln Ala Met Gly Ile Ala Lys Gly
                20                  25                  30

Tyr Leu Ala Asn Gln Glu Asn Val Met Asn Pro Ala Thr Trp Ser Gly
             35                  40                  45

Thr Gly Val Val Ala Ser His Met Thr Ala Thr Glu Ile Thr Asn Glu
 50                  55                  60

Leu Asn Lys Val Leu Thr Gly Gly Thr Arg Leu Ala Glu Gly Leu Val
 65                  70                  75                  80

Gln Ala Ala Ala Leu Met Glu Gly His Glu Ala Asp Ser Gln Thr Ala
                 85                  90                  95

Phe Gln Ala Leu Phe Gly Ala Ser His Gly Ser
            100                 105

<210> SEQ ID NO 42
<211> LENGTH: 285
<212> TYPE: DNA
<213> ORGANISM: artificial sequence
<220> FEATURE:
<223> OTHER INFORMATION: Rv2346c (esxO)

<400> SEQUENCE: 42
atgaccatca actaccagtt cggcgacgtg gacgcccacg cgccatgat cagggcccag    60 gccggcctgc tggaggccga gaccaggcc atcgtgaggg acgtgctggc cgccggcgac   120
```

```
ttctggggcg gcgccggcag cgtggcctgc caggagttca tcacccagct gggcaggaac    180
ttccaggtga tctacgagca ggccaacgcc cacggccaga aggtgcaggc cgccggcaac    240
aacatggccc agaccgacag cgccgtgggc agcagctggg cctga                   285
```

```
<210> SEQ ID NO 43
<211> LENGTH: 94
<212> TYPE: PRT
<213> ORGANISM: artificial sequence
<220> FEATURE:
<223> OTHER INFORMATION: Rv2346c (esxO)

<400> SEQUENCE: 43

Met Thr Ile Asn Tyr Gln Phe Gly Asp Val Asp Ala His Gly Ala Met
1               5                   10                  15

Ile Arg Ala Gln Ala Gly Leu Leu Glu Ala Glu His Gln Ala Ile Val
                20                  25                  30

Arg Asp Val Leu Ala Ala Gly Asp Phe Trp Gly Gly Ala Gly Ser Val
            35                  40                  45

Ala Cys Gln Glu Phe Ile Thr Gln Leu Gly Arg Asn Phe Gln Val Ile
        50                  55                  60

Tyr Glu Gln Ala Asn Ala His Gly Gln Lys Val Gln Ala Ala Gly Asn
65                  70                  75                  80

Asn Met Ala Gln Thr Asp Ser Ala Val Gly Ser Ser Trp Ala
                85                  90
```

```
<210> SEQ ID NO 44
<211> LENGTH: 318
<212> TYPE: DNA
<213> ORGANISM: artificial sequence
<220> FEATURE:
<223> OTHER INFORMATION: Rv3445c (esxU)

<400> SEQUENCE: 44
gtgagcaccc ccaacaccct gaacgccgac ttcgacctga tgaggagcgt ggccggcatc     60
accgacgcca ggaacgagga gatcagggcc atgctgcagg ccttcatcgg caggatgagc    120
ggcgtgcccc ccagcgtgtg gggcggcctg gccgccgcca ggttccagga cgtggtggac    180
aggtggaacg ccgagagcac caggctgtac cacgtgctgc acgccatcgc cgacaccatc    240
aggcacaacg aggccgccct gagggaggcc ggccagatcc acgccaggca tcgccgcc     300 gccggcggcg acctgtga                                                  318
```

```
<210> SEQ ID NO 45
<211> LENGTH: 105
<212> TYPE: PRT
<213> ORGANISM: artificial sequence
<220> FEATURE:
<223> OTHER INFORMATION: Rv3445c (esxU)

<400> SEQUENCE: 45

Val Ser Thr Pro Asn Thr Leu Asn Ala Asp Phe Asp Leu Met Arg Ser
1               5                   10                  15

Val Ala Gly Ile Thr Asp Ala Arg Asn Glu Glu Ile Arg Ala Met Leu
                20                  25                  30

Gln Ala Phe Ile Gly Arg Met Ser Gly Val Pro Pro Ser Val Trp Gly
            35                  40                  45

Gly Leu Ala Ala Ala Arg Phe Gln Asp Val Val Asp Arg Trp Asn Ala
        50                  55                  60
```

Glu Ser Thr Arg Leu Tyr His Val Leu His Ala Ile Ala Asp Thr Ile
65                  70                  75                  80

Arg His Asn Glu Ala Ala Leu Arg Glu Ala Gly Gln Ile His Ala Arg
                85                  90                  95

His Ile Ala Ala Ala Gly Gly Asp Leu
            100                 105

<210> SEQ ID NO 46
<211> LENGTH: 285
<212> TYPE: DNA
<213> ORGANISM: artificial sequence
<220> FEATURE:
<223> OTHER INFORMATION: Rv3619c (esxV)

<400> SEQUENCE: 46
atgaccatca actaccagtt cggcgacgtg gacgcccacg gcgccatgat cagggcccag     60
gccggcagcc tggaggccga gcaccaggcc atcatcagcg acgtgctgac cgccagcgac    120
ttctggggcg gcgccggcag cgccgcctgc cagggcttca tcacccagct gggcaggaac    180
ttccaggtga tctacgagca ggccaacgcc cacggccaga aggtgcaggc cgccggcaac    240
aacatggccc agaccgacag cgccgtgggc agcagctggg cctga                    285

<210> SEQ ID NO 47
<211> LENGTH: 94
<212> TYPE: PRT
<213> ORGANISM: artificial sequence
<220> FEATURE:
<223> OTHER INFORMATION: Rv3619c (esxV)

<400> SEQUENCE: 47

Met Thr Ile Asn Tyr Gln Phe Gly Asp Val Asp Ala His Gly Ala Met
1               5                   10                  15

Ile Arg Ala Gln Ala Gly Ser Leu Glu Ala Glu His Gln Ala Ile Ile
            20                  25                  30

Ser Asp Val Leu Thr Ala Ser Asp Phe Trp Gly Gly Ala Gly Ser Ala
        35                  40                  45

Ala Cys Gln Gly Phe Ile Thr Gln Leu Gly Arg Asn Phe Gln Val Ile
    50                  55                  60

Tyr Glu Gln Ala Asn Ala His Gly Gln Lys Val Gln Ala Ala Gly Asn
65                  70                  75                  80

Asn Met Ala Gln Thr Asp Ser Ala Val Gly Ser Ser Trp Ala
                85                  90

<210> SEQ ID NO 48
<211> LENGTH: 288
<212> TYPE: DNA
<213> ORGANISM: artificial sequence
<220> FEATURE:
<223> OTHER INFORMATION: Rv3875 (esxA, ESAT6)

<400> SEQUENCE: 48
atgaccgagc agcagtggaa cttcgccggc atcgaggccg ccgccagcgc catccagggc     60
aacgtgacca gcatccacag cctgctggac gagggcaagc agagcctgac caagctggcc    120
gccgcctggg gcggcagcgg cagcgaggcc taccagggcg tgcagcagaa gtgggacgcc    180
accgccaccg agctgaacaa cgccctgcag aacctggcca ggaccatcag cgaggccggc    240
caggccatgg ccagcaccga gggcaacgtg accggcatgt cgcctga                  288

-continued

<210> SEQ ID NO 49
<211> LENGTH: 95
<212> TYPE: PRT
<213> ORGANISM: artificial sequence
<220> FEATURE:
<223> OTHER INFORMATION: Rv3875 (esxA, ESAT6)

<400> SEQUENCE: 49

```
Met Thr Glu Gln Gln Trp Asn Phe Ala Gly Ile Glu Ala Ala Ser
1               5                   10                  15

Ala Ile Gln Gly Asn Val Thr Ser Ile His Ser Leu Leu Asp Glu Gly
            20                  25                  30

Lys Gln Ser Leu Thr Lys Leu Ala Ala Ala Trp Gly Gly Ser Gly Ser
        35                  40                  45

Glu Ala Tyr Gln Gly Val Gln Gln Lys Trp Asp Ala Thr Ala Thr Glu
    50                  55                  60

Leu Asn Asn Ala Leu Gln Asn Leu Ala Arg Thr Ile Ser Glu Ala Gly
65                  70                  75                  80

Gln Ala Met Ala Ser Thr Glu Gly Asn Val Thr Gly Met Phe Ala
                85                  90                  95
```

<210> SEQ ID NO 50
<211> LENGTH: 303
<212> TYPE: DNA
<213> ORGANISM: artificial sequence
<220> FEATURE:
<223> OTHER INFORMATION: Rv3874 (esxB, CFP10)

<400> SEQUENCE: 50

```
atggccgaga tgaagaccga cgccgccacc ctggcccagg aggccggcaa cttcgagagg      60
atcagcggcg acctgaagac ccagatcgac caggtggaga gcaccgccgg cagcctgcag     120
ggccagtgga ggggcgccgc cggcaccgcc gcccaggccg ccgtggtgag gttccaggag     180
gccgccaaca agcagaagca ggagctggac gagatcagca ccaacatcag gcaggccggc     240
gtgcagtaca gcagggccga cgaggagcag cagcaggccc tgagcagcca gatgggcttc     300
tga                                                                  303
```

<210> SEQ ID NO 51
<211> LENGTH: 100
<212> TYPE: PRT
<213> ORGANISM: artificial sequence
<220> FEATURE:
<223> OTHER INFORMATION: Rv3874 (esxB, CFP10)

<400> SEQUENCE: 51

```
Met Ala Glu Met Lys Thr Asp Ala Ala Thr Leu Ala Gln Glu Ala Gly
1               5                   10                  15

Asn Phe Glu Arg Ile Ser Gly Asp Leu Lys Thr Gln Ile Asp Gln Val
            20                  25                  30

Glu Ser Thr Ala Gly Ser Leu Gln Gly Gln Trp Arg Gly Ala Ala Gly
        35                  40                  45

Thr Ala Ala Gln Ala Ala Val Val Arg Phe Gln Glu Ala Ala Asn Lys
    50                  55                  60

Gln Lys Gln Glu Leu Asp Glu Ile Ser Thr Asn Ile Arg Gln Ala Gly
65                  70                  75                  80

Val Gln Tyr Ser Arg Ala Asp Glu Glu Gln Gln Gln Ala Leu Ser Ser
                85                  90                  95

Gln Met Gly Phe
            100
```

<210> SEQ ID NO 52
<211> LENGTH: 1887
<212> TYPE: DNA
<213> ORGANISM: artificial sequence
<220> FEATURE:
<223> OTHER INFORMATION: Rv3017c-Rv3020c-Rv3019c-Rv3891c-Rv2346c-Rv3445c
      fusion protein

<400> SEQUENCE: 52

```
gtgagccaga gcatgtacag ctaccccgcc atgaccgcca acgtgggcga catggccggc      60
tacaccggca ccacccagag cctgggcgcc gacatcgcca gcgagaggac cgccccagc     120
agggcctgcc agggcgacct gggcatgagc caccaggact ggcaggccca gtggaaccag     180
gccatggagg ccctgccag ggcctacagg aggtgcagga gggccctgag gcagatcggc      240
gtgctggaga ggcccgtggg cgacagcagc gactgcggca ccatcagggt gggcagcttc     300
aggggcaggt ggctgacccc caggcacgcc ggccccgcca ccgccgccga cgccggcgac     360
atgagcctgc tggacgccca tcccccag ctgatcgcca gccacaccgc cttcgccgcc       420
aaggccggcc tgatgaggca caccatcggc caggccgagc agcaggccat gagcgcccag     480
gccttccacc agggcgagag cgccgccgcc ttcagggcg cccacgccag gttcgtggcc      540
gccgccgcca aggtgaacac cctgctggac atcgcccagg ccaacctggg cgaggccgcc     600
ggcacctacg tggccgccga cgccgccgcc gccagcagct acaccggctt catgagccag     660
atcatgtaca actaccccgc catgatggcc cacgccggcg acatggccgg ctacgccggc     720
accctgcaga gctgggcgc cgacatcgcc agcgagcagg ccgtgctgag cagcgcctgg     780
cagggcgaca ccggcatcac ctaccagggc tggcagaccc agtggaacca ggccctggag     840
gacctggtga gggcctacca gagcatgagc ggcacccacg agagcaacac catggccatg     900
ctggccaggg acggcgccga ggccgccaag tggggcggcg tggccgacac catccaggtg     960
accccccaga tgctgaggag caccgccaac gacatccagg ccaacatgga gcaggccatg    1020
ggcatcgcca agggctacct ggccaaccag gagaacgtga tgaaccccgc cacctggagc    1080
ggcaccggcg tggtggccag ccacatgacc gccaccgaga tcaccaacga gctgaacaag    1140
gtgctgaccg gcggcaccag gctggccgag ggcctggtgc aggccgccgc cctgatggag    1200
ggccacgagg ccgacagcca gaccgccttc cagggcctgt cggcgccag ccacggcagc     1260
atgaccatca actaccagtt cggcgacgtg gacgcccacg cgccatgat cagggcccag    1320
gccggcctgc tggaggccga gaccaggcc atcgtgaggg acgtgctggc cgccggcgac    1380
ttctggggcg cgccggcag cgtggcctgc caggagttca tcacccagct gggcaggaac    1440
ttccaggtga tctacgagca ggccaacgcc acggccaga aggtgcaggc cgccggcaac    1500
aacatggccc agaccgacag cgccgtgggc agcagctggg ccgtgagcac ccccaacacc   1560
ctgaacgccg acttcgacct gatgaggagc gtggccggca tcaccgacgc caggaacgag   1620
gagatcaggg ccatgctgca ggccttcatc ggcaggatga gcggcgtgcc ccccagcgtg    1680
tggggcggcc tggccgccgc caggttccag gacgtggtgg acaggtggaa cgccgagagc    1740
accaggctgt accacgtgct gcacgccatc gccgacacca tcaggcacaa cgaggccgcc    1800
ctgagggagg ccggccagat ccacgccagg cacatcgccg ccgccggcgg cgacctgtac    1860
ccctacgacg tgcccgacta cgcctga                                       1887
```

<210> SEQ ID NO 53
<211> LENGTH: 628

<212> TYPE: PRT
<213> ORGANISM: artificial sequence
<220> FEATURE:
<223> OTHER INFORMATION: Rv3017c-Rv3020c-Rv3019c-Rv3891c-Rv2346c-Rv3445c
       fusion protein

<400> SEQUENCE: 53

Val Ser Gln Ser Met Tyr Ser Tyr Pro Ala Met Thr Ala Asn Val Gly
1               5                   10                  15

Asp Met Ala Gly Tyr Thr Gly Thr Thr Gln Ser Leu Gly Ala Asp Ile
            20                  25                  30

Ala Ser Glu Arg Thr Ala Pro Ser Arg Ala Cys Gln Gly Asp Leu Gly
        35                  40                  45

Met Ser His Gln Asp Trp Gln Ala Gln Trp Asn Gln Ala Met Glu Ala
    50                  55                  60

Leu Ala Arg Ala Tyr Arg Arg Cys Arg Arg Ala Leu Arg Gln Ile Gly
65                  70                  75                  80

Val Leu Glu Arg Pro Val Gly Asp Ser Ser Asp Cys Gly Thr Ile Arg
                85                  90                  95

Val Gly Ser Phe Arg Gly Arg Trp Leu Asp Pro Arg His Ala Gly Pro
            100                 105                 110

Ala Thr Ala Ala Asp Ala Gly Asp Met Ser Leu Leu Asp Ala His Ile
        115                 120                 125

Pro Gln Leu Ile Ala Ser His Thr Ala Phe Ala Ala Lys Ala Gly Leu
    130                 135                 140

Met Arg His Thr Ile Gly Gln Ala Glu Gln Ala Met Ser Ala Gln
145                 150                 155                 160

Ala Phe His Gln Gly Glu Ser Ala Ala Phe Gln Gly Ala His Ala
                165                 170                 175

Arg Phe Val Ala Ala Ala Lys Val Asn Thr Leu Leu Asp Ile Ala
            180                 185                 190

Gln Ala Asn Leu Gly Glu Ala Ala Gly Thr Tyr Val Ala Ala Asp Ala
        195                 200                 205

Ala Ala Ala Ser Ser Tyr Thr Gly Phe Met Ser Gln Ile Met Tyr Asn
    210                 215                 220

Tyr Pro Ala Met Met Ala His Ala Gly Asp Met Ala Gly Tyr Ala Gly
225                 230                 235                 240

Thr Leu Gln Ser Leu Gly Ala Asp Ile Ala Ser Glu Gln Ala Val Leu
                245                 250                 255

Ser Ser Ala Trp Gln Gly Asp Thr Gly Ile Thr Tyr Gln Gly Trp Gln
            260                 265                 270

Thr Gln Trp Asn Gln Ala Leu Glu Asp Leu Val Arg Ala Tyr Gln Ser
        275                 280                 285

Met Ser Gly Thr His Glu Ser Asn Thr Met Ala Met Leu Ala Arg Asp
    290                 295                 300

Gly Ala Glu Ala Ala Lys Trp Gly Gly Val Ala Asp Thr Ile Gln Val
305                 310                 315                 320

Thr Pro Gln Met Leu Arg Ser Thr Ala Asn Asp Ile Gln Ala Asn Met
                325                 330                 335

Glu Gln Ala Met Gly Ile Ala Lys Gly Tyr Leu Ala Asn Gln Glu Asn
            340                 345                 350

Val Met Asn Pro Ala Thr Trp Ser Gly Thr Gly Val Val Ala Ser His
        355                 360                 365

Met Thr Ala Thr Glu Ile Thr Asn Glu Leu Asn Lys Val Leu Thr Gly
    370                 375                 380

Gly Thr Arg Leu Ala Glu Gly Leu Val Gln Ala Ala Leu Met Glu
385                 390                 395                 400

Gly His Glu Ala Asp Ser Gln Thr Ala Phe Gln Ala Leu Phe Gly Ala
            405                 410                 415

Ser His Gly Ser Met Thr Ile Asn Tyr Gln Phe Gly Asp Val Asp Ala
        420                 425                 430

His Gly Ala Met Ile Arg Ala Gln Ala Gly Leu Leu Glu Ala Glu His
    435                 440                 445

Gln Ala Ile Val Arg Asp Val Leu Ala Gly Asp Phe Trp Gly
450                 455                 460

Ala Gly Ser Val Ala Cys Gln Glu Phe Ile Thr Gln Leu Gly Arg Asn
465                 470                 475                 480

Phe Gln Val Ile Tyr Glu Gln Ala Asn Ala His Gly Gln Lys Val Gln
            485                 490                 495

Ala Ala Gly Asn Asn Met Ala Gln Thr Asp Ser Ala Val Gly Ser Ser
        500                 505                 510

Trp Ala Val Ser Thr Pro Asn Thr Leu Asn Ala Asp Phe Asp Leu Met
    515                 520                 525

Arg Ser Val Ala Gly Ile Thr Asp Ala Arg Asn Glu Glu Ile Arg Ala
530                 535                 540

Met Leu Gln Ala Phe Ile Gly Arg Met Ser Gly Val Pro Pro Ser Val
545                 550                 555                 560

Trp Gly Gly Leu Ala Ala Ala Arg Phe Gln Asp Val Val Asp Arg Trp
            565                 570                 575

Asn Ala Glu Ser Thr Arg Leu Tyr His Val Leu His Ala Ile Ala Asp
        580                 585                 590

Thr Ile Arg His Asn Glu Ala Ala Leu Arg Glu Ala Gly Gln Ile His
    595                 600                 605

Ala Arg His Ile Ala Ala Gly Gly Asp Leu Tyr Pro Tyr Asp Val
610                 615                 620

Pro Asp Tyr Ala
625

<210> SEQ ID NO 54
<211> LENGTH: 897
<212> TYPE: DNA
<213> ORGANISM: artificial sequence
<220> FEATURE:
<223> OTHER INFORMATION: Rv3619c-Rv3875-Rv3874 fusion protein

<400> SEQUENCE: 54
atgaccatca actaccagtt cggcgacgtg gacgcccacg gcgccatgat cagggcccag     60
gccggcagcc tggaggccga gcaccaggcc atcatcagcg acgtgctgac cgccagcgac    120
ttctggggcg gcgccggcag cgccgcctgc cagggcttca tcacccagct gggcaggaac    180
ttccaggtga tctacgagca ggccaacgcc acggccagaa ggtgcaggc cgccggcaac    240 aacatggccc agaccgacag cgccgtgggc agcagctggg ccatgaccga gcagcagtgg    300
aacttcgccg gcatcgaggc cgccgccagc gccatccagg caacgtgac cagcatccac    360 agcctgctgg acgagggcaa gcagagcctg accaagctgg ccgccgcctg ggcggcagc    420 ggcagcgagg cctaccaggg cgtgcagcag aagtgggacg ccaccgccac cgagctgaac    480
aacgccctgc agaacctggc caggaccatc agcgaggccg ccaggccat ggccagcacc    540 gagggcaacg tgaccggcat gttcgccatg gccgagatga agaccgacgc cgccaccctg    600

-continued

```
gcccaggagg ccggcaactt cgagaggatc agcggcgacc tgaagaccca gatcgaccag    660
gtggagagca ccgccggcag cctgcagggc cagtggaggg gcgccgccgg caccgccgcc    720
caggccgccg tggtgaggtt ccaggaggcc gccaacaagc agaagcagga gctggacgag    780
atcagcacca acatcaggca ggccggcgtg cagtacagca gggccgacga ggagcagcag    840
caggccctga gcagccagat gggcttctac ccctacgacg tgcccgacta cgcctga      897
```

<210> SEQ ID NO 55
<211> LENGTH: 298
<212> TYPE: PRT
<213> ORGANISM: artificial sequence
<220> FEATURE:
<223> OTHER INFORMATION: Rv3619c-Rv3875-Rv3874 fusion protein

<400> SEQUENCE: 55

```
Met Thr Ile Asn Tyr Gln Phe Gly Asp Val Asp Ala His Gly Ala Met
1               5                   10                  15

Ile Arg Ala Gln Ala Gly Ser Leu Glu Ala Glu His Gln Ala Ile Ile
                20                  25                  30

Ser Asp Val Leu Thr Ala Ser Asp Phe Trp Gly Gly Ala Gly Ser Ala
            35                  40                  45

Ala Cys Gln Gly Phe Ile Thr Gln Leu Gly Arg Asn Phe Gln Val Ile
        50                  55                  60

Tyr Glu Gln Ala Asn Ala His Gly Gln Lys Val Gln Ala Ala Gly Asn
65                  70                  75                  80

Asn Met Ala Gln Thr Asp Ser Ala Val Gly Ser Ser Trp Ala Met Thr
                85                  90                  95

Glu Gln Gln Trp Asn Phe Ala Gly Ile Glu Ala Ala Ala Ser Ala Ile
                100                 105                 110

Gln Gly Asn Val Thr Ser Ile His Ser Leu Leu Asp Glu Gly Lys Gln
            115                 120                 125

Ser Leu Thr Lys Leu Ala Ala Ala Trp Gly Gly Ser Gly Ser Glu Ala
130                 135                 140

Tyr Gln Gly Val Gln Gln Lys Trp Asp Ala Thr Ala Thr Glu Leu Asn
145                 150                 155                 160

Asn Ala Leu Gln Asn Leu Ala Arg Thr Ile Ser Glu Ala Gly Gln Ala
                165                 170                 175

Met Ala Ser Thr Glu Gly Asn Val Thr Gly Met Phe Ala Met Ala Glu
                180                 185                 190

Met Lys Thr Asp Ala Ala Thr Leu Ala Gln Glu Ala Gly Asn Phe Glu
            195                 200                 205

Arg Ile Ser Gly Asp Leu Lys Thr Gln Ile Asp Gln Val Glu Ser Thr
210                 215                 220

Ala Gly Ser Leu Gln Gly Gln Trp Arg Gly Ala Ala Gly Thr Ala Ala
225                 230                 235                 240

Gln Ala Ala Val Val Arg Phe Gln Glu Ala Ala Asn Lys Gln Lys Gln
                245                 250                 255

Glu Leu Asp Glu Ile Ser Thr Asn Ile Arg Gln Ala Gly Val Gln Tyr
            260                 265                 270

Ser Arg Ala Asp Glu Glu Gln Gln Gln Ala Leu Ser Ser Gln Met Gly
        275                 280                 285

Phe Tyr Pro Tyr Asp Val Pro Asp Tyr Ala
    290                 295
```

<210> SEQ ID NO 56

-continued

```
<211> LENGTH: 498
<212> TYPE: DNA
<213> ORGANISM: artificial sequence
<220> FEATURE:
<223> OTHER INFORMATION: Rv2719c

<400> SEQUENCE: 56 atgaccccg tgaggccccc ccacaccccc gacccctga acctgagggg cccctggac      60 ggccccaggt ggaggagggc cgagcccgcc cagagcagga ggcccggcag gagcaggccc    120
ggcggcgccc ccctgaggta ccacaggacc ggcgtgggca tgagcaggac cggccacggc    180
agcaggcccg tgccccccgc caccaccgtg ggcctggccc tgctggccgc cgccatcacc    240
ctgtggctgg gcctggtggc ccagttcggc cagatgatca ccggcggcag cgccgacggc    300
agcgccgaca gcaccggcag ggtgcccgac aggctggccg tgtgagggt ggagaccggc     360 gagagcctgt acgacgtggc cgtgagggtg gcccccaacg cccccaccag gcaggtggcc    420
gacaggatca gggagctgaa cggcctgcag acccccgccc tggccgtggg ccagaccctg    480 atcgccccg tgggctga                                                  498

<210> SEQ ID NO 57
<211> LENGTH: 165
<212> TYPE: PRT
<213> ORGANISM: artificial sequence
<220> FEATURE:
<223> OTHER INFORMATION: Rv2719c

<400> SEQUENCE: 57

Met Thr Pro Val Arg Pro Pro His Thr Pro Asp Pro Leu Asn Leu Arg
1               5                   10                  15

Gly Pro Leu Asp Gly Pro Arg Trp Arg Arg Ala Glu Pro Ala Gln Ser
            20                  25                  30

Arg Arg Pro Gly Arg Ser Arg Pro Gly Gly Ala Pro Leu Arg Tyr His
        35                  40                  45

Arg Thr Gly Val Gly Met Ser Arg Thr Gly His Gly Ser Arg Pro Val
    50                  55                  60

Pro Pro Ala Thr Thr Val Gly Leu Ala Leu Leu Ala Ala Ala Ile Thr
65                  70                  75                  80

Leu Trp Leu Gly Leu Val Ala Gln Phe Gly Gln Met Ile Thr Gly Gly
                85                  90                  95

Ser Ala Asp Gly Ser Ala Asp Ser Thr Gly Arg Val Pro Asp Arg Leu
            100                 105                 110

Ala Val Val Arg Val Glu Thr Gly Glu Ser Leu Tyr Asp Val Ala Val
        115                 120                 125

Arg Val Ala Pro Asn Ala Pro Thr Arg Gln Val Ala Asp Arg Ile Arg
    130                 135                 140

Glu Leu Asn Gly Leu Gln Thr Pro Ala Leu Ala Val Gly Gln Thr Leu
145                 150                 155                 160

Ile Ala Pro Val Gly
                165

<210> SEQ ID NO 58
<211> LENGTH: 426
<212> TYPE: DNA
<213> ORGANISM: artificial sequence
<220> FEATURE:
<223> OTHER INFORMATION: Rv0010c
```

<400> SEQUENCE: 58

```
atgcagcaga ccgcctgggc ccccaggacc agcggcatcg ccggctgcgg cgccggcggc    60
gtggtgatgg ccatcgccag cgtgaccctg gtgaccgaca ccccggcag ggtgctgacc    120
ggcgtggccg ccctgggcct gatcctgttc gccagcgcca cctggagggc caggcccagg    180
ctggccatca cccccgacgg cctggccatc agggctggt tcaggaccca gctgctgagg    240
cacagcaaca tcaagatcat caggatcgac gagttcagga ggtacggcag gctggtgagg    300
ctgctggaga tcgagaccgt gagcggcggc ctgctgatcc tgagcaggtg ggacctgggc    360
accgaccccg tggaggtgct ggacgccctg accgccgccg gctacgccgg caggggccag    420
aggtga                                                              426
```

<210> SEQ ID NO 59
<211> LENGTH: 141
<212> TYPE: PRT
<213> ORGANISM: artificial sequence
<220> FEATURE:
<223> OTHER INFORMATION: Rv0010c

<400> SEQUENCE: 59

```
Met Gln Gln Thr Ala Trp Ala Pro Arg Thr Ser Gly Ile Ala Gly Cys
1               5                   10                  15

Gly Ala Gly Gly Val Val Met Ala Ile Ala Ser Val Thr Leu Val Thr
            20                  25                  30

Asp Thr Pro Gly Arg Val Leu Thr Gly Val Ala Ala Leu Gly Leu Ile
        35                  40                  45

Leu Phe Ala Ser Ala Thr Trp Arg Ala Arg Pro Arg Leu Ala Ile Thr
    50                  55                  60

Pro Asp Gly Leu Ala Ile Arg Gly Trp Phe Arg Thr Gln Leu Leu Arg
65                  70                  75                  80

His Ser Asn Ile Lys Ile Ile Arg Ile Asp Glu Phe Arg Arg Tyr Gly
                85                  90                  95

Arg Leu Val Arg Leu Leu Glu Ile Glu Thr Val Ser Gly Gly Leu Leu
            100                 105                 110

Ile Leu Ser Arg Trp Asp Leu Gly Thr Asp Pro Val Glu Val Leu Asp
        115                 120                 125

Ala Leu Thr Ala Ala Gly Tyr Ala Gly Arg Gly Gln Arg
    130                 135                 140
```

<210> SEQ ID NO 60
<211> LENGTH: 1245
<212> TYPE: DNA
<213> ORGANISM: artificial sequence
<220> FEATURE:
<223> OTHER INFORMATION: Rv1872c

<400> SEQUENCE: 60

```
atggccgtga acaggagggt gcccaggtg agggacctgg ccccctgct gcagttcaac    60
aggccccagt tcgacaccag caagaggagg ctgggcgccg ccctgaccat ccaggacctg    120
aggaggatcg ccaagaggag gacccccagg gccgccttcg actacgccga cggcggcgcc    180
gaggacgagc tgagcatcgc cagggccagg cagggcttca ggacatcga gttccacccc    240
accatcctga gggacgtgac caccgtgtgc gccggctgga acgtgctggg ccagcccacc    300
gtgctgccct tcggcatcgc ccccaccggc ttcaccaggc tgatgcacac cgagggcgag    360
atcgccggcg ccagggccgc cgccgccgcc ggcatcccct tcagcctgag caccctggcc    420
```

-continued

```
acctgcgcca tcgaggacct ggtgatcgcc gtgccccagg gcaggaagtg gttccagctg     480
tacatgtgga gggacaggga caggagcatg gccctggtga ggagggtggc cgccgccggc     540
ttcgacacca tgctggtgac cgtggacgtg cccgtggccg gcgccaggct gagggacgtg     600
aggaacggca tgagcatccc ccccgccctg accctgagga ccgtgctgga cgccatgggc     660 cacccaggt ggtggttcga cctgctgacc accgagcccc tggccttcgc cagcctggac      720
aggtggcccg gcaccgtggg cgagtacctg aacaccgtgt cgacccccag cctgaccttc     780
gacgacctgg cctggatcaa gagccagtgg cccggcaagc tggtggtgaa gggcatccag     840
accctggacg acgccagggc cgtggtggac aggggcgtgg acggcatcgt gctgagcaac     900
cacggcggca ggcagctgga cagggccccc gtgcccttcc acctgctgcc ccacgtggcc     960
agggagctgg gcaagcacac cgagatcctg gtggacaccg gcatcatgag cggcgccgac    1020
atcgtggccg ccatcgccct gggcgccagg tgcaccctga tcggcagggc ctacctgtac    1080
ggcctgatgg ccggcggcga ggccggcgtg aacagggcca tcgagatcct gcagaccggc    1140
gtgatcagga ccatgaggct gctgggcgtg acctgcctgg aggagctgag ccccaggcac    1200
gtgacccagc tgaggaggct gggccccatc ggcgccccca cctga                    1245
```

<210> SEQ ID NO 61
<211> LENGTH: 414
<212> TYPE: PRT
<213> ORGANISM: artificial sequence
<220> FEATURE:
<223> OTHER INFORMATION: Rv1872c

<400> SEQUENCE: 61

```
Met Ala Val Asn Arg Arg Val Pro Arg Val Arg Asp Leu Ala Pro Leu
1               5                   10                  15

Leu Gln Phe Asn Arg Pro Gln Phe Asp Thr Ser Lys Arg Arg Leu Gly
            20                  25                  30

Ala Ala Leu Thr Ile Gln Asp Leu Arg Arg Ile Ala Lys Arg Arg Thr
        35                  40                  45

Pro Arg Ala Ala Phe Asp Tyr Ala Asp Gly Gly Ala Glu Asp Glu Leu
    50                  55                  60

Ser Ile Ala Arg Ala Arg Gln Gly Phe Arg Asp Ile Glu Phe His Pro
65                  70                  75                  80

Thr Ile Leu Arg Asp Val Thr Thr Val Cys Ala Gly Trp Asn Val Leu
                85                  90                  95

Gly Gln Pro Thr Val Leu Pro Phe Gly Ile Ala Pro Thr Gly Phe Thr
            100                 105                 110

Arg Leu Met His Thr Glu Gly Glu Ile Ala Gly Ala Arg Ala Ala Ala
        115                 120                 125

Ala Ala Gly Ile Pro Phe Ser Leu Ser Thr Leu Ala Thr Cys Ala Ile
    130                 135                 140

Glu Asp Leu Val Ile Ala Val Pro Gln Gly Arg Lys Trp Phe Gln Leu
145                 150                 155                 160

Tyr Met Trp Arg Asp Arg Asp Arg Ser Met Ala Leu Val Arg Arg Val
                165                 170                 175

Ala Ala Ala Gly Phe Asp Thr Met Leu Val Thr Val Asp Val Pro Val
            180                 185                 190

Ala Gly Ala Arg Leu Arg Asp Val Arg Asn Gly Met Ser Ile Pro Pro
        195                 200                 205
```

Ala Leu Thr Leu Arg Thr Val Leu Asp Ala Met Gly His Pro Arg Trp
    210                 215                 220

Trp Phe Asp Leu Leu Thr Glu Pro Leu Ala Phe Ala Ser Leu Asp
225                 230                 235                 240

Arg Trp Pro Gly Thr Val Gly Glu Tyr Leu Asn Thr Val Phe Asp Pro
                245                 250                 255

Ser Leu Thr Phe Asp Asp Leu Ala Trp Ile Lys Ser Gln Trp Pro Gly
                260                 265                 270

Lys Leu Val Val Lys Gly Ile Gln Thr Leu Asp Asp Ala Arg Ala Val
                275                 280                 285

Val Asp Arg Gly Val Asp Gly Ile Val Leu Ser Asn His Gly Gly Arg
            290                 295                 300

Gln Leu Asp Arg Ala Pro Val Pro Phe His Leu Leu Pro His Val Ala
305                 310                 315                 320

Arg Glu Leu Gly Lys His Thr Glu Ile Leu Val Asp Thr Gly Ile Met
                325                 330                 335

Ser Gly Ala Asp Ile Val Ala Ala Ile Ala Leu Gly Ala Arg Cys Thr
                340                 345                 350

Leu Ile Gly Arg Ala Tyr Leu Tyr Gly Leu Met Ala Gly Gly Glu Ala
            355                 360                 365

Gly Val Asn Arg Ala Ile Glu Ile Leu Gln Thr Gly Val Ile Arg Thr
        370                 375                 380

Met Arg Leu Leu Gly Val Thr Cys Leu Glu Glu Leu Ser Pro Arg His
385                 390                 395                 400

Val Thr Gln Leu Arg Arg Leu Gly Pro Ile Gly Ala Pro Thr
                405                 410

<210> SEQ ID NO 62
<211> LENGTH: 789
<212> TYPE: DNA
<213> ORGANISM: artificial sequence
<220> FEATURE:
<223> OTHER INFORMATION: Rv0012

<400> SEQUENCE: 62

```
atgaggctga cccaccccac ccctgccc gagaacggcg agaccatgat cgacaggagg      60
aggagcgcct ggaggttcag cgtgcccctg tgtgcctgc tggccggcct gctgctggcc     120
gccacccacg gcgtgagcgg cggcaccgag atcaggagga gcgacgcccc caggctggtg    180
gacctggtga gagggcccca ggccagcgtg aacaggctgg ccaccgagag ggaggccctg    240
accaccagga tcgacagcgt gcacggcagg agcgtggaca ccgccctggc cgccatgcag    300
aggaggagcg ccaagctggc cggcgtggcc gccatgaacc ccgtgcacgg ccccggcctg    360
gtggtgaccc tgcaggacgc ccagagggac gccaacggca ggttccccag ggacgccagc    420
cccgacgacc tggtggtgca ccagcaggac atcgaggccg tgctgaacgc cctgtggaac    480
gccggcgccg aggccatcca gatgcaggac cagaggatca tcgccatgag catcgccagg    540
tgcgtgggca cacccctgct gctgaacggc aggacctaca gccccccta ccatcgcc      600
gccatcggcg acgccgccgc catgcaggcc gccctggccg ccgcccccct ggtgaccctg    660
tacaagcagt acgtggtgag gttcggcctg ggctactgcg aggaggtgca ccccgacctg    720
cagatcgtgg gctacgccga ccccgtgagg atgcacttcg cccagcccgc cggccccctg    780
gactactga                                                            789
```

-continued

```
<210> SEQ ID NO 63
<211> LENGTH: 262
<212> TYPE: PRT
<213> ORGANISM: artificial sequence
<220> FEATURE:
<223> OTHER INFORMATION: Rv0012

<400> SEQUENCE: 63

Met Arg Leu Thr His Pro Thr Pro Cys Pro Glu Asn Gly Glu Thr Met
1               5                   10                  15

Ile Asp Arg Arg Arg Ser Ala Trp Arg Phe Ser Val Pro Leu Val Cys
            20                  25                  30

Leu Leu Ala Gly Leu Leu Leu Ala Ala Thr His Gly Val Ser Gly Gly
        35                  40                  45

Thr Glu Ile Arg Arg Ser Asp Ala Pro Arg Leu Val Asp Leu Val Arg
    50                  55                  60

Arg Ala Gln Ala Ser Val Asn Arg Leu Ala Thr Glu Arg Glu Ala Leu
65                  70                  75                  80

Thr Thr Arg Ile Asp Ser Val His Gly Arg Ser Val Asp Thr Ala Leu
                85                  90                  95

Ala Ala Met Gln Arg Arg Ser Ala Lys Leu Ala Gly Val Ala Ala Met
            100                 105                 110

Asn Pro Val His Gly Pro Gly Leu Val Val Thr Leu Gln Asp Ala Gln
        115                 120                 125

Arg Asp Ala Asn Gly Arg Phe Pro Arg Asp Ala Ser Pro Asp Asp Leu
    130                 135                 140

Val Val His Gln Gln Asp Ile Glu Ala Val Leu Asn Ala Leu Trp Asn
145                 150                 155                 160

Ala Gly Ala Glu Ala Ile Gln Met Gln Asp Gln Arg Ile Ile Ala Met
                165                 170                 175

Ser Ile Ala Arg Cys Val Gly Asn Thr Leu Leu Asn Gly Arg Thr
            180                 185                 190

Tyr Ser Pro Pro Tyr Thr Ile Ala Ala Ile Gly Asp Ala Ala Ala Met
        195                 200                 205

Gln Ala Ala Leu Ala Ala Ala Pro Leu Val Thr Leu Tyr Lys Gln Tyr
    210                 215                 220

Val Val Arg Phe Gly Leu Gly Tyr Cys Glu Glu Val His Pro Asp Leu
225                 230                 235                 240

Gln Ile Val Gly Tyr Ala Asp Pro Val Arg Met His Phe Ala Gln Pro
                245                 250                 255

Ala Gly Pro Leu Asp Tyr
            260

<210> SEQ ID NO 64
<211> LENGTH: 657
<212> TYPE: DNA
<213> ORGANISM: artificial sequence
<220> FEATURE:
<223> OTHER INFORMATION: Rv0990c

<400> SEQUENCE: 64
gtggccgaga gcagcctgaa ccccagcctg gtgagcagga tcagcgcctt cctgaggccc     60
gactggacca ggaccgtgag ggccaggagg ttcgccgccg ccggcctggt gatgctggcc    120
ggcgtggccg ccctgaggag caaccccgag gacgacagga gcgaggtggt ggtggccgcc    180
cacgacctga ggcccggcac cgccctgacc ccggcgacg tgaggctgga gaagaggagc    240
gccaccaccc tgcccgacgg cagccaggcc gacctggacg ccgtggtggg cagcaccctg    300
```

```
gccagcccca ccaggagggg cgaggtgctg accgacgtga ggctgctggg cagcaggctg    360
gccgagagca ccgccggccc cgacgccagg atcgtgcccc tgcacctggc cgacagcgcc    420
ctggtggacc tggtgagggt gggcgacgtg gtggacgtgc tggccgcccc cgtgaccgac    480
agccccgccg ccctgaggct gctggccacc gacgccatcg tggtgctggt gagcgcccag    540
cagaaggccc aggccgccga cagcgacagg gtggtgctgg tggccctgcc cgccaggctg    600
gccaacaccg tggccggcgc cgccctgggc cagaccgtga ccctgaccct gcactga      657

<210> SEQ ID NO 65
<211> LENGTH: 218
<212> TYPE: PRT
<213> ORGANISM: artificial sequence
<220> FEATURE:
<223> OTHER INFORMATION: Rv0990c

<400> SEQUENCE: 65

Val Ala Glu Ser Ser Leu Asn Pro Ser Leu Val Ser Arg Ile Ser Ala
1               5                   10                  15

Phe Leu Arg Pro Asp Trp Thr Arg Thr Val Arg Ala Arg Arg Phe Ala
            20                  25                  30

Ala Ala Gly Leu Val Met Leu Ala Gly Val Ala Ala Leu Arg Ser Asn
        35                  40                  45

Pro Glu Asp Asp Arg Ser Glu Val Val Ala Ala His Asp Leu Arg
    50                  55                  60

Pro Gly Thr Ala Leu Thr Pro Gly Asp Val Arg Leu Glu Lys Arg Ser
65                  70                  75                  80

Ala Thr Thr Leu Pro Asp Gly Ser Gln Ala Asp Leu Asp Ala Val Val
                85                  90                  95

Gly Ser Thr Leu Ala Ser Pro Thr Arg Arg Gly Glu Val Leu Thr Asp
            100                 105                 110

Val Arg Leu Leu Gly Ser Arg Leu Ala Glu Ser Thr Ala Gly Pro Asp
        115                 120                 125

Ala Arg Ile Val Pro Leu His Leu Ala Asp Ser Ala Leu Val Asp Leu
    130                 135                 140

Val Arg Val Gly Asp Val Val Asp Val Leu Ala Ala Pro Val Thr Asp
145                 150                 155                 160

Ser Pro Ala Ala Leu Arg Leu Leu Ala Thr Asp Ala Ile Val Val Leu
                165                 170                 175

Val Ser Ala Gln Gln Lys Ala Gln Ala Ala Asp Ser Asp Arg Val Val
            180                 185                 190

Leu Val Ala Leu Pro Ala Arg Leu Ala Asn Thr Val Ala Gly Ala Ala
        195                 200                 205

Leu Gly Gln Thr Val Thr Leu Thr Leu His
    210                 215

<210> SEQ ID NO 66
<211> LENGTH: 612
<212> TYPE: DNA
<213> ORGANISM: artificial sequence
<220> FEATURE:
<223> OTHER INFORMATION: Rv0995

<400> SEQUENCE: 66
atggccgtgg ccccctgag ggtgagcgcc ggcgtgatca ggctgaggcc cgtgaggatg    60
agggacggcg tgcactggag caggatcagg ctggccgaca gggcccacct ggagccctgg    120
```

```
gagcccagcg ccgacggcga gtggaccgtg aggcacaccg tggccgcctg gcccgccgtg      180
tgcagcggcc tgaggagcga ggccaggaac ggcaggatgc tgccctacgt gatcgagctg      240
gacggccagt tctgcggcca gctgaccatc ggcaacgtga cccacggcgc cctgaggagc      300
gcctggatcg gctactgggt gcccagcgcc gccaccggcg gcggcgtggc caccggcgcc      360
ctggccctgg gcctggacca ctgcttcggc cccgtgatgc tgcacagggt ggaggccacc      420
gtgaggcccg agaacgccgc cagcagggcc gtgctggcca aggtgggctt cagggaggag      480
ggcctgctga ggaggtacct ggaggtggac agggcctgga gggaccacct gctgatggcc      540
atcaccgtgg aggaggtgta cggcagcgtg ccagcaccc tggtgagggc cggccacgcc      600
agctggccct ga                                                          612
```

<210> SEQ ID NO 67
<211> LENGTH: 203
<212> TYPE: PRT
<213> ORGANISM: artificial sequence
<220> FEATURE:
<223> OTHER INFORMATION: Rv0995

<400> SEQUENCE: 67

```
Met Ala Val Gly Pro Leu Arg Val Ser Ala Gly Val Ile Arg Leu Arg
1               5                   10                  15
Pro Val Arg Met Arg Asp Gly Val His Trp Ser Arg Ile Arg Leu Ala
            20                  25                  30
Asp Arg Ala His Leu Glu Pro Trp Glu Pro Ser Ala Asp Gly Glu Trp
        35                  40                  45
Thr Val Arg His Thr Val Ala Ala Trp Pro Ala Val Cys Ser Gly Leu
    50                  55                  60
Arg Ser Glu Ala Arg Asn Gly Arg Met Leu Pro Tyr Val Ile Glu Leu
65                  70                  75                  80
Asp Gly Gln Phe Cys Gly Gln Leu Thr Ile Gly Asn Val Thr His Gly
                85                  90                  95
Ala Leu Arg Ser Ala Trp Ile Gly Tyr Trp Val Pro Ser Ala Ala Thr
            100                 105                 110
Gly Gly Gly Val Ala Thr Gly Ala Leu Ala Leu Gly Leu Asp His Cys
        115                 120                 125
Phe Gly Pro Val Met Leu His Arg Val Glu Ala Thr Val Arg Pro Glu
    130                 135                 140
Asn Ala Ala Ser Arg Ala Val Leu Ala Lys Val Gly Phe Arg Glu Glu
145                 150                 155                 160
Gly Leu Leu Arg Arg Tyr Leu Glu Val Asp Arg Ala Trp Arg Asp His
                165                 170                 175
Leu Leu Met Ala Ile Thr Val Glu Glu Val Tyr Gly Ser Val Ala Ser
            180                 185                 190
Thr Leu Val Arg Ala Gly His Ala Ser Trp Pro
        195                 200
```

<210> SEQ ID NO 68
<211> LENGTH: 2190
<212> TYPE: DNA
<213> ORGANISM: artificial sequence
<220> FEATURE:
<223> OTHER INFORMATION: Rv2719c-Rv0010c-Rv1872c fusion protein

<400> SEQUENCE: 68

```
atgaccccg tgaggccccc ccacaccccc gacccctga acctgagggg ccccctggac      60
ggccccaggt ggaggagggc cgagcccgcc cagagcagga ggcccggcag gagcaggccc     120
ggcggcgccc ccctgaggta ccacaggacc ggcgtgggca tgagcaggac cggccacggc     180
agcaggcccg tgcccccgc caccaccgtg ggcctggccc tgctggccgc cgccatcacc      240
ctgtggctgg gcctggtggc ccagttcggc cagatgatca ccggcggcag cgccgacggc     300
agcgccgaca gcaccggcag ggtgcccgac aggctggccg tggtgagggt ggagaccggc     360
gagagcctgt acgacgtggc cgtgagggtg ccccccaacg cccccaccag gcaggtggcc     420
gacaggatca gggagctgaa cggcctgcag accccgccc tggccgtggg ccagaccctg      480
atcgccccg tgggcatgca gcagaccgcc tgggccccca ggaccagcgg catcgccggc      540
tgcggcgccg cggcgtggt gatggccatc gccagcgtga ccctggtgac cgacaccccc      600
ggcagggtgc tgaccggcgt ggccgccctg ggcctgatcc tgttcgccag cgccaccctgg    660
agggccaggc ccaggctggc catcacccc gacggcctgg ccatcagggg ctggttcagg      720
acccagctgc tgaggcacag caacatcaag atcatcagga tcgacgagtt caggaggtac     780
ggcaggctgg tgaggctgct ggagatcgag accgtgagcg gcggcctgct gatcctgagc     840
aggtgggacc tgggcaccga cccgtggag gtgctggacg ccctgaccgc cgccggctac      900
gccggcaggg gccagaggat ggccgtgaac aggagggtgc ccagggtgag ggacctggcc     960
cccctgctgc agttcaacag gccccagttc gacaccagca agaggaggct gggcgccgcc    1020
ctgaccatcc aggacctgag gaggatcgcc aagaggagga cccccagggc cgccttcgac    1080
tacgccgacg cgggcgccga ggacgagctg agcatcgcca gggccaggca gggcttcagg    1140
gacatcgagt tccacccca catcctgagg gacgtgacca ccgtgtgcgc cggctggaac    1200
gtgctgggcc agcccaccgt gctgcccttc ggcatcgccc ccaccggctt caccaggctg    1260
atgcacaccg agggcgagat cgccggcgcc agggccgccg ccgccgccgg catcccctcc    1320
agcctgagca ccctgccac ctgcgccatc gaggacctgg tgatcgccgt gcccagggc     1380
aggaagtggt tccagctgta catgtggagg gacaggggaca ggagcatggc cctggtgagg    1440
agggtggccg ccgccggctt cgacaccatg ctggtgaccg tggacgtgcc cgtggccggc    1500
gccaggctga gggacgtgag gaacggcatg agcatccccc ccgccctgac cctgaggacc    1560
gtgctggacg ccatgggcca cccccaggtgg tggttcgacc tgctgaccac cgagcccctg    1620
gccttcgcca gctggacag gtggcccggc accgtgggcg agtacctgaa caccgtgttc    1680
gaccccagcc tgaccttcga cgacctggcc tggatcaaga gcagtggcc cggcaagctg    1740
gtggtgaagg gcatccagac cctggacgac gccagggcc tggtggacag gggcgtggac    1800
ggcatcgtgc tgagcaacca cggcggcagg cagctggaca gggccccgt gcccttccac    1860
ctgctgcccc acgtggccag ggagctgggc aagcacaccg agatcctggt ggacaccggc    1920
atcatgagcg gcgccgacat cgtggccgcc atcgccctgg gcgccaggtg cacccctgatc    1980
ggcagggcct acctgtacgg cctgatggcc ggcggcgagg ccggcgtgaa cagggccatc    2040
gagatcctgc agaccggcgt gatcaggacc atgaggctgc tgggcgtgac ctgcctggag    2100
gagctgagcc ccaggcacgt gacccagctg aggaggctgg ccccatcgg cgcccccacc    2160
taccccctacg acgtgcccga ctacgcctga                                    2190
```

<210> SEQ ID NO 69

<211> LENGTH: 729
<212> TYPE: PRT
<213> ORGANISM: artificial sequence
<220> FEATURE:
<223> OTHER INFORMATION: Rv2719c-Rv0010c-Rv1872c fusion protein

<400> SEQUENCE: 69

```
Met Thr Pro Val Arg Pro Pro His Thr Pro Asp Pro Leu Asn Leu Arg
1               5                   10                  15

Gly Pro Leu Asp Gly Pro Arg Trp Arg Ala Glu Pro Ala Gln Ser
            20                  25                  30

Arg Arg Pro Gly Arg Ser Arg Pro Gly Gly Ala Pro Leu Arg Tyr His
        35                  40                  45

Arg Thr Gly Val Gly Met Ser Arg Thr Gly His Gly Ser Arg Pro Val
50                  55                  60

Pro Pro Ala Thr Thr Val Gly Leu Ala Leu Ala Ala Ala Ile Thr
65                  70                  75                  80

Leu Trp Leu Gly Leu Val Ala Gln Phe Gly Gln Met Ile Thr Gly Gly
                85                  90                  95

Ser Ala Asp Gly Ser Ala Asp Ser Thr Gly Arg Val Pro Asp Arg Leu
            100                 105                 110

Ala Val Val Arg Val Glu Thr Gly Glu Ser Leu Tyr Asp Val Ala Val
        115                 120                 125

Arg Val Ala Pro Asn Ala Pro Thr Arg Gln Val Ala Asp Arg Ile Arg
130                 135                 140

Glu Leu Asn Gly Leu Gln Thr Pro Ala Leu Ala Val Gly Gln Thr Leu
145                 150                 155                 160

Ile Ala Pro Val Gly Met Gln Gln Thr Ala Trp Ala Pro Arg Thr Ser
                165                 170                 175

Gly Ile Ala Gly Cys Gly Ala Gly Gly Val Val Met Ala Ile Ala Ser
            180                 185                 190

Val Thr Leu Val Thr Asp Thr Pro Gly Arg Val Leu Thr Gly Val Ala
        195                 200                 205

Ala Leu Gly Leu Ile Leu Phe Ala Ser Ala Thr Trp Arg Ala Arg Pro
210                 215                 220

Arg Leu Ala Ile Thr Pro Asp Gly Leu Ala Ile Arg Gly Trp Phe Arg
225                 230                 235                 240

Thr Gln Leu Leu Arg His Ser Asn Ile Lys Ile Ile Arg Ile Asp Glu
                245                 250                 255

Phe Arg Arg Tyr Gly Arg Leu Val Arg Leu Leu Glu Ile Glu Thr Val
            260                 265                 270

Ser Gly Gly Leu Leu Ile Leu Ser Arg Trp Asp Leu Gly Thr Asp Pro
        275                 280                 285

Val Glu Val Leu Asp Ala Leu Thr Ala Ala Gly Tyr Ala Gly Arg Gly
290                 295                 300

Gln Arg Met Ala Val Asn Arg Val Pro Arg Val Arg Asp Leu Ala
305                 310                 315                 320

Pro Leu Leu Gln Phe Asn Arg Pro Gln Phe Asp Thr Ser Lys Arg Arg
                325                 330                 335

Leu Gly Ala Ala Leu Thr Ile Gln Asp Leu Arg Arg Ile Ala Lys Arg
            340                 345                 350

Arg Thr Pro Arg Ala Ala Phe Asp Tyr Ala Asp Gly Gly Ala Glu Asp
        355                 360                 365

Glu Leu Ser Ile Ala Arg Ala Arg Gln Gly Phe Arg Asp Ile Glu Phe
370                 375                 380
```

His Pro Thr Ile Leu Arg Asp Val Thr Thr Val Cys Ala Gly Trp Asn
385                 390                 395                 400

Val Leu Gly Gln Pro Thr Val Leu Pro Phe Gly Ile Ala Pro Thr Gly
            405                 410                 415

Phe Thr Arg Leu Met His Thr Glu Gly Glu Ile Ala Gly Ala Arg Ala
        420                 425                 430

Ala Ala Ala Gly Ile Pro Phe Ser Leu Ser Thr Leu Ala Thr Cys
    435                 440                 445

Ala Ile Glu Asp Leu Val Ile Ala Val Pro Gln Gly Arg Lys Trp Phe
450                 455                 460

Gln Leu Tyr Met Trp Arg Asp Arg Asp Arg Ser Met Ala Leu Val Arg
465                 470                 475                 480

Arg Val Ala Ala Gly Phe Asp Thr Met Leu Val Thr Val Asp Val
            485                 490                 495

Pro Val Ala Gly Ala Arg Leu Arg Asp Val Arg Asn Gly Met Ser Ile
            500                 505                 510

Pro Pro Ala Leu Thr Leu Arg Thr Val Leu Asp Ala Met Gly His Pro
            515                 520                 525

Arg Trp Trp Phe Asp Leu Leu Thr Thr Glu Pro Leu Ala Phe Ala Ser
530                 535                 540

Leu Asp Arg Trp Pro Gly Thr Val Gly Glu Tyr Leu Asn Thr Val Phe
545                 550                 555                 560

Asp Pro Ser Leu Thr Phe Asp Leu Ala Trp Ile Lys Ser Gln Trp
            565                 570                 575

Pro Gly Lys Leu Val Val Lys Gly Ile Gln Thr Leu Asp Asp Ala Arg
            580                 585                 590

Ala Val Val Asp Arg Gly Val Asp Gly Ile Val Leu Ser Asn His Gly
            595                 600                 605

Gly Arg Gln Leu Asp Arg Ala Pro Val Pro Phe His Leu Pro His
    610                 615                 620

Val Ala Arg Glu Leu Gly Lys His Thr Glu Ile Leu Val Asp Thr Gly
625                 630                 635                 640

Ile Met Ser Gly Ala Asp Ile Val Ala Ala Ile Ala Leu Gly Ala Arg
            645                 650                 655

Cys Thr Leu Ile Gly Arg Ala Tyr Leu Tyr Gly Leu Met Ala Gly Gly
            660                 665                 670

Glu Ala Gly Val Asn Arg Ala Ile Glu Ile Leu Gln Thr Gly Val Ile
            675                 680                 685

Arg Thr Met Arg Leu Leu Gly Val Thr Cys Leu Glu Glu Leu Ser Pro
        690                 695                 700

Arg His Val Thr Gln Leu Arg Arg Leu Gly Pro Ile Gly Ala Pro Thr
705                 710                 715                 720

Tyr Pro Tyr Asp Val Pro Asp Tyr Ala
                725

<210> SEQ ID NO 70
<211> LENGTH: 2079
<212> TYPE: DNA
<213> ORGANISM: artificial sequence
<220> FEATURE:
<223> OTHER INFORMATION: Rv0012-Rv0990c-Rv0995 fusion protein

<400> SEQUENCE: 70

```
atgaggctga cccaccccac cccctgcccc gagaacggcg agaccatgat cgacaggagg     60
aggagcgcct ggaggttcag cgtgcccctg gtgtgcctgc tggccggcct gctgctggcc    120
gccacccacg gcgtgagcgg cggcaccgag atcaggagga gcgacgcccc caggctggtg    180
gacctggtga ggagggccca ggccagcgtg aacaggctgg ccaccgagag ggaggccctg    240
accaccagga tcgacagcgt gcacggcagg agcgtggaca ccgccctggc cgccatgcag    300
aggaggagcg ccaagctggc cggcgtggcc gccatgaacc ccgtgcacgg ccccggcctg    360
gtggtgaccc tgcaggacgc ccagagggac gccaacggca ggttccccag ggacgccagc    420
cccgacgacc tggtggtgca ccagcaggac atcgaggccg tgctgaacgc cctgtggaac    480
gccgcgccg aggccatcca gatgcaggac cagaggatca tcgccatgag catcgccagg    540
tgcgtgggca caccctgct gctgaacggc aggacctaca gccccccta ccatcgcc       600
gccatcggcg acgccgccgc catgcaggcc gccctggccg ccgcccccct ggtgaccctg    660
tacaagcagt acgtggtgag gttcggcctg ggctactgcg aggaggtgca ccccgacctg    720
cagatcgtgg gctacgccga ccccgtgagg atgcacttcg cccagcccgc cggccccctg    780
gactacgtgg ccgagagcag cctgaacccc agcctggtga gcaggatcag cgccttcctg    840
aggcccgact ggaccaggac cgtgagggcc aggaggttcg ccgccgccgg cctggtgatg    900
ctggccggcg tggccgccct gaggagcaac cccgaggacg acaggagcga ggtggtggtg    960
gccgcccacg acctgaggcc cggcaccgcc ctgaccccccg cgacgtgag gctggagaag   1020
aggagcgcca ccaccctgcc cgacggcagc caggccgacc tggacgccgt ggtgggcagc   1080
accctggcca gccccaccag gaggggcgag gtgctgaccg acgtgaggct gctgggcagc   1140
aggctggccg agagcaccgc cggccccgac gccaggatcg tgccctgca cctggccgac   1200
agcgccctgg tggacctggt gagggtgggc gacgtggtgg acgtgctggc cgcccccgtg   1260
accgacagcc ccgccgccct gaggctgctg gccaccgacg ccatcgtggt gctggtgagc   1320
gcccagcaga aggcccaggc cgccgacagc gacagggtgg tgctggtggc cctgcccgcc   1380
aggctggcca acaccgtggc cggcgccgcc ctggccagca ccgtgaccct gaccctgcac   1440
atggccgtgg cccccctgag ggtgagcgcc ggcgtgatca ggctgaggcc cgtgaggatg   1500
agggacggcg tgcactggag caggatcagg ctggccgaca gggcccacct ggagccctgg   1560
gagcccagcg ccgacggcga gtggaccgtg aggcacaccg tggccgcctg gccgccgtg   1620
tgcagcggcc tgaggagcga ggccaggaac ggcaggatgc tgccctacgt gatcgagctg   1680
gacggccagt tctgcggcca gctgaccatc ggcaacgtga cccacggcgc cctgaggagc   1740
gcctggatcg gctactgggt gcccagcgcc gccaccggcg gcgcgtggc caccggcgcc   1800
ctggccctgg gcctggacca ctgcttcggc cccgtgatgc tgcacagggt ggaggccacc   1860
gtgaggcccg agaacgccgc cagcagggcc gtgctggcca agtgggcttc agggaggag   1920
ggcctgctga ggaggtacct ggaggtggac agggcctgga gggaccacct gctgatggcc   1980
atcaccgtgg aggaggtgta cggcagcgtg gccagcaccc tggtgagggc cggccacgcc   2040
agctggccct accctacga cgtgcccgac tacgcctga                          2079
```

<210> SEQ ID NO 71
<211> LENGTH: 692
<212> TYPE: PRT
<213> ORGANISM: artificial sequence
<220> FEATURE:

<223> OTHER INFORMATION: Rv0012-Rv0990c-Rv0995 fusion protein

<400> SEQUENCE: 71

```
Met Arg Leu Thr His Pro Thr Pro Cys Pro Glu Asn Gly Glu Thr Met
1               5                   10                  15
Ile Asp Arg Arg Ser Ala Trp Arg Phe Ser Val Pro Leu Val Cys
            20                  25                  30
Leu Leu Ala Gly Leu Leu Leu Ala Ala Thr His Gly Val Ser Gly Gly
                35                  40                  45
Thr Glu Ile Arg Arg Ser Asp Ala Pro Arg Leu Val Asp Leu Val Arg
        50                  55                  60
Arg Ala Gln Ala Ser Val Asn Arg Leu Ala Thr Glu Arg Glu Ala Leu
65                  70                  75                  80
Thr Thr Arg Ile Asp Ser Val His Gly Arg Ser Val Asp Thr Ala Leu
                85                  90                  95
Ala Ala Met Gln Arg Arg Ser Ala Lys Leu Ala Gly Val Ala Ala Met
            100                 105                 110
Asn Pro Val His Gly Pro Gly Leu Val Val Thr Leu Gln Asp Ala Gln
            115                 120                 125
Arg Asp Ala Asn Gly Arg Phe Pro Arg Asp Ala Ser Pro Asp Asp Leu
130                 135                 140
Val Val His Gln Gln Asp Ile Glu Ala Val Leu Asn Ala Leu Trp Asn
145                 150                 155                 160
Ala Gly Ala Glu Ala Ile Gln Met Gln Asp Gln Arg Ile Ile Ala Met
                165                 170                 175
Ser Ile Ala Arg Cys Val Gly Asn Thr Leu Leu Leu Asn Gly Arg Thr
            180                 185                 190
Tyr Ser Pro Pro Tyr Thr Ile Ala Ala Ile Gly Asp Ala Ala Ala Met
        195                 200                 205
Gln Ala Ala Leu Ala Ala Ala Pro Leu Val Thr Leu Tyr Lys Gln Tyr
210                 215                 220
Val Val Arg Phe Gly Leu Gly Tyr Cys Glu Glu Val His Pro Asp Leu
225                 230                 235                 240
Gln Ile Val Gly Tyr Ala Asp Pro Val Arg Met His Phe Ala Gln Pro
                245                 250                 255
Ala Gly Pro Leu Asp Tyr Val Ala Glu Ser Ser Leu Asn Pro Ser Leu
            260                 265                 270
Val Ser Arg Ile Ser Ala Phe Leu Arg Pro Asp Trp Thr Arg Thr Val
        275                 280                 285
Arg Ala Arg Arg Phe Ala Ala Ala Gly Leu Val Met Leu Ala Gly Val
290                 295                 300
Ala Ala Leu Arg Ser Asn Pro Glu Asp Arg Ser Glu Val Val Val
305                 310                 315                 320
Ala Ala His Asp Leu Arg Pro Gly Thr Ala Leu Thr Pro Gly Asp Val
                325                 330                 335
Arg Leu Glu Lys Arg Ser Ala Thr Thr Leu Pro Asp Gly Ser Gln Ala
            340                 345                 350
Asp Leu Asp Ala Val Val Gly Ser Thr Leu Ala Ser Pro Thr Arg Arg
        355                 360                 365
Gly Glu Val Leu Thr Asp Val Arg Leu Leu Gly Ser Arg Leu Ala Glu
    370                 375                 380
Ser Thr Ala Gly Pro Asp Ala Arg Ile Val Pro Leu His Leu Ala Asp
385                 390                 395                 400
```

```
Ser Ala Leu Val Asp Leu Val Arg Val Gly Asp Val Val Asp Val Leu
                405                 410                 415
Ala Ala Pro Val Thr Asp Ser Pro Ala Ala Leu Arg Leu Leu Ala Thr
            420                 425                 430
Asp Ala Ile Val Val Leu Val Ser Ala Gln Gln Lys Ala Gln Ala Ala
            435                 440                 445
Asp Ser Asp Arg Val Val Leu Val Ala Leu Pro Ala Arg Leu Ala Asn
    450                 455                 460
Thr Val Ala Gly Ala Ala Leu Gly Gln Thr Val Thr Leu Thr Leu His
465                 470                 475                 480
Met Ala Val Gly Pro Leu Arg Val Ser Ala Gly Val Ile Arg Leu Arg
                485                 490                 495
Pro Val Arg Met Arg Asp Gly Val His Trp Ser Arg Ile Arg Leu Ala
                500                 505                 510
Asp Arg Ala His Leu Glu Pro Trp Glu Pro Ser Ala Asp Gly Glu Trp
            515                 520                 525
Thr Val Arg His Thr Val Ala Ala Trp Pro Ala Val Cys Ser Gly Leu
    530                 535                 540
Arg Ser Glu Ala Arg Asn Gly Arg Met Leu Pro Tyr Val Ile Glu Leu
545                 550                 555                 560
Asp Gly Gln Phe Cys Gly Gln Leu Thr Ile Gly Asn Val Thr His Gly
                565                 570                 575
Ala Leu Arg Ser Ala Trp Ile Gly Tyr Trp Val Pro Ser Ala Ala Thr
                580                 585                 590
Gly Gly Gly Val Ala Thr Gly Ala Leu Ala Leu Gly Leu Asp His Cys
            595                 600                 605
Phe Gly Pro Val Met Leu His Arg Val Glu Ala Thr Val Arg Pro Glu
    610                 615                 620
Asn Ala Ala Ser Arg Ala Val Leu Ala Lys Val Gly Phe Arg Glu Glu
625                 630                 635                 640
Gly Leu Leu Arg Arg Tyr Leu Glu Val Asp Arg Ala Trp Arg Asp His
                645                 650                 655
Leu Leu Met Ala Ile Thr Val Glu Glu Val Tyr Gly Ser Val Ala Ser
                660                 665                 670
Thr Leu Val Arg Ala Gly His Ala Ser Trp Pro Tyr Pro Tyr Asp Val
            675                 680                 685
Pro Asp Tyr Ala
690
```

TUBERCULOSIS ANTIGEN CASSETTES

REFERENCE TO SEQUENCE LISTING

This application includes a Sequence Listing submitted electronically as a text file named 190151.01801US.SEQ, created on Apr. 15, 2020, with a size of 110 kilobytes. The Sequence Listing is incorporated herein by reference.

FIELD

The present disclosure is directed, in part, to fusion proteins comprising *Mycobacterium tuberculosis* (Mtb) antigens, nucleic acid molecules encoding the same, vectors comprising nucleic acid molecules, compositions comprising the same, and methods of eliciting an immune response against tuberculosis.

BACKGROUND

Tuberculosis (TB) is a global health problem resulting in 8 million new cases and 2 million deaths each year. The emergence of multi-drug and totally-drug resistant strains of TB only makes this problem more severe. The life cycle of Mtb has 3 stages. In the acute phase following initial infection the bacteria replicate in the host and virulence factors are expressed, leading to the generation of an immune response by the host. As the immune response begins to control the infection, the Mtb enters a latent, asymptomatic state in which the bacteria become non-replicating and are encased in granulomas. The bacterium can persist in this latent state in infected individuals for many years, making diagnosis and treatment of disease difficult. In some cases, the bacteria are reactivated and begin replicating again, leading back to the disease state. Reactivation can occur for numerous reasons, including immune suppression caused by diseases such as HIV, treatments such as chemotherapy, or the weakening of the immune system due to aging. An estimated 2 billion people are latently infected with Mtb worldwide, and reactivation of latent Mtb accounts for most new cases of active TB disease. Reactivation is associated with inflammation, necrosis and cavitation of the lung, a process that results in draining of the lesions into the bronchus. Aerosols generated when individuals with bronchial lesions cough causes dissemination of the Mtb organism to uninfected, susceptible persons, and the transmission cycle is thus maintained.

The only currently available vaccine against TB, *Mycobacterium bovis* (Bacille Calmette-Guérin) (BCG), was first introduced in 1921. BCG has been widely utilized and while studies show that for some purposes BCG is effective (e.g., against disseminated TB), it is known to be ineffective with respect to preventing the development, persistence and reactivation of latent TB. There is an ongoing need to develop improved, more effective vaccines against TB. In particular, there is a need to develop vaccines that provide protection against the development, maintenance and/or reactivation of latent tuberculosis infection. With the availability of the entire genomic sequence of Mtb, and the tools for bioinformatic and experimental analysis of Mtb antigens, many new potential Mtb vaccine candidates have been identified in recent years. These include antigens that are involved in acute infection, maintenance of latency, or reactivation of Mtb. There are a range of delivery strategies in clinical development that are comprised of combinations of these and other antigens that have been tested in animal models and are currently or will soon be in clinical trials.

While vaccines are often effective to immunize individuals prophylactically or therapeutically against pathogen infection or human diseases, there is a need for improved vaccines. There is also a need for compositions and methods that produce an enhanced immune response. Likewise, while some immunotherapeutics are useful to modulate immune response in a patient, there remains a need for improved immunotherapeutic compositions and methods.

SUMMARY

The present disclosure describes antigen cassettes (and specified variants) that can be used to create tuberculosis vaccines comprising specified *Mycobacterium tuberculosis* (Mtb) antigens. The disclosure also describes the strategic combination of antigens which are incorporated into a variety of delivery platforms in such a way as to provide pathways to a matrix of matched combinations of antigen delivery to obtain an optimized immune response. The subject matter described herein can be used as a prophylactic or therapeutic TB vaccine. Specific selection of antigens for inclusion into a usable cassette was based on a number of additional parameters including, for example, a thorough review of the literature, expression data, responses by human T cells, inclusion of human immunogenic regions, mouse protection studies, and conservation in sequence across most strains of TB with full genome sequences (or lack thereof for the Variable antigens).

The constructs described herein can be integrated into several delivery platforms that include the following classes (but not exhaustive) of representative delivery platforms: 1) viral vector delivery systems, 2) recombinant BCG, 3) recombinant purified protein fusions, 4) DNA plasmid vector systems, and 5) RNA vector systems. These delivery platforms can be used either in a single platform alone or in combinations as matched antigen prime-boost approaches. In addition, the use of these antigens in a single rBCG vector system, which is envisioned to be used as an antigen matched prime for a boost with any of the modalities above, including protein, viral vectors, nucleic acids, or others.

The present disclosure provides fusion proteins that comprise at least two PE Mtb antigens, at least two PPE Mtb antigens, at least two ESX Mtb antigens, or at least two variable Mtb antigens.

The present disclosure also provides nucleic acid molecules encoding fusion proteins that comprise at least two PE Mtb antigens, at least two PPE Mtb antigens, at least two ESX Mtb antigens, or at least two variable Mtb antigens.

The present disclosure also provides: compositions comprising the fusion proteins and a pharmaceutically acceptable carrier; vectors encoding the fusion proteins; compositions comprising the vectors and a pharmaceutically acceptable carrier; cells comprising the vectors; compositions comprising the cells and a pharmaceutically acceptable carrier.

The present disclosure also provides compositions that comprise at least two PE Mtb antigens, at least two PPE Mtb antigens, at least two ESX Mtb antigens, or at least two variable Mtb antigens, and a pharmaceutically acceptable carrier.

The present disclosure also provides compositions that comprise at least two Mtb antigens, wherein the composition comprises at least one nucleic acid molecule encoding at least one of the Mtb antigens, and a pharmaceutically acceptable carrier.

The present disclosure also provides methods of eliciting an immune response against *Mycobacterium tuberculosis* in a mammal comprising administering to the mammal an immunologically sufficient amount of one or more fusion proteins described herein.

The present disclosure also provides methods of eliciting an immune response against *Mycobacterium tuberculosis* in a mammal comprising administering to the mammal an immunologically sufficient amount of a composition comprising one or more fusion proteins described herein, and a pharmaceutically acceptable carrier.

The present disclosure also provides methods of eliciting an immune response against *Mycobacterium tuberculosis* in a mammal comprising administering to the mammal an immunologically sufficient amount of a composition comprising one or more fusion proteins described herein, and a pharmaceutically acceptable carrier, wherein the composition comprises at least one nucleic acid molecule encoding at least one of the Mtb antigens.

The present disclosure also provides any one or more of the fusion proteins described herein for use in the preparation of a medicament for treating or preventing a *Mycobacterium tuberculosis* infection.

The present disclosure also provides any one or more of the fusion proteins described herein for use in treating or preventing a *Mycobacterium tuberculosis* infection.

The present disclosure also provides use of any one or more of the fusion proteins described herein in the preparation of a medicament for treating or preventing a *Mycobacterium tuberculosis* infection.

The present disclosure also provides use of any one or more of the fusion proteins described herein in treating or preventing a *Mycobacterium tuberculosis* infection.

The present disclosure also provides compositions for use in the preparation of a medicament for treating or preventing a *Mycobacterium tuberculosis* infection, wherein the composition comprises any one or more of the fusion proteins described herein, and a pharmaceutically acceptable carrier.

The present disclosure also provides any one or more of the compositions described herein for use in treating or preventing a *Mycobacterium tuberculosis* infection, and a pharmaceutically acceptable carrier.

The present disclosure also provides any one or more of the compositions described herein in the preparation of a medicament for treating or preventing a *Mycobacterium tuberculosis* infection, and a pharmaceutically acceptable carrier.

The present disclosure also provides use of any one or more of the compositions described herein in treating or preventing a *Mycobacterium tuberculosis* infection, and a pharmaceutically acceptable carrier.

The present disclosure also provides any one or more of the compositions described herein for use in the preparation of a medicament for treating or preventing a *Mycobacterium tuberculosis* infection, and a pharmaceutically acceptable carrier; wherein the composition comprises at least one nucleic acid molecule encoding at least one of the Mtb antigens.

The present disclosure also provides any one or more of the compositions described herein for use in treating or preventing a *Mycobacterium tuberculosis* infection, and a pharmaceutically acceptable carrier, wherein the composition comprises at least one nucleic acid molecule encoding at least one of the Mtb antigens.

The present disclosure also provides use of any one or more of the compositions described herein in the preparation of a medicament for treating or preventing a *Mycobacterium tuberculosis* infection, and a pharmaceutically acceptable carrier, wherein the composition comprises at least one nucleic acid molecule encoding at least one of the Mtb antigens.

The present disclosure also provides use of any one or more of the compositions described herein in treating or preventing a *Mycobacterium tuberculosis* infection, and a pharmaceutically acceptable carrier, wherein the composition comprises at least one nucleic acid molecule encoding at least one of the Mtb antigens.

The present disclosure also provides fusion proteins, compositions, cells, vectors, methods, and uses, as described herein, substantially as described herein.

DESCRIPTION OF EMBODIMENTS

The terminology used herein is for the purpose of describing particular embodiments only and is not intended to be limiting.

As used herein, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

As used herein, "adjuvant" means any molecule added to any composition described herein to enhance the immunogenicity of the Mtb antigens.

As used herein, "coding sequence" or "encoding nucleic acid" means the nucleic acids (RNA or DNA molecule) that comprise a nucleotide sequence which encodes an Mtb antigen. The coding sequence can further include initiation and termination signals operably linked to regulatory elements including a promoter and polyadenylation signal capable of directing expression in the cells of an individual or mammal to which the nucleic acid is administered.

As used herein, "consensus" or "consensus sequence" means a polypeptide sequence based on analysis of an alignment of multiple subtypes of a particular Mtb antigen. Nucleic acid sequences that encode a consensus polypeptide sequence can be prepared. Vaccines comprising Mtb antigens that comprise consensus sequences and/or nucleic acid molecules that encode such antigens can be used to induce broad immunity against multiple subtypes or serotypes of a particular antigen.

As used herein, "electroporation" means the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

As used herein, "fragment" with respect to nucleic acid sequences, means a nucleic acid sequence or a portion thereof, that encodes a portion of an Mtb antigen capable of eliciting an immune response in a mammal that cross reacts with a full length wild type Mtb antigen. The fragments can be DNA fragments selected from at least one of the various nucleotide sequences that encode protein fragments set forth below.

As used herein, "fragment" or "immunogenic fragment" with respect to polypeptide sequences, means a portion of an Mtb antigen capable of eliciting an immune response in a mammal that cross reacts with a full length wild type strain Mtb antigen. Fragments of consensus or wild type Mtb antigens can comprise at least 10%, at least 20%, at least 30%, at least 40%, at least 50%, at least 60%, at least 70%, at least 80%, at least 90% or at least 95% of a consensus or wild type Mtb antigen. In some embodiments, fragments of consensus proteins can comprise at least 20 amino acids or more, at least 30 amino acids or more, at least 40 amino acids or more, at least 50 amino acids or more, at least 60 amino acids or more, at least 70 amino acids or more, at least 80 amino acids or more, at least 90 amino acids or more, at least 100 amino acids or more, at least 110 amino acids or more, at least 120 amino acids or more, at least 130 amino acids or more, at least 140 amino acids or more, at least 150 amino acids or more, at least 160 amino acids or more, at least 170 amino acids or more, at least 180 amino acids or more of a consensus or wild type protein.

As used herein, "genetic construct" refers to the DNA or RNA molecules that comprise a nucleotide sequence which encodes an Mtb antigen. The coding sequence includes initiation and termination signals operably linked to regulatory elements including a promoter and polyadenylation signal capable of directing expression in the cells of the individual to whom the nucleic acid molecule is administered.

As used herein, "expressible form" refers to gene constructs that contain the necessary regulatory elements operable linked to a coding sequence that encodes an Mtb antigen such that when present in the cell of the individual, the coding sequence will be expressed.

As used herein, "homology" refers to a degree of complementarity. There can be partial homology or complete homology (i.e., identity). A partially complementary sequence that at least partially inhibits a completely complementary sequence from hybridizing to a target nucleic acid is referred to using the functional term "substantially homologous." When used in reference to a double-stranded nucleic acid sequence such as a cDNA or genomic clone, the term "substantially homologous" refers to a probe that can hybridize to a strand of the double-stranded nucleic acid sequence under conditions of low stringency. When used in reference to a single-stranded nucleic acid sequence, the term "substantially homologous" refers to a probe that can hybridize to (i.e., is the complement of) the single-stranded nucleic acid template sequence under conditions of low stringency.

As used herein, "identical" or "identity" in the context of two or more nucleic acids or polypeptide sequences, means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) residues can be considered equivalent. Identity can be performed manually or by using a computer sequence algorithm such as BLAST or BLAST 2.0.

As used herein, "immune response" means the activation of a host's immune system, e.g., that of a mammal, in response to the introduction of an Mtb antigen. The immune response can be in the form of a cellular or humoral response, or both.

As used herein, "Mtb antigen" means an antigen from *Mycobacterium tuberculosis*, which may be an isolated antigen, or an antigen that forms part of a fusion protein with other antigen(s).

As used herein, "nucleic acid" or "oligonucleotide" or "polynucleotide" means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions. Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

As used herein, "operably linked" means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

As used herein, "promoter" means a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents.

As used herein, "stringent hybridization conditions" means conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions can be selected to be about 5 to 10° C. lower than the thermal melting point ($T_m$) for the specific sequence at a defined ionic strength pH. The $T_m$ can be the temperature (under defined ionic strength, pH, and nucleic concentration) at which 50% of the probes complementary to the target hybridize to the target sequence at equilibrium (as the target sequences are present in excess, at T$_m$, 50% of the probes are occupied at equilibrium). Stringent conditions can be those in which the salt concentration is less than about 1.0 M sodium ion, such as about 0.01 to 1.0 M sodium ion concentration (or other salts) at pH 7.0 to 8.3 and the temperature is at least about 30° C. for short probes (e.g., about 10 to 50 nucleotides) and at least about 60° C. for long probes (e.g., greater than about 50 nucleotides). Stringent conditions can also be achieved with the addition of destabilizing agents such as formamide. For selective or specific hybridization, a positive signal can be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

As used herein, "substantially complementary" means that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, or more nucleotides or amino acids, or that the two sequences hybridize under stringent hybridization conditions.

As used herein, "substantially identical" means that a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540 or more nucleotides or amino acids, or with respect to nucleic acids, if the first sequence is substantially complementary to the complement of the second sequence.

As used herein, "variant" with respect to a nucleic acid means: i) a portion or fragment of a referenced nucleotide sequence; ii) the complement of a referenced nucleotide sequence or portion thereof; iii) a nucleic acid that is substantially identical to a referenced nucleic acid or the complement thereof; or iv) a nucleic acid that hybridizes under stringent conditions to the referenced nucleic acid, complement thereof, or a sequences substantially identical thereto.

As used herein, "variant" with respect to a peptide or polypeptide means that it differs in amino acid sequence by the insertion, deletion, or conservative substitution of amino acids, but retains at least one biological activity. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change Amino acid substitutions that are compatible with biological function are understood to depend on the relative similarity of the amino acids, and particularly the side chains of those amino acids, as revealed by the hydrophobicity, hydrophilicity, charge, size, and other properties.

As used herein, "vector" means a nucleic acid sequence containing an origin of replication. A vector can be a viral vector, bacteriophage, bacterial artificial chromosome or yeast artificial chromosome. A vector can be a DNA or RNA vector. A vector can be a self-replicating extrachromosomal vector.

The present disclosure provides fusion proteins comprising at least two Mtb antigens. In some embodiments, the fusion protein comprises at least three Mtb antigens. In some embodiments, the fusion protein comprises at least four Mtb antigens. In some embodiments, the fusion protein comprises at least five Mtb antigens. In some embodiments, the fusion protein comprises at least six Mtb antigens. In some embodiments, the fusion protein comprises at least seven Mtb antigens.

In some embodiments, the nucleic acid molecule encoding any particular Mtb antigen can be a mycobacterial sequence, a bacterial codon optimized sequence (such as an *E. coli* optimized sequence), or a mammalian optimized sequence (such as a human optimized sequence). The *E. coli* optimized sequences can be used, for example, to produce fusion proteins. The human optimized sequences can be used in, for example, viral vectors. Methods of codon optimization (whether for bacterial or mammalian) are well known to the skilled artisan.

In some embodiments, any of the fusion proteins described herein can comprise a C-terminal HA tag (e.g., YPYDVPDYA) (SEQ ID NO:17).

In some embodiments, the Mtb antigen is a PE antigen. In some embodiments, the PE antigen is Rv3872 (also known as PE35), Rv1788 (also known as PE18), Rv3893c (also known as PE36), Rv0285 (also known as PE5), Rv1818c (also known as PE_PGRS33; includes only the PE domain), Rv0159c (also known as PE3; includes only the PE domain), or Rv1172c (also known as PE12; includes only the PE domain).

A nucleotide sequence encoding Rv3872 is shown in Table 1 as SEQ ID NO:1, and an amino acid sequence of Rv3872 is shown in Table 1 as SEQ ID NO:2.

A nucleotide sequence encoding Rv1788 is shown in Table 1 as SEQ ID NO:3, and an amino acid sequence of Rv1788 is shown in Table 1 as SEQ ID NO:4.

A nucleotide sequence encoding Rv3893c is shown in Table 1 as SEQ ID NO:5, and an amino acid sequence of Rv3893c is shown in Table 1 as SEQ ID NO:6.

A nucleotide sequence encoding Rv0285 is shown in Table 1 as SEQ ID NO:7, and an amino acid sequence of Rv0285 is shown in Table 1 as SEQ ID NO:8.

A nucleotide sequence encoding Rv1818c is shown in Table 1 as SEQ ID NO:9, and an amino acid sequence of Rv1818c is shown in Table 1 as SEQ ID NO:10.

A nucleotide sequence encoding Rv0159c is shown in Table 1 as SEQ ID NO:11, and an amino acid sequence of Rv0159c is shown in Table 1 as SEQ ID NO:12.

A nucleotide sequence encoding Rv1172c is shown in Table 1 as SEQ ID NO:13, and an amino acid sequence of Rv1172c is shown in Table 1 as SEQ ID NO:14.

TABLE 1

| PE Antigens | |
|---|---|
| Construct | nucleotide sequence<br>amino acid sequence |
| Rv3872<br>(PE35) | ATGGAGAAGATGAGCCACGACCCCATCGCCGCCGACATCGGCACCCAGGTGAGCGACAA<br>CGCCCTGCACGGCGTGACCGCCGGCAGCACCGCCCTGACCAGCGTGACCGGCCTGGTGC |

TABLE 1-continued PE Antigens

| Construct | nucleotide sequence<br>amino acid sequence |
|---|---|
| | CCGCCGGCGCCGACGAGGTGAGCGCCCAGGCCGCCACCGCCTTCACCAGCGAGGGCATC<br>CAGCTGCTGGCCAGCAACGCCAGCGCCCAGGACCAGCTGCACAGGGCCGGCGAGGCCGT<br>GCAGGACGTGGCCAGGACCTACAGCCAGATCGACGACGGCGCCGCCGGCGTGTTCGCCG<br>AGTGA(SEQ ID NO: 1)<br>MEKMSHDPIAADIGTQVSDNALHGVTAGSTALTSVTGLPAGADEVSAQAATAFTSEGIQ<br>LLASNASAQDQLHRAGEAVQDVARTYSQIDDGAAGVFAE (SEQ ID NO: 2) |
| Rv1788<br>(PE18) | ATGAGCTTCGTGACCACCCAGCCCGAGGCCCTGGCCGCCGCCGCCGGCAGCCTGCAGGG<br>CATCGGCAGCGCCCTGAACGCCCAGAACGCCGCCGCCGCCACCCCCACCACCGGCGTGG<br>TGCCCGCCGCCGCCGACGAGGTGAGCGCCCTGACCGCCGCCCAGTTCGCCGCCCACGCC<br>CAGATCTACCAGGCCGTGAGCGCCCAGGCCGCCGCCATCCACGAGATGTTCGTGAACAC<br>CCTGCAGATGAGCAGCGGCAGCTACGCCGCCACCGAGGCCGCCAACGCCGCCGCCGCCG<br>GCTGA(SEQ ID NO: 3)<br>MSFVTTQPEALAAAAGSLQGIGSALNAQNAAAATPTTGVVPAAADEVSALTAAQFAAHA<br>QIYQAVSAQAAAIHEMFVTLQMSSGSYAATEAANAAAAG (SEQ ID NO: 4) |
| Rv3893c<br>(PE36) | ATGGTGTGGAGCGTGCAGCCCGAGGCCGTGCTGGCCAGCGCCGCCGCCGAGAGCGCCAT<br>CAGCGCCGAGACCGAGGCCGCCGCCGCCGGCGCCGCCCCCGCCCTGCTGAGCACCACCC<br>CCATGGGCGGCGACCCCGACAGCGCCATGTTCAGCGCCGCCCTGAACGCCTGCGGCGCC<br>AGCTACCTGGGCGTGGTGGCCGAGCACGCCAGCCAGAGGGGCCTGTTCGCCGGCTGA<br>(SEQ ID NO: 5)<br>MVWSVQPEAVLASAAAESAISAETEAAAAGAAPALLSTTPMGGDPDSAMFSAALNACGA<br>SYLGVVAEHASQRGLFAG (SEQ ID NO: 6) |
| Rv0285<br>(PE5) | ATGACCCTGAGGGTGGTGCCCGAGGGCCTGGCCGCCGCCAGCGCCGCCGTGGAGGCCCT<br>GACCGCCAGGCTGGCCGCCGCCCACGCCAGCGCCGCCCCCGTGATCACCGCCGTGGTGC<br>CCCCCGCCGCCGACCCCGTGAGCCTGCAGACCGCCGCCGGCTTCAGCGCCCAGGGCGTG<br>GAGCACGCCGTGGTGACCGCCGAGGGCGTGGAGGAGCTGGGCAGGGCCGGCGTGGGCGTG<br>GGCGAGAGCGGCGCCAGCTACCTGGCCGGCGACGCCGCCGCCGCCGCCACCTACGGCGT<br>GGTGGGCGGCTGA(SEQ ID NO: 7)<br>MTLRVVPEGLAAASAAVEALTARLAAAHASAAPVITAVVPPAADPVSLQTAAGFSAQGV<br>EHAVVTAEGVEELGRAGVGVGESGASYLAGDAAAAATYGVVGG<br>(SEQ ID NO: 8) |
| Rv1818c<br>(PE_PGRS33) | ATGAGCTTCGTGGTGACCATCCCCGAGGCCCTGGCCGCCGTGGCCACCGACCTGGCCGG<br>CATCGGCAGCACCATCGGCACCGCCAACGCCGCCGCCGCCGTGCCCACCACCACCGTGC<br>TGGCCGCCGCCGCCGACGAGGTGAGCGCCGCCATGGCCGCCCTGTTCAGCGGCCACGCC<br>CAGGCCTACCAGGCCCTGAGCGCCCAGGCCGCCCTGTTCCACGAGCAGTTCGTGAGGGC<br>CCTGACCGCCGGCGCCGGCAGCTACGCCGCCGCCGAGGCCGCCAGCGCCGCCCCCCTGG<br>AGGGCTGA(SEQ ID NO: 9)<br>MSFVVTIPEALAAVATDLAGIGSTIGTANAAAAVPTTTVLAAAADEVSAAMAALFSGHA<br>QAYQALSAQAALFHEQFVRALTAGAGSYAAAEAASAAPLEG (SEQ ID NO: 10) |
| Rv0159c<br>(PE3) | ATGAGCTACGTGATCGCCGCCCCCGAGATGCTGGCCACCACCGCCGCCGACGTGGACGG<br>CATCGGCAGCGCCATCAGGGCCGCCAGCGCCAGCGCCGCCGGCCCCACCACCGGCCTGC<br>TGGCCGCCGCCGCCGACGAGGTGAGCAGCGCCGCCGCCGCCCTGTTCAGCGAGTACGCC<br>AGGGAGTGCCAGGAGGTGCTGAAGCAGGCCGCCGCCTTCCACGGCGAGTTCACCAGGGC<br>CCTGGCCGCCGCCGGCGCCGCCTACGCCCAGGCCGAGGCCAGCAACACCGCCGCCATGA<br>GCGGCACCGCCGGCAGCAGCGGCGCCCTGGGCAGCTGA(SEQ ID NO: 11)<br>MSYVIAAPEMLATTAADVDGIGSAIRAASASAAGPTTGLLAAAADEVSSAAAALFSEYA<br>RECQEVLKQAAAFHGEFTRALAAAGAAYAQAEASNTAAMSGTAGSSGALGS<br>(SEQ ID NO: 12) |
| Rv1172c<br>(PE12) | ATGAGCTTCGTGTTCGCCGCCCCCGAGGCCCTGGCCGCCGCCGCCGCCGACATGGCCGG<br>CATCGGCAGCACCCTGAACGCCGCCAACGTGGTGGCCGCCGTGCCCACCACCGGCGTGC<br>TGGCCGCCGCCGCCGACGAGGTGAGCACCCAGGTGGCCGCCCTGCTGAGCGCCCACGCC<br>CAGGGCTACCAGCAGCTGAGCAGGCAGATGATGACCGCCTTCCACGACCAGTTCGTGCA<br>GGCCCTGAGGGCCAGCGCCGACGCCTACGCCACCGCCGAGGCCGCCAGCGCCGCCCAGACCA<br>TGGTGAACGCCGTGAACGCCCCCGCCAGGGCCCTGTGA(SEQ ID NO: 13)<br>MSFVFAAPEALAAAAADMAGIGSTLNAANVVAAVPTTGVLAAAADEVSTQVAALLSAHA<br>QGYQQLSRQMMTAFHDQFVQALRASADAYATAEASAAQTMVNAVNAPARLA<br>(SEQ ID NO: 14) |

In some embodiments, a composition comprises at least two of the PE antigens. In some embodiments, the composition comprises at least three of the PE antigens. In some embodiments, the composition comprises at least four of the PE antigens. In some embodiments, the composition comprises at least five of the PE antigens. In some embodiments, the composition comprises at least six of the PE antigens. In some embodiments, the composition comprises all seven PE antigens. In some embodiments, the composition comprises from at least two to seven of the PE antigens. In some embodiments, the composition comprises from at least three to seven of the PE antigens. In some embodiments, the composition comprises from at least four to seven of the PE antigens. In some embodiments, the composition comprises at least five to seven of the PE antigens. In some embodiments, the composition comprises six or seven of the PE antigens. In some embodiments, the composition further comprises a pharmaceutically acceptable carrier.

In some embodiments, the fusion protein comprises at least two of the PE antigens. In some embodiments, the fusion protein comprises at least three of the PE antigens. In some embodiments, the fusion protein comprises at least four of the PE antigens. In some embodiments, the fusion protein comprises at least five of the PE antigens. In some embodiments, the fusion protein comprises at least six of the PE antigens. In some embodiments, the fusion protein comprises all seven PE antigens. In some embodiments, the fusion protein comprises from at least two to seven of the PE antigens. In some embodiments, the fusion protein comprises from at least three to seven of the PE antigens. In some embodiments, the fusion protein comprises from at least four to seven of the PE antigens. In some embodiments, the fusion protein comprises at least five to seven of the PE antigens. In some embodiments, the fusion protein comprises six or seven of the PE antigens.

In some embodiments, the fusion protein comprises Rv3872 and Rv1788. In some embodiments, the fusion protein comprises Rv3893c, Rv0285, and Rv1818c. In some embodiments, the fusion protein comprises Rv0159c and Rv1172c.

In any of the embodiments of fusion proteins set forth herein, the individual PE antigens can be present in any order. For example, for a fusion protein comprising Rv3893c, Rv0285, and Rv1818c antigens, the first (or N-terminal) antigen may be Rv3893c, Rv0285, or Rv1818c; the second antigen may be Rv3893c, Rv0285, or Rv1818c (whichever one is not the first PE antigen); and the third antigen may be Rv3893c, Rv0285, or Rv1818c (whichever one is not the first or second PE antigen). Likewise for every fusion protein disclosed herein.

Individual PE antigens may be linked together in a C-terminus to N-terminus or N-terminus to C-terminus manner without any linker. Alternately, a linker may be present between any two PE antigens within any of the fusion proteins disclosed herein. In some embodiments, the linker is a segment of DNA or RNA optionally containing one or more restrictions sites, wherein the linker is inserted between nucleic acid molecules encoding two PE antigens of any of the fusion proteins disclosed herein.

In some embodiments, the fusion protein comprises Rv3872-Rv1788-Rv3893c-Rv0285-Rv1818c-Rv0159c-Rv1172c (Construct A; see Table 2). The nucleotide sequence is SEQ ID NO:15, and the corresponding amino acid sequence is SEQ ID NO:16 (with inserted AAA between Rv1788 and Rv3893c to disrupt possible epitope with homology to human proteins; C-terminal HA tag (YPYDVPDYA; SEQ ID NO:17) added).

TABLE 2

| PE Antigen Cassette | |
|---|---|
| Construct | nucleotide sequence<br>amino acid sequence |
| A | ATGGAGAAGATGAGCCACGACCCCATCGCCGCCGACATCGGCACCCAGGTGAGCGACAAC<br>GCCCTGCACGGCGTGACCGCCGGCAGCACCGCCCTGACCAGCGTGACCGGCCTGGTGCCC<br>GCCGGCGCCGACGAGGTGAGCGCCCAGGCCGCCACCGCCTTCACCAGCGAGGGCATCCAG<br>CTGCTGGCCAGCAACGCCAGCGCCCAGGACCAGCTGCACAGGGCCGGCGAGGCCGTGCAG<br>GACGTGGCCAGGACCTACAGCCAGATCGACGACGGCGCCGCCGGCGTGTTCGCCGAGATG<br>AGCTTCGTGACCACCCAGCCCGAGGCCCTGGCCGCCGCCGCCGGCAGCCTGCAGGGCATC<br>GGCAGCGCCCTGAACGCCCAGAACGCCGCCGCCGCCACCCCCACCACCGGCGTGGTGCCC<br>GCCGCCGCCGACGAGGTGAGCGCCCTGACCGCCGCCCAGTTCGCCGCCCACGCCCAGATC<br>TACCAGGCCGTGAGCGCCCAGGCCGCCGCCATCCACGAGATGTTCGTGAACACCCTGCAG<br>ATGAGCAGCGGCAGCTACGCCGCCACCGAGGCCGCCAACGCCGCCGCCGCCGGCGCCGCC<br>GCCATGGTGTGGAGCGTGCAGCCCGAGGCCGTGCTGGCCAGCGCCGCCGCCGAGAGCGCC<br>ATCAGCGCCGAGACCGAGGCCGCCGCCGCCGGCGCCGCCCCCGCCCTGCTGAGCACCACC<br>CCCATGGGCGGCGACCCCGACAGCGCCATGTTCAGCGCCGCCCTGAACGCCTGCGGCGCC<br>AGCTACCTGGGCGTGGTGGCCGAGCACGCCAGCCAGAGGGGCCTGTTCGCCGGCATGACC<br>CTGAGGGTGGTGCCCGAGGGCCTGGCCGCCGCCAGCGCCGCCGTGGAGGCCCTGACCGCC<br>AGGCTGGCCGCCGCCCACGCCAGCGCCGCCCCCGTGATCACCGCCGTGGTGCCCCCCGCC<br>GCCGACCCCGTGAGCCTGCAGACCGCCGCCGGCTTCAGCGCCCAGGGCGTGGAGCACGCC<br>GTGGTGACCGCCGAGGGCGTGGAGGAGCTGGGCAGGGCCGGCGTGGGCGTGGGCGAGAGC<br>GGCGCCAGCTACCTGGCCGGCGACGCCGCCGCCGCCGCCACCTACGGCGTGGTGGGCGGC<br>ATGAGCTTCGTGGTGACCATCCCCGAGGCCCTGGCCGCCGTGGCCACCGACCTGGCCGGC<br>ATCGGCAGCACCATCGGCACCGCCAACGCCGCCGCCGCCGTGCCCACCACCACCGTGCTG<br>GCCGCCGCCGCCGACGAGGTGAGCGCCGCCATGGCCGCCCTGTTCAGCGGCCACGCCCAG<br>GCCTACCAGGCCCTGAGCGCCCAGGCCGCCCTGTTCCACGAGCAGTTCGTGAGGGCCCTG<br>ACCGCCGGCGCCGGCAGCTACGCCGCCATGAGCTACGTGATCGCCGCCCCCGAGATGCTG<br>GCCACCACCGCCGCCGACGTGGACGGCATCGGCAGCGCCATCAGGGCCGCCAGCGCCAGC<br>GCCGCCGGCCCCACCACCGGCCTGCTGGCCGCCGCCGCCGACGAGGTGAGCAGCGCCGCC<br>GCCGCCCTGTTCAGCGAGTACGCCAGGGAGTGCCAGGAGGTGCTGAAGCAGGCCGCCGCC<br>TTCCACGGCGAGTTCACCAGGGCCCTGGCCGCCGCCGGCGCCGCCTACGCCCAGGCCGAG<br>GCCAGCAACACCGCCGCCATGAGCGGCACCGCCGGCAGCAGCGGCGCCCTGGGCAGCATG<br>AGCTTCGTGTTCGCCGCCCCCGAGGCCCTGGCCGCCGCCGCCGCCGACATGGCCGGCATC<br>GGCAGCACCCTGAACGCCGCCAACGTGGTGGCCGCCGTGCCCACCACCGGCGTGCTGGCC<br>GCCGCCGCCGACGAGGTGAGCACCCAGGTGGCCGCCCTGCTGAGCGCCCACGCCCAGGGC<br>TACCAGCAGCTGAGCAGGCAGATGATGACCGCCTTCCACGACCAGTTCGTGCAGGCCCTG<br>AGGGCCAGCGCCGACGCCTACGCCACCGCCGAGGCCAGCGCCGCCCAGACCATGGTGAAC<br>GCCGTGAACGCCCCCGCCAGGGCCCTGTACCCCTACGACGTGCCCGACTACGCCTGA<br>(SEQ ID NO: 15)<br>MEKMSHDPIAADIGTQVSDNALHGVTAGSTALTSVTGLVPAGADEVSAQAATAFTSEGIQ<br>LLASNASAQDQLHRAGEAVQDVARTYSQIDDGAAGVFAEMSFVTTQPEALAAAAGSLQGI<br>GSALNAQNAAAATPTTGVVPAAADEVSALTAAQFAAHAQIYQAVSAQAAAIHEMFVNTLQ<br>MSSGSYAATEAANAAAAGAAAMVWSVQPEAVLASAAAESAISAETEAAAAGAAPALLSTT<br>PMGGDPDSAMFSAALNACGASYLGVVAEHASQRGLFAGMTLRVVPEGLAAASAAVEALTA<br>RLAAAHASAAPVITAVVPPAADPVSLQTAAGFSAQGVEHAVVTAEGVEELGRAGVGVGES<br>GASYLAGDAAAAATYGVVGGMSFVVTIPEALAAVATDLAGIGSTIGTANAAAAVPTTTVL |

TABLE 2-continued

PE Antigen Cassette

| Construct | nucleotide sequence<br>amino acid sequence |
|---|---|
| | AAAADEVSAAMAALFSGHAQAYQALSAQAALFHEQFVRALTAGAGSYAAMSYVIAAPEML<br>ATTAADVDGIGSAIRAASASAAGPTTGLLAAAADEVSSAAAALFSEYARECQEVLKQAAA<br>FHGEFTRALAAAGAAYAQAEASNTAAMSGTAGSSGALGSMSFVFAAPEALAAAAADMAGI<br>GSTLNAANVVAAVPTTGVLAAAADEVSTQVAALLSAHAQGYQQLSRQMMTAFHDQFVQAL<br>RASADAYATAEASAAQTMVNAVNAPARALYPYDVPDYA(SEQ ID NO: 16) |

In some embodiments, the Mtb antigen is a PPE antigen. In some embodiments, the PPE antigen is Rv3873 (also known as PPE68; includes only the PPE domain), Rv1387 (also known as PPE20; includes only the PPE domain), Rv3892c (also known as PPE69; includes only the PPE domain), Rv1789 (also known as PPE26; includes only the PPE domain), Rv1800 (also known as PPE28; includes only the PPE domain), or Rv1039c (also known as PPE15; includes only the PPE domain).

A nucleotide sequence encoding Rv3873 is shown in Table 3 as SEQ ID NO:18, and an amino acid sequence of Rv3873 is shown in Table 3 as SEQ ID NO:19.

A nucleotide sequence encoding Rv1387 is shown in Table 3 as SEQ ID NO:20, and an amino acid sequence of Rv1387 is shown in Table 3 as SEQ ID NO:21.

A nucleotide sequence encoding Rv3892c is shown in Table 3 as SEQ ID NO:22, and an amino acid sequence of Rv3892c is shown in Table 3 as SEQ ID NO:23.

A nucleotide sequence encoding Rv1789 is shown in Table 3 as SEQ ID NO:24, and an amino acid sequence of Rv1789 is shown in Table 3 as SEQ ID NO:25.

A nucleotide sequence encoding Rv1800 is shown in Table 3 as SEQ ID NO:26, and an amino acid sequence of Rv1800 is shown in Table 3 as SEQ ID NO:27.

A nucleotide sequence encoding Rv1039c is shown in Table 3 as SEQ ID NO:28, and an amino acid sequence of Rv1039c is shown in Table 3 as SEQ ID NO:29.

TABLE 3

PPE Antigens

| Construct | nucleotide sequence<br>amino acid sequence |
|---|---|
| Rv3873<br>(PPE68) | ATGCTGTGGCACGCCATGCCCCCCGAGCTGAACACCGCCAGGCTGATGGCCGGCG<br>CCGGCCCCGCCCCCATGCTGGCCGCCGCCGCCGGCTGGCAGACCCTGAGCGCCGC<br>CCTGGACGCCCAGGCCGTGGAGCTGACCGCCAGGCTGAACAGCCTGGGCGAGGCC<br>TGGACCGGCGGCGGCAGCGACAAGGCCCTGGCCGCCGCCACCCCCATGGTGGTGT<br>GGCTGCAGACCGCCAGCACCCAGGCCAAGACCAGGGCCATGCAGGCCACCGCCCA<br>GGCCGCCGCCTACACCCAGGCCATGGCCACCACCCCCAGCCTGCCCGAGATCGCC<br>GCCAACCACATCACCCAGGCCGTGCTGACCGCCACCAACTTCTTCGGCATCAACA<br>CCATCCCCATCGCCCTGACCGAGATGGACTACTTCATCAGGATGTGGAACCAGGC<br>CGCCCTGGCCATGGAGGTGTACCAGGCCGAGACCGCCGTGAACACCCTGTTCGAG<br>AAGCTGGAGCCCATGGCCAGCATCCTGGACCCCGGCGCCAGCCAGTGA<br>(SEQ ID NO: 18)<br>MLWHAMPPELNTARLMAGAGPAPMLAAAAGWQTLSAALDAQAVELTARLNSLGEA<br>WTGGGSDKALAAATPMVVWLQTASTQAKTRAMQATAQAAAYTQAMATTPSLPEIA<br>ANHITQAVLTATNFFGINTIPIALTEMDYFIRMWNQAALAMEVYQAETAVNTLFE<br>KLEPMASILDPGASQ (SEQ ID NO: 19) |
| Rv1387<br>(PPE20) | ATGACCGAGCCCTGGATCGCCTTCCCCCCCGAGGTGCACAGCGCCATGCTGAACT<br>ACGGCGCCGGCGTGGGCCCCATGCTGATCAGCGCCACCCAGAACGGCGAGCTGAG<br>CGCCCAGTACGCCGAGGCCGCCAGCGAGGTGGAGGAGCTGCTGGGCGTGGTGGCC<br>AGCGAGGGCTGGCAGGGCCAGGCCGCCGAGGCCTTCGTGGCCGCCTACATGCCCT<br>TCCTGGCCTGGCTGATCCAGGCCAGCGCCGACTGCGTGGAGATGGCCGCCCAGCA<br>GCACGTGGTGATCGAGGCCTACACCGCCGCCGTGGAGCTGATGCCCACCCAGGTG<br>GAGCTGGCCGCCAACCAGATCAAGCTGGCCGTGCTGGTGGCCACCAACTTCTTCG<br>GCATCAACACCATCCCCATCGCCATCAACGAGGCCGAGTACGTGGAGATGTGGGT<br>GAGGGCCGCCACCACCATGGCCACCTACAGCACCGTGAGCAGGAGCGCCCTGAGC<br>GCCATGCCCCACACCAGCCCCCCCCCCCTGATCCTGAAGAGCGACTGA<br>(SEQ ID NO: 20<br>MTEPWIAFPPEVHSAMLNYGAGVGPMLISATQNGELSAQYAEAASEVEELLGVVA<br>SEGWQGQAAEAFVAAYMPFLAWLIQASADCVEMAAQQHVVIEAYTAAVELMPTQV<br>ELAANQIKLAVLVATNFFGINTIPIAINEAEYVEMWVRAATTMATYSTVSRSALS<br>AMPHTSPPPLILKSD(SEQ ID NO: 21) |
| Rv3892c<br>(PPE69) | ATGCCCGACCCCGGCTGGGCCGCCAGGACCCCCGAGGCCAACGACCTGCTGCTGA<br>CCGCCGGCACCGGCGTGGGCACCCACCTGGCCAACCAGACCGCCTGGACCACCCT<br>GGGCGCCAGCCACCACGCCAGCGGCGTGGCCAGCGCCATCAACACCGCCGCCACC<br>GCCGCCAGCTGGCTGGGCGTGGGCAGCGCCGCCAGCGCCCTGAACGTGACCATGC<br>TGAACGCCACCCTGCACGGCCTGGCCGGCTGGGTGGACGTGAAGCCCGCCGTGGT<br>GAGCACCGCCATCGCCGCCTTCGAGACCGCCAACGCCGCCATGAGGCCCGCCCCC<br>GAGTGCATGGAGAACAGGGACGAGTGGGGCGTGGACAACGCCATCAACCCCAGCG<br>TGCTGTGGACCCTGACCCCCAGGATCGTGAGCCTGGACGTGGAGTACTTCGGCGT<br>GATGTGGCCCAACAACGCCGCCGTGGGCGCCACCTACGGCGGCGTGCTGGCCGCC |

TABLE 3-continued

PPE Antigens

| Construct | nucleotide sequence<br>amino acid sequence |
|---|---|
| | CTGGCCGAGAGCCTGGCCATCCCCCCCCCCGTGGCCACCATGGGCTGA<br>(SEQ ID NO: 22)<br>MPDPGWAARTPEANDLLLTAGTGVGTHLANQTAWTTLGASHHASGVASAINTAAT<br>AASWLGVGSAASALNVTMLNATLHGLAGWVDVKPAVVSTAIAAFETANAAMRPAP<br>ECMENRDEWGVDNAINPSVLWTLTPRIVSLDVEYFGVMWPNNAAVGATYGGVLAA<br>LAESLAIPPPVATMG (SEQ ID NO: 23) |
| Rv1789<br>(PPE26) | ATGGACTTCGGCGCCCTGCCCCCCGAGGTGAACAGCGTGAGGATGTACGCCGGCC<br>CCGGCAGCGCCCCCATGGTGGCCGCCGCCAGCGCCTGGAACGGCCTGGCCGCCGA<br>GCTGAGCAGCGCCGCCACCGGCTACGAGACCGTGATCACCCAGCTGAGCAGCGAG<br>GGCTGGCTGGGCCCCGCCAGCGCCGCCATGGCCGAGGCCGTGGCCCCCTACGTGG<br>CCTGGATGAGCGCCGCCGCCGCCCAGGCCGAGCAGGCCGCCACCCAGGCCAGGGC<br>CGCCGCCGCCGCCTTCGAGGCCGCCTTCGCCGCCACCGTGCCCCCCCCCCTGATC<br>GCCGCCAACAGGGCCCAGCCTGATGCAGCTGATCAGCACCAACGTGTTCGGCCAGA<br>ACACCAGCGCCATCGCCGCCGCCGAGGCCCAGTACGGCGAGATGTGGGCCCAGGA<br>CAGCGCCGCCATGTACGCCTACGCCGGCAGCAGCGCCAGCGCCAGCGCCGTGACC<br>CCCTTCAGCACCCCCCCCCAGATCGCCAACCCCACCGCCCAGGGCTGA<br>(SEQ ID NO: 24)<br>MDFGALPPEVNSVRMYAGPGSAPMVAAASAWNGLAAELSSAATGYETVITQLSSE<br>GWLGPASAAMAEAVAPYVAWMSAAAAQAEQAATQARAAAAAFEAAFAATVPPPLI<br>AANRASLMQLISTNVFGQNTSAIAAAEAQYGEMWAQDSAAMYAYAGSSASASAVT<br>PFSTPPQIANPTAQG (SEQ ID NO: 25) |
| Rv1800<br>(PPE28) | ATGCTGCCCAACTTCGCCGTGCTGCCCCCCGAGGTGAACAGCGCCAGGGTGTTCG<br>CCGGCGCCGGCAGCGCCCCCATGCTGGCCGCCGCCGCCGCCTGGGACGACCTGGC<br>CAGCGAGCTGCACTGCGCCGCCATGAGCTTCGGCAGCGTGACCAGCGGCCTGGTG<br>GTGGGCTGGTGGCAGGGCAGCGCCAGCGCCGCCATGGTGGACGCCGCCGCCAGCT<br>ACATCGGCTGGCTGAGCACCAGCGCCGCCCACGCCGAGGGCGCCGCCGGCCTGGC<br>CAGGGCCGCCGTGAGCGTGTTCGAGGAGGCCCTGGCCGCCACCGTGCACCCCGCC<br>ATGGTGGCCGCCAACAGGGCCCAGGTGGCCAGCCTGGTGGCCAGCAACCTGTTCG<br>GCCAGAACGCCCCCGCCATCGCCGCCCTGGAGAGCCTGTACGAGTGCATGTGGGC<br>CCAGGACGCCGCCGCCATGGCCGGCTACTACGTGGGCGCCAGCGCCGTGGCCACC<br>CAGCTGGCCAGCTGGCTGCAGAGGCTGCAGAGCATCCCCGGCGCCTGA<br>(SEQ ID NO: 26)<br>MLPNFAVLPPEVNSARVFAGAGSAPMLAAAAAWDDLASELHCAAMSFGSVTSGLV<br>VGWWQGSASAAMVDAAASYIGWLSTSAAHAEGAAGLARAAVSVFEEALAATVHPA<br>MVAANRAQVASLVASNLFGQNAPAIAALESLYECMWAQDAAAMAGYYVGASAVAT<br>QLASWLQRLQSIPGA (SEQ ID NO: 27) |
| Rv1039c<br>(PPE15) | ATGGACTTCGGCGCCCTGCCCCCCGAGATCAACAGCGCCAGGATGTACGCCGGCG<br>CCGGCGCCGGCCCCATGATGGCCGCCGGCGCCGCCTGGAACGGCCTGGCCGCCGA<br>GCTGGGCACCACCGCCGCCAGCTACGAGAGCGTGATCACCAGGCTGACCACCGAG<br>AGCTGGATGGGCCCCGCCAGCATGGCCATGGTGGCCGCCGCCCAGCCCTACCTGG<br>CCTGGCTGACCTACACCGCCGAGGCCGCCGCCCACGCCGGCAGCCAGGCCATGGC<br>CAGCGCCGCCGCCTACGAGGCCGCCTACGCCATGACCGTGCCCCCCGAGGTGGTG<br>GCCGCCAACAGGGCCCTGCTGGCCGCCCTGGTGGCCACCAACGTGCTGGGCATCA<br>ACACCCCCGCCATCATGGCCACCGAGGCCCTGTACGCCGAGATGTGGGCCCAGGA<br>CGCCCTGGCCATGTACGGCTACGCCGCCGCCAGCGGCGCCGCCGGCATGCTGCAG<br>CCCCTGAGCCCCCCCAGCCAGACCACCAACCCCGGCGGCCTGGCCTGA<br>(SEQ ID NO: 28)<br>MDFGALPPEINSARMYAGAGAGPMMAAGAAWNGLAAELGTTAASYESVITRLTTE<br>SWMGPASMAMVAAAQPYLAWLTYTAEAAAHAGSQAMASAAAYEAAYAMTVPPEVV<br>AANRALLAALVATNVLGINTPAIMATEALYAEMWAQDALAMYGYAAASGAAGMLQ<br>PLSPPSQTTNPGGLA (SEQ ID NO: 29) |

In some embodiments, a composition comprises at least two of the PPE antigens. In some embodiments, the composition comprises at least three of the PPE antigens. In some embodiments, the composition comprises at least four of the PPE antigens. In some embodiments, the composition comprises at least five of the PPE antigens. In some embodiments, the composition comprises all six PPE antigens. In some embodiments, the composition comprises from at least two to six of the PPE antigens. In some embodiments, the composition comprises from at least three to six of the PPE antigens. In some embodiments, the composition comprises from at least four to six of the PPE antigens. In some embodiments, the composition comprises at least five or six of the PPE antigens. In some embodiments, the composition further comprises a pharmaceutically acceptable carrier.

In some embodiments, the fusion protein comprises at least two of the PPE antigens. In some embodiments, the fusion protein comprises at least three of the PPE antigens. In some embodiments, the fusion protein comprises at least four of the PPE antigens. In some embodiments, the fusion protein comprises at least five of the PPE antigens. In some embodiments, the fusion protein comprises all six PPE antigens. In some embodiments, the fusion protein comprises from at least two to six of the PPE antigens. In some embodiments, the fusion protein comprises from at least three to six of the PPE antigens. In some embodiments, the fusion protein comprises from at least four to six of the PPE antigens. In some embodiments, the fusion protein comprises at least five or six of the PPE antigens.

In some embodiments, the fusion protein comprises Rv3873, Rv1387, and Rv3892c. In some embodiments, the fusion protein comprises Rv1789, Rv1800, and Rv1039c.

In any of the embodiments of fusion proteins set forth herein, the individual PPE antigens can be present in any order. For example, for a fusion protein comprising Rv1789, Rv1800, and Rv1039c antigens, the first (or N-terminal) antigen may be Rv1789, Rv1800, or Rv1039c; the second antigen may be Rv1789, Rv1800, or Rv1039c (whichever one is not the first PPE antigen); and the third antigen may be Rv1789, Rv1800, and Rv1039c (whichever one is not the first or second PPE antigen). Likewise for every fusion protein disclosed herein.

Individual PPE antigens may be linked together in a C-terminus to N-terminus or N-terminus to C-terminus manner without any linker. Alternately, a linker may be present between any two PPE antigens within any of the fusion proteins disclosed herein. In some embodiments, the linker is a segment of DNA or RNA optionally containing one or more restrictions sites, wherein the linker is inserted between nucleic acid molecules encoding two PE antigens of any of the fusion proteins disclosed herein.

In some embodiments, the fusion protein comprises Rv3873-Rv1387-Rv3892c (Construct B; see Table 4). The nucleotide sequence is SEQ ID NO:30, and the corresponding amino acid sequence is SEQ ID NO:31 (including a C-terminal HA tag (YPYDVPDYA; SEQ ID NO:17) added).

In some embodiments, the fusion protein comprises Rv1789-Rv1800-Rv1039c (Construct C; see Table 4). The nucleotide sequence is SEQ ID NO:32, and the corresponding amino acid sequence is SEQ ID NO:33 (including a C-terminal HA tag (YPYDVPDYA; SEQ ID NO:17) added).

TABLE 4

PPE Antigen Cassette

| Construct | nucleotide sequence<br>amino acid sequence |
|---|---|
| B | ATGCTGTGGCACGCCATGCCCCCCGAGCTGAACACCGCCAGGCTG<br>ATGGCCGGCGCCGGCCCCGCCCCCATGCTGGCCGCCGCCGCCGGC<br>TGGCAGACCCTGAGCGCCGCCCTGGACGCCCAGGCCGTGGAGCTG<br>ACCGCCAGGCTGAACAGCCTGGGCGAGGCCTGGACCGGCGGCGG<br>CAGCGACAAGGCCCTGGCCGCCGCCACCCCCATGGTGGTGTGGCT<br>GCAGACCGCCAGCACCCAGGCCAAGACCAGGGCCATGCAGGCCA<br>CCGCCCAGGCCGCCGCCTACACCCAGGCCATGGCCACCACCCCA<br>GCCTGCCCGAGATCGCCGCCAACCACATCACCCAGGCCGTGCTGA<br>CCGCCACCAACTTCTTCGGCATCAACACCATCCCCATCGCCCTGAC<br>CGAGATGGACTACTTCATCAGGATGTGGAACCAGGCCGCCCTGGC<br>CATGGAGGTGTACCAGGCCGAGACCGCCGTGAACACCCTGTTCGA<br>GAAGCTGGAGCCCATGGCCAGCATCCTGGACCCCGGCGCCAGCCA<br>GATGACCGAGCCCTGGATCGCCTTCCCCCCCGAGGTGCACAGCGC<br>CATGCTGAACTACGGCGCCGGCGTGGGCCCCATGCTGATCAGCGC<br>CACCCAGAACGGCGAGCTGAGCGCCCAGTACGCCGAGGCCGCCA<br>GCGAGGTGGAGGAGCTGCTGGGCGTGGTGGCCAGCGAGGGCTGG<br>CAGGGCCAGGCCGCCGAGGCCTTCGTGGCCGCCTACATGCCCTTC<br>CTGGCCTGGCTGATCCAGGCCAGCGCCGACTGCGTGGAGATGGCC<br>GCCCAGCAGCACGTGGTGATCGAGGCCTACACCGCCGCCGTGGAG<br>CTGATGCCCACCCAGGTGGAGCTGGCCGCCAACCAGATCAAGCTG<br>GCCGTGCTGGTGGCCACCAACTTCTTCGGCATCAACACCATCCCC<br>ATCGCCATCAACGAGGCCGAGTACGTGGAGATGTGGGTGAGGGC<br>CGCCACCACCATGGCCACCTACAGCACCGTGAGCAGGAGCGCCCT<br>GAGCGCCATGCCCCACACCAGCCCCCCCCCCCTGATCCTGAAGAG<br>CGACATGCCCGACCCCGGCTGGGCCGCCAGGACCCCCGAGGCCAA<br>CGACCTGCTGCTGACCGCCGGCACCGGCGTGGGCACCCACCTGGC<br>CAACCAGACCGCCTGGACCACCCTGGGCGCCAGCCACCACGCCAG<br>CGGCGTGGCCAGCGCCATCAACACCGCCGCCACCGCCGCCAGCTG<br>GCTGGGCGTGGGCAGCGCCGCCAGCGCCCTGAACGTGACCATGCT<br>GAACGCCACCCTGCACGGCCTGGCCGGCTGGGTGGACGTGAAGCC<br>CGCCGTGGTGAGCACCGCCATCGCCGCCITCGAGACCGCCAACGC<br>CGCCATGAGGCCCGCCCCCGAGTGCATGGAGAACAGGGACGAGT<br>GGGGCGTGGACAACGCCATCAACCCCAGCGTGCTGTGGACCCTGA<br>CCCCCAGGATCGTGAGCCTGGACGTGGAGTACTTCGGCGTGATGT<br>GGCCCAACAACGCCGCCGTGGGCGCCACCTACGGCGGCGTGCTGG<br>CCGCCCTGGCCGAGAGCCTGGCCATCCCCCCCCCCGTGGCCACCA<br>TGGGCTACCCCTACGACGTGCCCGACTACGCCTGA (SEQ ID NO: 30)<br>MLWHAMPPELNTARLMAGAGPAPMLAAAAGWQTLSAALDAQAVE<br>LTARLNSLGEAWTGGGSDKALAAATPMVVWLQTASTQAKTRAMQ<br>ATAQAAAYTQAMATTPSLPEIAANHITQAVLTATNFFGINTIPIALTE<br>MDYFIRMWNQAALAMEVYQAETAVNTLFEKLEPMASILDPGASQM<br>TEPWIAFPPEVHSAMLNYGAGVGPMLISATQNGELSAQYAEAASEVE<br>ELLGVVASEGWQGQAAEAFVAAYMPFLAWLIQASADCVEMAAQQH<br>VVIEAYTAAVELMPTQVELAANQIKLAVLVATNFFGINTIPIAINEAEY<br>VEMWVRAATTMATYSTVSRSALSAMPHTSPPPLILKSDMPDPGWAA<br>RTPEANDLLLTAGTGVGTHLANQTAWTTLGASHHASGVASAINTAA<br>TAASWLGVGSAASALNVTMLNATLHGLAGWVDVKPAVVSTAIAAF<br>ETANAAMRPAPECMENRDEWGVDNAINPSVLWTLTPRIVSLDVEYF<br>GVMWPNNAAVGATYGGVLAALAESLAIPPPVATMGYPYDVPDYA<br>(SEQ ID NO: 31) |

TABLE 4-continued

| PPE Antigen Cassette | |
|---|---|
| Construct | nucleotide sequence<br>amino acid sequence |
| C | ATGGACITCGGCGCCCTGCCCCCCGAGGTGAACAGCGTGAGGATG<br>TACGCCGGCCCCGGCAGCGCCCCCATGGTGGCCGCCGCCAGCGCC<br>TGGAACGGCCTGGCCGCCGAGCTGAGCAGCGCCGCCACCGGCTAC<br>GAGACCGTGATCACCCAGCTGAGCAGCGAGGGCTGGCTGGGCCCC<br>GCCAGCGCCGCCATGGCCGAGGCCGTGGCCCCCTACGTGGCCTGG<br>ATGAGCGCCGCCGCCGCCCAGGCCGAGCAGGCCGCCACCCAGGC<br>CAGGGCCGCCGCCGCCGCCTTCGAGGCCGCCTTCGCCGCCACCGT<br>GCCCCCCCCCCTGATCGCCGCCAACAGGGCCAGCCTGATGCAGCT<br>GATCAGCACCAACGTGTTCGGCCAGAACACCAGCGCCATCGCCGC<br>CGCCGAGGCCCAGTACGGCGAGATGTGGGCCCAGGACAGCGCCG<br>CCATGTACGCCTACGCCGGCAGCAGCGCCAGCGCCAGCGCCGTGA<br>CCCCCTTCAGCACCCCCCCCAGATCGCCAACCCCACCGCCCAGG<br>GCATGCTGCCCAACTTCGCCGTGCTGCCCCCCGAGGTGAACAGCG<br>CCAGGGTGTTCGCCGGCGCCGGCAGCGCCCCCATGCTGGCCGCCG<br>CCGCCGCCTGGGACGACCTGGCCAGCGAGCTGCACTGCGCCGCCA<br>TGAGCTTCGGCAGCGTGACCAGCGGCCTGGTGGTGGGCTGGTGGC<br>AGGGCAGCGCCAGCGCCGCCATGGTGGACGCCGCCGCCAGCTAC<br>ATCGGCTGGCTGAGCACCAGCGCCGCCCACGCCGAGGGCGCCGCC<br>GGCCTGGCCAGGGCCGCCGTGAGCGTGTTCGAGGAGGCCCTGGCC<br>GCCACCGTGCACCCCGCCATGGTGGCCGCCAACAGGGCCCAGGTG<br>GCCAGCCTGGTGGCCAGCAACCTGTTCGGCCAGAACGCCCCCGCC<br>ATCGCCGCCCTGGAGAGCCTGTACGAGTGCATGTGGGCCCAGGAC<br>GCCGCCGCCATGGCCGGCTACTACGTGGGCGCCAGCGCCGTGGCC<br>ACCCAGCTGGCCAGCTGGCTGCAGAGGCTGCAGAGCATCCCCGGC<br>GCCATGGACTTCGGCGCCCTGCCCCCCGAGATCAACAGCGCCAGG<br>ATGTACGCCGGCGCCGGCGCCGGCCCCATGATGGCCGCCGGCGCC<br>GCCTGGAACGGCCTGGCCGCCGAGCTGGGCACCACCGCCGCCAGC<br>TACGAGAGCGTGATCACCAGGCTGACCACCGAGAGCTGGATGGG<br>CCCCGCCAGCATGGCCATGGTGGCCGCCGCCCAGCCCTACCTGGC<br>CTGGCTGACCTACACCGCCGAGGCCGCCGCCCACGCCGGCAGCCA<br>GGCCATGGCCAGCGCCGCCGCCTACGAGGCCGCCTACGCCATGAC<br>CGTGCCCCCCGAGGTGGTGGCCGCCAACAGGGCCCTGCTGGCCGC<br>CCTGGTGGCCACCAACGTGCTGGGCATCAACACCCCCGCCATCAT<br>GGCCACCGAGGCCCTGTACGCCGAGATGTGGGCCCAGGACGCCCT<br>GGCCATGTACGGCTACGCCGCCGCCAGCGGCGCCGCCGGCATGCT<br>GCAGCCCCTGAGCCCCCCCAGCCAGACCACCAACCCCGGCGGCCT<br>GGCCTACCCCTACGACGTGCCCGACTACGCCTGA (SEQ ID NO: 32)<br><br>MDFGALPPEVNSVRMYAGPGSAPMVAAASAWNGLAAELSSAATGY<br>ETVITQLSSEGWLGPASAAMAEAVAPYVAWMSAAAAQAEQAATQA<br>RAAAAAFEAAFAATVPPPLIAANRASLMQLISTNVFGQNTSAIAAAE<br>AQYGEMWAQDSAAMYAYAGSSASASAVTPFSTPPQIANPTAQGMLP<br>NFAVLPPEVNSARVFAGAGSAPMLAAAAAWDDLASELHCAAMSFG<br>SVTSGLVVGWWQGSASAAMVDAAASYIGWLSTSAAHAEGAAGLAR<br>AAVSVFEEALAATVHPAMVAANRAQVASLVASNLFGQNAPAIAALE<br>SLYECMWAQDAAAMAGYYVGASAVATQLASWLQRLQSIPGAMDF<br>GALPPEINSARMYAGAGAGPMMAAGAAWNGLAAELGTTAASYESV<br>ITRLTTESWMGPASMAMVAAAQPYLAWLTYTAEAAAHAGSQAMAS<br>AAAYEAAYAMTVPPEVVAANRALLAALVATNVLGINTPAIMATEAL<br>YAEMWAQDALAMYGYAAASGAAGMLQPLSPPSQTTNPGGLAYPYD<br>VPDYA (SEQ ID NO: 33) |

In some embodiments, the Mtb antigen is an ESX antigen. In some embodiments, the ESX antigen is Rv3017c (also known as esxQ), Rv3020c (also known as esxS), Rv3019c (also known as esxR), Rv3891c (also known as esxD), Rv2346c (also known as esxO), Rv3445c (also known as esxU), Rv3619c (also known as esxV), Rv3875 (also known as esxA and ESAT6), or Rv3874 (also known as esxB and CFP10).

A nucleotide sequence encoding Rv3017c is shown in Table 5 as SEQ ID NO:34, and an amino acid sequence of Rv3017c is shown in Table 5 as SEQ ID NO:35.

A nucleotide sequence encoding Rv3020c is shown in Table 5 as SEQ ID NO:36, and an amino acid sequence of Rv3020c is shown in Table 5 as SEQ ID NO:37.

A nucleotide sequence encoding Rv3019c is shown in Table 5 as SEQ ID NO:38, and an amino acid sequence of Rv3019c is shown in Table 5 as SEQ ID NO:39.

A nucleotide sequence encoding Rv3891c is shown in Table 5 as SEQ ID NO:40, and an amino acid sequence of Rv3891c is shown in Table 5 as SEQ ID NO:41.

A nucleotide sequence encoding Rv2346c is shown in Table 5 as SEQ ID NO:42, and an amino acid sequence of Rv2346c is shown in Table 5 as SEQ ID NO:43.

A nucleotide sequence encoding Rv3445c is shown in Table 5 as SEQ ID NO:44, and an amino acid sequence of Rv3445c is shown in Table 5 as SEQ ID NO:45.

A nucleotide sequence encoding Rv3619c is shown in Table 5 as SEQ ID NO:46, and an amino acid sequence of Rv3619c is shown in Table 5 as SEQ ID NO:47.

A nucleotide sequence encoding Rv3875 is shown in Table 5 as SEQ ID NO:48, and an amino acid sequence of Rv3875 is shown in Table 5 as SEQ ID NO:49.

A nucleotide sequence encoding Rv3874 is shown in Table 5 as SEQ ID NO:50, and an amino acid sequence of Rv3874 is shown in Table 5 as SEQ ID NO:51.

TABLE 5

ESX Antigens

| Construct | nucleotide sequence<br>amino acid sequence |
|---|---|
| Rv3017c<br>(esxQ) | GTGAGCCAGAGCATGTACAGCTACCCCGCCATGACCGCCAACGTGGGCGACATGGCCGGCT<br>ACACCGGCACCACCCAGAGCCTGGGCGCCGACATCGCCAGCGAGAGGACCGCCCCCAGCAG<br>GGCCTGCCAGGGCGACCTGGGCATGAGCCACCAGGACTGGCAGGCCCAGTGGAACCAGGCC<br>ATGGAGGCCCTGGCCAGGGCCTACAGGAGGTGCAGGAGGGCCCTGAGGCAGATCGGCGTGC<br>TGGAGAGGCCCGTGGGCGACAGCAGCGACTGCGGCACCATCAGGGTGGGCAGCTTCAGGGG<br>CAGGTGGCTGGACCCCAGGCACGCCGGCCCCGCCACCGCCGCCGACGCCGGCGACTGA<br>(SEQ ID NO: 34)<br>VSQSMYSYPAMTANVGDMAGYTGTTQSLGADIASERTAPSRACQGDLGMSHQDWQAQWNQA<br>MEALARAYRRCRRALRQIGVLERPVGDSSDCGTIRVGSFRGRWLDPRHAGPATAADAGD<br>(SEQ ID NO: 35) |
| Rv3020c<br>(esxS) | ATGAGCCTGCTGGACGCCCACATCCCCCAGCTGATCGCCAGCCACACCGCCTTCGCCGCCA<br>AGGCCGGCCTGATGAGGCACACCATCGGCCAGGCCGAGCAGCAGGCCATGAGCGCCCAGGC<br>CTTCCACCAGGGCGAGAGCGCCGCCGCCTTCCAGGGCGCCCACGCCAGGTTCGTGGCCGCC<br>GCCGCCAAGGTGAACACCCTGCTGGACATCGCCCAGGCCAACCTGGGCGAGGCCGCCGGCA<br>CCTACGTGGCCGCCGACGCCGCCGCCGCCAGCAGCTACACCGGCTTCTGA<br>(SEQ ID NO: 36)<br>MSLLDAHIPQLIASHTAFAAKAGLMRHTIGQAEQQAMSAQAFHQGESAAAFQGAHARFVAA<br>AAKVNTLLDIAQANLGEAAGTYVAADAAAASSYTGF(SEQ ID NO: 37) |
| Rv3019c<br>(esxR) | ATGAGCCAGATCATGTACAACTACCCCGCCATGATGGCCCACGCCGGCGACATGGCCGGCT<br>ACGCCGGCACCCTGCAGAGCCTGGGCGCCGACATCGCCAGCGAGCAGGCCGTGCTGAGCAG<br>CGCCTGGCAGGGCGACACCGGCATCACCTACCAGGGCTGGCAGACCCAGTGGAACCAGGCC<br>CTGGAGGACCTGGTGAGGGCCTACCAGAGCATGAGCGGCACCCACGAGAGCAACACCATGG<br>CCATGCTGGCCAGGGACGGCGCCGAGGCCGCCAAGTGGGGCGGCTGA<br>(SEQ ID NO: 38)<br>MSQIMYNYPAMMAHAGDMAGYAGTLQSLGADIASEQAVLSSAWQGDTGITYQGWQTQWNQA<br>LEDLVRAYQSMSGTHESNTMAMLARDGAEEAAKWGG (SEQ ID NO: 39) |
| Rv3891c<br>(esxD) | GTGGCCGACACCATCCAGGTGACCCCCCAGATGCTGAGGAGCACCGCCAACGACATCCAGG<br>CCAACATGGAGCAGGCCATGGGCATCGCCAAGGGCTACCTGGCCAACCAGGAGAACGTGAT<br>GAACCCCGCCACCTGGAGCGGCACCGGCGTGGTGGCCAGCCACATGACCGCCACCGAGATC<br>ACCAACGAGCTGAACAZAGGTGCTGACCGGCGGCACCAGGCTGGCCGAGGGCCTGGTGCAG<br>GCCGCCGCCCTGATGGAGGGCCACGAGGCCGACAGCCAGACCGCCTTCCAGGCCCTGTTCG<br>GCGCCAGCCACGGCAGCTGA (SEQ ID NO: 40)<br>VADTIQVTPQMLRSTANDIQANMEQAMGIAKGYLANQENVMNPATWSGTGVVASHMTATEI<br>TNELNKVLTGGTRLAEGLVQAAALMEGHEADSQTAFQALFGASHGS<br>(SEQ ID NO: 41) |
| Rv2346c<br>(esxO) | ATGACCATCAACTACCAGTTCGGCGACGTGGACGCCCACGGCGCCATGATCAGGGCCCAGG<br>CCGGCCTGCTGGAGGCCGAGCACCAGGCCATCGTGAGGGACGTGCTGGCCGCCGGCGACTT<br>CTGGGGCGGCGCCGGCAGCGTGGCCTGCCAGGAGTTCATCACCCAGCTGGGCAGGAACTTC<br>CAGGTGATCTACGAGCAGGCCAACGCCCACGGCCAGAAGGTGCAGGCCGCCGGCAACAACA<br>TGGCCCAGACCGACAGCGCCGTGGGCAGCAGCTGGGCCTGA (SEQ ID NO: 42)<br>MTINYQFGDVDAHGAMIRAQAGLLEAEHQAIVRDVLAAGDFWGGAGSVACQEFITQLGRNF<br>QVIYEQANAHGQKVQAAGNNMAQTDSAVGSSWA(SEQ ID NO: 43) |
| Rv3445c<br>(esxU) | GTGAGCACCCCCAACACCCTGAACGCCGACTTCGACCTGATGAGGAGCGTGGCCGGCATCA<br>CCGACGCCAGGAACGAGGAGATCAGGGCCATGCTGCAGGCCTTCATCGGCAGGATGAGCGG<br>CGTGCCCCCCAGCGTGTGGGGCGGCCTGGCCGCCGCCAGGTTCCAGGACGTGGTGGACAGG<br>TGGAACGCCGAGAGCACCAGGCTGTACCACGTGCTGCACGCCATCGCCGACACCATCAGGC<br>ACAACGAGGCCGCCCTGAGGGAGGCCGGCCAGATCCACGCCAGGCACATCGCCGCCGCCGG<br>CGGCGACCTGTGA (SEQ ID NO: 44)<br>VSTPNTLNADFDLMRSVAGITDARNEEIRAMLQAFIGRMSGVPPSVWGGLAAARFQDVVDR<br>WNAESTRLYHVLHAIADTIRHNEAALREAGQIHARHIAAAGGDL(SEQ ID NO: 45) |
| Rv3619c<br>(esxV) | ATGACCATCAACTACCAGTTCGGCGACGTGGACGCCCACGGCGCCATGATCAGGGCCCAGG<br>CCGGCAGCCTGGAGGCCGAGCACCAGGCCATCATCAGCGACGTGCTGACCGCCAGCGACTT<br>CTGGGGCGGCGCCGGCAGCGCCGCCTGCCAGGGCTTCATCACCCAGCTGGGCAGGAACTTC<br>CAGGTGATCTACGAGCAGGCCAACGCCCACGGCCAGAAGGTGCAGGCCGCCGGCAACAACA<br>TGGCCCAGACCGACAGCGCCGTGGGCAGCAGCTGGGCCTGA (SEQ ID NO: 46)<br>MTINYQFGDVDAHGAMIRAQAGSLEAEHQAIISDVLTASDFWGGAGSAACQGFITQLGRNF<br>QVIYEQANAHGQKVQAAGNNMAQTDSAVGSSWA(SEQ ID NO: 47) |
| Rv3875<br>(esxA, ESAT6) | ATGACCGAGCAGCAGTGGAACTTCGCCGGCATCGAGGCCGCCGCCAGCGCCATCCAGGGCA<br>ACGTGACCAGCATCCACAGCCTGCTGGACGAGGGCAAGCAGAGCCTGACCAAGCTGGCCGC<br>CGCCTGGGGCGGCAGCGGCAGCGAGGCCTACCAGGGCGTGCAGCAGAAGTGGGACGCCACC<br>GCCACCGAGCTGAACAACGCCCTGCAGAACCTGGCCAGGACCATCAGCGAGGCCGGCCAGG<br>CCATGGCCAGCACCGAGGGCAACGTGACCGGCATGTTCGCCTGA (SEQ ID NO: 48)<br>MTEQQWNFAGIEAAASAIQGNVTSIHSLLDEGKQSLTKLAAAWGGSGSEAYQGVQQKWDAT<br>ATELNNALQNLARTISEAGQAMASTEGNVTGMFA(SEQ ID NO: 49) |
| Rv3874<br>(esxB, CFP10) | ATGGCCGAGATGAAGACCGACGCCGCCACCCTGGCCCAGGAGGCCGGCAACTTCGAGAGGA<br>TCAGCGGCGACCTGAAGACCCAGATCGACCAGGTGGAGAGCACCGCCGGCAGCCTGCAGGG<br>CCAGTGGAGGGGCGCCGCCGGCACCGCCGCCCAGGCCGCCGTGGTGAGGTTCCAGGAGGCC |

TABLE 5-continued

ESX Antigens

| Construct | nucleotide sequence<br>amino acid sequence |
|---|---|
| | GCCAACAAGCAGAAGCAGGAGCTGGACGAGATCAGCACCAACATCAGGCAGGCCGGCGTGC<br>AGTACAGCAGGGCCGACGAGGAGCAGCAGCAGGCCCTGAGCAGCCAGATGGGCTTCTGA<br>(SEQ ID NO: 50)<br>MAEMKTDAATLAQEAGNFERISGDLKTQIDQVESTAGSLQGQWRGAAGTAAQAAVVRFQEA<br>ANKQKQELDEISTNIRQAGVQYSRADEEQQQALSSQMGF (SEQ ID NO: 51) |

In some embodiments, a composition comprises at least two of the ESX antigens. In some embodiments, the composition comprises at least three of the ESX antigens. In some embodiments, the composition comprises at least four of the ESX antigens. In some embodiments, the composition comprises at least five of the ESX antigens. In some embodiments, the composition comprises at least six of the ESX antigens. In some embodiments, the composition comprises at least seven of the ESX antigens. In some embodiments, the composition comprises at least eight of the ESX antigens. In some embodiments, the composition comprises all nine ESX antigens. In some embodiments, the composition comprises from at least two to nine of the ESX antigens. In some embodiments, the composition comprises from at least three to nine of the ESX antigens. In some embodiments, the composition comprises from at least four to nine of the ESX antigens. In some embodiments, the composition comprises at least five to nine of the ESX antigens. In some embodiments, the composition comprises at least six to nine of the ESX antigens. In some embodiments, the composition comprises at least seven to nine of the ESX antigens. In some embodiments, the composition comprises eight or nine of the ESX antigens. In some embodiments, the composition further comprises a pharmaceutically acceptable carrier.

In some embodiments, the fusion protein comprises at least two of the ESX antigens. In some embodiments, the fusion protein comprises at least three of the ESX antigens. In some embodiments, the fusion protein comprises at least four of the ESX antigens. In some embodiments, the fusion protein comprises at least five of the ESX antigens. In some embodiments, the fusion protein comprises at least six of the ESX antigens. In some embodiments, the fusion protein comprises at least seven of the ESX antigens. In some embodiments, the fusion protein comprises at least eight of the ESX antigens. In some embodiments, the fusion protein comprises all nine ESX antigens. In some embodiments, the fusion protein comprises from at least two to nine of the ESX antigens. In some embodiments, the fusion protein comprises from at least three to nine of the ESX antigens. In some embodiments, the fusion protein comprises from at least four to nine of the ESX antigens. In some embodiments, the fusion protein comprises at least five to nine of the ESX antigens. In some embodiments, the fusion protein comprises at least six to nine of the ESX antigens. In some embodiments, the fusion protein comprises at least seven to nine of the ESX antigens. In some embodiments, the fusion protein comprises eight or nine of the ESX antigens.

In some embodiments, the fusion protein comprises Rv3017c, Rv3020c, Rv3019c, Rv3891c, Rv2346c, and Rv3445c. In some embodiments, the fusion protein comprises Rv3619c, Rv3875, and Rv3874.

In any of the embodiments of fusion proteins set forth herein, the individual ESX antigens can be present in any order. For example, for a fusion protein comprising Rv3619c, Rv3875, and Rv3874 antigens, the first (or N-terminal) antigen may be Rv3619c, Rv3875, or Rv3874; the second antigen may be Rv3619c, Rv3875, or Rv3874 (whichever one is not the first ESX antigen); and the third antigen may be Rv3619c, Rv3875, or Rv3874 (whichever one is not the first or second ESX antigen). Likewise for every fusion protein disclosed herein.

Individual ESX antigens may be linked together in a C-terminus to N-terminus or N-terminus to C-terminus manner without any linker. Alternately, a linker may be present between any two ESX antigens within any of the fusion proteins disclosed herein. In some embodiments, the linker is a segment of DNA or RNA optionally containing one or more restrictions sites, wherein the linker is inserted between nucleic acid molecules encoding two ESX antigens of any of the fusion proteins disclosed herein.

In some embodiments, the fusion protein comprises Rv3017c-Rv3020c-Rv3019c-Rv3891c-Rv2346c-Rv3445c (Construct D; see Table 6). The nucleotide sequence is SEQ ID NO:52, and the corresponding amino acid sequence is SEQ ID NO:53 (including a C-terminal HA tag (YPYDVPDYA; SEQ ID NO:17) added).

In some embodiments, the fusion protein comprises Rv3619c-Rv3875-Rv3874 (Construct E; see Table 6). The nucleotide sequence is SEQ ID NO:54, and the corresponding amino acid sequence is SEQ ID NO:55 (including a C-terminal HA tag (YPYDVPDYA; SEQ ID NO:17) added).

TABLE 6

ESX Antigen Cassette

| Construct | nucleotide sequence<br>amino acid sequence |
|---|---|
| D | GTGAGCCAGAGCATGTACAGCTACCCCGCCATGACCGCCAACGTGGGCGACATGGCCGGCT<br>ACACCGGCACCACCCAGAGCCTGGGCGCCGACATCGCCAGCGAGAGGACCGCCCCCAGCAG<br>GGCCTGCCAGGGCGACCTGGGCATGAGCCACCAGGACTGGCAGGCCCAGTGGAACCAGGCC<br>ATGGAGGCCCTGGCCAGGGCCTACAGGAGGTGCAGGAGGGCCCTGAGGCAGATCGGCGTGC<br>TGGAGAGGCCCGTGGGCGACAGCAGCGACTGCGGCACCATCAGGGTGGGCAGCTTCAGGGG<br>CAGGTGGCTGGACCCCAGGCACGCCGGCCCCGCCACCGCCGCCGACGCCGGCGACATGAGC |

TABLE 6-continued

ESX Antigen Cassette

| Construct | nucleotide sequence<br>amino acid sequence |
|---|---|
| | CTGCTGGACGCCCACATCCCCCAGCTGATCGCCAGCCACACCGCCTTCGCCGCCAAGGCCG<br>GCCTGATGAGGCACACCATCGGCCAGGCCGAGCAGCAGGCCATGAGCGCCCAGGCCTTCCA<br>CCAGGGCGAGAGCGCCGCCGCCTTCCAGGGCGCCCACGCCAGGTTCGTGGCCGCCGCCGCC<br>AAGGTGAACACCCTGCTGGACATCGCCCAGGCCAACCTGGGCGAGGCCGCCGGCACCTACG<br>TGGCCGCCGACGCCGCCGCCGCCAGCAGCTACACCGGCTTCATGAGCCAGATCATGTACAA<br>CTACCCCGCCATGATGGCCCACGCCGGCGACATGGCCGGCTACGCCGGCACCCTGCAGAGC<br>CTGGGCGCCGACATCGCCAGCGAGCAGGCCGTGCTGAGCAGCGCCTGGCAGGGCGACACCG<br>GCATCACCTACCAGGGCTGGCAGACCCAGTGGAACCAGGCCCTGGAGGACCTGGTGAGGGC<br>CTACCAGAGCATGAGCGGCACCCACGAGAGCAACACCATGGCCATGCTGGCCAGGGACGGC<br>GCCGAGGCCGCCAAGTGGGGCGGCGTGGCCGACACCATCCAGGTGACCCCCCAGATGCTGA<br>GGAGCACCGCCAACGACATCCAGGCCAACATGGAGCAGGCCATGGGCATCGCCAAGGGCTA<br>CCTGGCCAACCAGGAGAACGTGATGAACCCCGCCACCTGGAGCGGCACCGGCGTGGTGGCC<br>AGCCACATGACCGCCACCGAGATCACCAACGAGCTGAACAAGGTGCTGACCGGCGGCACCA<br>GGCTGGCCGAGGGCCTGGTGCAGGCCGCCGCCCTGATGGAGGGCCACGAGGCCGACAGCCA<br>GACCGCCTTCCAGGCCCTGTTCGGCGCCAGCCACGGCAGCATGACCATCAACTACCAGTTC<br>GGCGACGTGGACGCCCACGGCGCCATGATCAGGGCCCAGGCCGGCCTGCTGGAGGCCGAGC<br>ACCAGGCCATCGTGAGGGACGTGCTGGCCGCCGGCGACTTCTGGGGCGGCGCCGGCAGCGT<br>GGCCTGCCAGGAGTTCATCACCCAGCTGGGCAGGAACTTCCAGGTGATCTACGAGCAGGCC<br>AACGCCCACGGCCAGAAGGTGCAGGCCGCCGGCAACAACATGGCCCAGACCGACAGCGCCG<br>TGGGCAGCAGCTGGGCCGTGAGCACCCCCAACACCCTGAACGCCGACTTCGACCTGATGAG<br>GAGCGTGGCCGGCATCACCGACGCCAGGAACGAGGAGATCAGGGCCATGCTGCAGGCCTTC<br>ATCGGCAGGATGAGCGGCGTGCCCCCCAGCGTGTGGGGCGGCCTGGCCGCCGCCAGGTTCC<br>AGGACGTGGTGGACAGGTGGAACGCCGAGAGCACCAGGCTGTACCACGTGCTGCACGCCAT<br>CGCCGACACCATCAGGCACAACGAGGCCGCCCTGAGGGAGGCCGGCCAGATCCACGCCAGG<br>CACATCGCCGCCGCCGGCGGCGACCTGTACCCCTACGACGTGCCCGACTACGCCTGA<br>(SEQ ID NO: 52)<br>VSQSMYSYPAMTANVGDMAGYTGTTQSLGADIASERTAPSRACQGDLGMSHQDWQAQWNQA<br>MEALARAYRRCRRALRQIGVLERPVGDSSDCGTIRVGSFRGRWLDPRHAGPATAADAGDMS<br>LLDAHIPQLIASHTAFAAKAGLMRHTIGQAEQQAMSAQAFHQGESAAAFQGAHARFVAAAA<br>KVNTLLDIAQANLGEAAGTYVAADAAAASSYTGFMSQIMYNYPAMMAHAGDMAGYAGTLQS<br>LGADIASEQAVLSSAWQGDTGITYQGWQTQWNQALEDLVRAYQSMSGTHESNTMAMLARDG<br>AEAAKWGGVADTIQVTPQMLRSTANDIQANMEQAMGIAKGYLANQENVMNPATWSGTGVVA<br>SHMTATEITNELNKVLTGGTRLAEGLVQAAALMEGHEADSQTAFQALFGASHGSMTINYQF<br>GDVDAHGAMIRAQAGLLEAEHQAIVRDVLAAGDFWGGAGSVACQEFITQLGRNFQVIYEQA<br>NAHGQKVQAAGNNMAQTDSAVGSSWAVSTPNTLNADFDLMRSVAGITDARNEEIRAMLQAF<br>IGRMSGVPPSVWGGLAAARFQDVVDRWNAESTRLYHVLHAIADTIRHNEAALREAGQIHAR<br>HIAAAGGDLYPYDVPDYA (SEQ ID NO: 53) |
| E | ATGACCATCAACTACCAGTTCGGCGACGTGGACGCCCACGGCCCATGATCAGGGCCCAGGC<br>CGGCAGCCTGGAGGCCGAGCACCAGGCCATCATCAGCGACGTGCTGACCGCCAGCGACTTC<br>TGGGGCGGCGCCGGCAGCGCCGCCTGCCAGGGCTTCATCACCCAGCTGGGCAGGAACTTCC<br>AGGTGATCTACGAGCAGGCCAACGCCCACGGCCAGAAGGTGCAGGCCGCCGGCAACAACAT<br>GGCCCAGACCGACAGCGCCGTGGGCAGCAGCTGGGCCATGACCGAGCAGCAGTGGAACTTC<br>GCCGGCATCGAGGCCGCCGCCAGCGCCATCCAGGGCAACGTGACCAGCATCCACAGCCTGC<br>TGGACGAGGGCAAGCAGAGCCTGACCAAGCTGGCCGCCGCCTGGGGCGGCAGCGGCAGCGA<br>GGCCTACCAGGGCGTGCAGCAGAAGTGGGACGCCACCGCCACCGAGCTGAACAACGCCCTG<br>CAGAACCTGGCCAGGACCATCAGCGAGGCCGGCCAGGCCATGGCCAGCACCGAGGGCAACG<br>TGACCGGCATGTTCGCCATGGCCGAGATGAAGACCGACGCCGCCACCCTGGCCCAGGAGGC<br>CGGCAACTTCGAGAGGATCAGCGGCGACCTGAAGACCCAGATCGACCAGGTGGAGAGCACC<br>GCCGGCAGCCTGCAGGGCCAGTGGAGGGGCGCCGCCGGCACCGCCGCCCAGGCCGCCGTGG<br>TGAGGTTCCAGGAGGCCGCCAACAAGCAGAAGCAGGAGCTGGACGAGATCAGCACCAACAT<br>CAGGCAGGCCGGCGTGCAGTACAGCAGGGCCGACGAGGAGCAGCAGCAGGCCCTGAGCAGC<br>CAGATGGGCTTCTACCCCTACGACGTGCCCGACTACGCCTGA (SEQ ID NO: 54)<br>MTINYQFGDVDAHGAMIRAQAGSLEAEHQAIISDVLTASDFWGGAGSAACQGFITQLGRNF<br>QVIYEQANAHGQKVQAAGNNMAQTDSAVGSSWAMTEQQWNFAGIEAAASAIQGNVTSIHSL<br>LDEGKQSLTKLAAAWGGSGSEAYQGVQQKWDATATELNNALQNLARTISEAGQAMASTEGN<br>VTGMFAMAEMKTDAATLAQEAGNFERISGDLKTQIDQVESTAGSLQGQWRGAAGTAAQAAV<br>VRFQEAANKQKQELDEISTNIRQAGVQYSRADEEQQQALSSQMGFYPYDVPDYA<br>(SEQ ID NO: 55) |

In some embodiments, the Mtb antigen is a variable antigen. In some embodiments, the variable antigen is Rv2719c, Rv0010c, Rv1872c, Rv0012, Rv0990c, or Rv0995.

A nucleotide sequence encoding Rv2719c is shown in Table 7 as SEQ ID NO:56, and an amino acid sequence of Rv2719c is shown in Table 7 as SEQ ID NO:57.

A nucleotide sequence encoding Rv0010c is shown in Table 7 as SEQ ID NO:58, and an amino acid sequence of Rv0010c is shown in Table 7 as SEQ ID NO:59.

A nucleotide sequence encoding Rv1872c is shown in Table 7 as SEQ ID NO:60, and an amino acid sequence of Rv1872c is shown in Table 7 as SEQ ID NO:61.

A nucleotide sequence encoding Rv0012 is shown in Table 7 as SEQ ID NO:62, and an amino acid sequence of Rv0012 is shown in Table 7 as SEQ ID NO:63.

A nucleotide sequence encoding Rv0990c is shown in Table 7 as SEQ ID NO:64, and an amino acid sequence of Rv0990c is shown in Table 7 as SEQ ID NO:65.

A nucleotide sequence encoding Rv0995 is shown in Table 7 as SEQ ID NO:66, and an amino acid sequence of Rv0995 is shown in Table 7 as SEQ ID NO:67.

TABLE 7

Variable Antigens

| Construct | Nucleotide sequence<br>amino acid sequence |
|---|---|
| Rv2719c | ATGACCCCCGTGAGGCCCCCCACACCCCCGACCCCCTGAACCTGAGGGGCCCCCTGGACGGC<br>CCCAGGTGGAGGAGGGCCGAGCCCGCCCAGAGCAGGAGGCCCGGCAGGAGCAGGCCCGGCGGC<br>GCCCCCCTGAGGTACCACAGGACCGGCGTGGGCATGAGCAGGACCGGCCACGGCAGCAGGCCC<br>GTGCCCCCCGCCACCACCGTGGGCCTGGCCCTGCTGGCCGCCGCCATCACCCTGTGGCTGGGC<br>CTGGTGGCCCAGTTCGGCCAGATGATCACCGGCGGCAGCGCCGACGGCAGCGCCGACAGCACC<br>GGCAGGGTGCCCGACAGGCTGGCCGTGGTGAGGGTGGAGACCGGCGAGAGCCTGTACGACGTG<br>GCCGTGAGGGTGGCCCCCAACGCCCCCACCAGGCAGGTGGCCGACAGGATCAGGGAGCTGAAC<br>GGCCTGCAGACCCCCGCCCTGGCCGTGGGCCAGACCCTGATCGCCCCCGTGGGCTGA<br>(SEQ ID NO: 56)<br>MTPVRPPHTPDPLNLRGPLDGPRWRRAEPAQSRRPGRSRPGGAPLRYHRTGVGMSRTGHGSRP<br>VPPATTVGLALLAAAITLWLGLVAQFGQMITGGSADGSADSTGRVPDRLAVVRVETGESLYDV<br>AVRVAPNAPTRQVADRIRELNGLQTPALAVGQTLIAPVG (SEQ ID NO: 57) |
| Rv0010c | ATGCAGCAGACCGCCTGGGCCCCCAGGACCAGCGGCATCGCCGGCTGCGGCGCCGGCGGCGTG<br>GTGATGGCCATCGCCAGCGTGACCCTGGTGACCGACACCCCCGGCAGGGTGCTGACCGGCGTG<br>GCCGCCCTGGGCCTGATCCTGTTCGCCAGCGCCACCTGGAGGGCCAGGCCCAGGCTGGCCATC<br>ACCCCCGACGGCCTGGCCATCAGGGGCTGGTTCAGGACCCAGCTGCTGAGGCACAGCAACATC<br>AAGATCATCAGGATCGACGAGTTCAGGAGGTACGGCAGGCTGGTGAGGCTGCTGGAGATCGAG<br>ACCGTGAGCGGCGGCCTGCTGATCCTGAGCAGGTGGGACCTGGGCACCGACCCCGTGGAGGTG<br>CTGGACGCCCTGACCGCCGCCGGCTACGCCGGCAGGGGCCAGAGGTGA<br>(SEQ ID NO: 58)<br>MQQTAWAPRTSGIAGCGAGGVVMAIASVTLVTDTPGRVLTGVAALGLILFASATWRARPRLAI<br>TPDGLAIRGWFRTQLLRHSNIKIIRIDEFRRYGRLVRLLEIETVSGGLLILSRWDLGTDPVEV<br>LDALTAAGYAGRGQR (SEQ ID NO: 59) |
| Rv1872c | ATGGCCGTGAACAGGAGGGTGCCCAGGGTGAGGGACCTGGCCCCCCTGCTGCAGTTCAACAGG<br>CCCCAGTTCGACACCAGCAAGAGGAGGCTGGGCGCCGCCCTGACCATCCAGGACCTGAGGAGG<br>ATCGCCAAGAGGAGGACCCCCAGGGCCGCCTTCGACTACGCCGACGGCGGCGCCGAGGACGAG<br>CTGAGCATCGCCAGGGCCAGGCAGGGCTTCAGGGACATCGAGTTCCACCCCACCATCCTGAGG<br>GACGTGACCACCGTGTGCGCCGGCTGGAACGTGCTGGGCCAGCCCACCGTGCTGCCCTTCGGC<br>ATCGCCCCCACCGGCTTCACCAGGCTGATGCACACCGAGGGCGAGATCGCCGGCGCCAGGGCC<br>GCCGCCGCCGCCGGCATCCCCTTCAGCCTGAGCACCCTGGCCACCTGCGCCATCGAGGACCTG<br>GTGATCGCCGTGCCCCAGGGCAGGAAGTGGTTCCAGCTGTACATGTGGAGGGACAGGGACAGG<br>AGCATGGCCCTGGTGAGGAGGGTGGCCGCCGCCGGCTTCGACACCATGCTGGTGACCGTGGAC<br>GTGCCCGTGGCCGGCGCCAGGCTGAGGGACGTGAGGAACGGCATGAGCATCCCCCCCGCCCTG<br>ACCCTGAGGACCGTGCTGGACGCCATGGGCCACCCCAGGTGGTGGTTCGACCTGCTGACCACC<br>GAGCCCCTGGCCTTCGCCAGCCTGGACAGGTGGCCCGGCACCGTGGGCGAGTACCTGAACACC<br>GTGTTCGACCCCAGCCTGACCTTCGACGACCTGGCCTGGATCAAGAGCCAGTGGCCCGGCAAG<br>CTGGTGGTGAAGGGCATCCAGACCCTGGACGACGCCAGGGCCGTGGTGGACAGGGGCGTGGAC<br>GGCATCGTGCTGAGCAACCACGGCGGCAGGCAGCTGGACAGGGCCCCCGTGCCCTTCCACCTG<br>CTGCCCCACGTGGCCAGGGAGCTGGGCAAGCACACCGAGATCCTGGTGGACACCGGCATCATG<br>AGCGGCGCCGACATCGTGGCCGCCATCGCCCTGGGCGCCAGGTGCACCCTGATCGGCAGGGCC<br>TACCTGTACGGCCTGATGGCCGGCGGCGAGGCCGGCGTGAACAGGGCCATCGAGATCCTGCAG<br>ACCGGCGTGATCAGGACCATGAGGCTGCTGGGCGTGACCTGCCTGGAGGAGCTGAGCCCCAGG<br>CACGTGACCCAGCTGAGGAGGCTGGGCCCCATCGGCGCCCCCACCTGA<br>(SEQ ID NO: 60)<br>MAVNRRVPRVRDLAPLLQFNRPQFDTSKRRLGAALTIQDLRRIAKRRTPRAAFDYADGGAEDE<br>LSIARARQGFRDIEFHPTILRDVTTVCAGWNVLGQPTVLPFGIAPTGFTRLMHTEGEIAGARA<br>AAAAGIPFSLSTLATCAIEDLVIAVPQGRKWFQLYMWRDRDRSMALVRRVAAAGFDTMLVTVD<br>VPVAGARLRDVRNGMSIPPALTLRTVLDAMGHPRWWFDLLTTEPLAFASLDRWPGTVGEYLNT<br>VFDPSLTFDDLAWIKSQWPGKLVVKGIQTLDDARAVVDRGVDGIVLSNHGGRQLDRAPVPFHL<br>LPHVARELGKHTEILVDTGIMSGADIVAAIALGARCTLIGRAYLYGLMAGGEAGVNRAIEILQ<br>TGVIRTMRLLGVTCLEELSPRHVTQLRRLGPIGAPT (SEQ ID NO: 61) |
| Rv0012 | ATGAGGCTGACCCACCCCACCCCCTGCCCCGAGAACGGCGAGACCATGATCGACAGGAGGAGG<br>AGCGCCTGGAGGTTCAGCGTGCCCCTGGTGTGCCTGCTGGCCGGCCTGCTGCTGGCCGCCACC<br>CACGGCGTGAGCGGCGGCACCGAGATCAGGAGGAGCGACGCCCCCAGGCTGGTGGACCTGGTG<br>AGGAGGGCCCAGGCCAGCGTGAACAGGCTGGCCACCGAGAGGGAGGCCCTGACCACCAGGATC<br>GACAGCGTGCACGGCAGGAGCGTGGACACCGCCCTGGCCGCCATGCAGAGGAGGAGCGCCAAG<br>CTGGCCGGCGTGGCCGCCATGAACCCCGTGCACGGCCCCGGCCTGGTGGTGACCCTGCAGGAC<br>GCCCAGAGGGACGCCAACGGCAGGTTCCCCAGGGACGCCAGCCCCGACGACCTGGTGGTGCAC<br>CAGCAGGACATCGAGGCCGTGCTGAACGCCCTGTGGAACGCCGGCGCCGAGGCCATCCAGATG<br>CAGGACCAGAGGATCATCGCCATGAGCATCGCCAGGTGCGTGGGCAACACCCTGCTGCTGAAC<br>GGCAGGACCTACAGCCCCCCCTACACCATCGCCGCCATCGGCGACGCCGCCGCCATGCAGGCC<br>GCCCTGGCCGCCGCCCCCCTGGTGACCCTGTACAAGCAGTACGTGGTGAGGTTCGGCCTGGGC<br>TACTGCGAGGAGGTGCACCCCGACCTGCAGATCGTGGGCTACGCCGACCCCGTGAGGATGCAC<br>TTCGCCCAGCCCGCCGGCCCCCTGGACTACTGA (SEQ ID NO: 62)<br>MRLTHPTPCPENGETMIDRRRSAWRFSVPLVCLLAGLLLAATHGVSGGTEIRRSDAPRLVDLV<br>RRAQASVNRLATEREALTTRIDSVHGRSVDTALAAMQRRSAKLAGVAAMNPVHGPGLVVTLQD<br>AQRDANGRFPRDASPDDLVVHQQDIEAVLNALWNAGAEAIQMQDQRIIAMSIARCVGNTLLLN<br>GRTYSPPYTIAAIGDAAAMQAALAAAPLVTLYKQYVVRFGLGYCEEVHPDLQIVGYADPVRMH<br>FAQPAGPLDY (SEQ ID NO: 63) |

TABLE 7-continued

Variable Antigens

| Construct | Nucleotide sequence<br>amino acid sequence |
|---|---|
| Rv0990c | GTGGCCGAGAGCAGCCTGAACCCCAGCCTGGTGAGCAGGATCAGCGCCTTCCTGAGGCCCGAC<br>TGGACCAGGACCGTGAGGGCCAGGAGGTTCGCCGCCGCCGGCCTGGTGATGCTGGCCGGCGTG<br>GCCGCCCTGAGGAGCAACCCCGAGGACGACAGGAGCGAGGTGGTGGTGGCCGCCCACGACCTG<br>AGGCCCGGCACCGCCCTGACCCCGGCGACGTGAGGCTGGAGAAGAGGAGCGCCACCACCCTGC<br>CCGACGGCAGCCAGGCCGACCTGGACGCCGTGGTGGGCAGCACCCTGGCCAGCCCCACCAGGA<br>GGGGCGAGGTGCTGACCGACGTGAGGCTGCTGGGCAGCAGGCTGGCCGAGAGCACCGCCGGCC<br>CCGACGCCAGGATCGTGCCCCTGCACCTGGCCGACAGCGCCCTGGTGGACCTGGTGAGGGTGG<br>GCGACGTGGTGGACGTGCTGGCCGCCCCCGTGACCGACAGCCCCGCCGCCCTGAGGCTGCTGG<br>CCACCGACGCCATCGTGGTGCTGGTGAGCGCCCAGCAGAAGGCCCAGGCCGCCGACAGCGACA<br>GGGTGGTGCTGGTGGCCCTGCCCGCCAGGCTGGCCAACACCGTGGCCGGCGCCGCCCTGGGCC<br>AGACCGTGACCCTGACCCTGCACTGA (SEQ ID NO: 64)<br>VAESSLNPSLVSRISAFLRPDWTRTVRARRFAAAGLVMLAGVAALRSNPEDDRSEVVVAAHDL<br>RPGTALTPGDVRLEKRSATTLPDGSQADLDAVVGSTLASPTRRGEVLTDVRLLGSRLAESTAG<br>PDARIVPLHLADSALVDLVRVGDVVDVLAAPVTDSPAALRLLATDAIVVLVSAQQKAQAADSD<br>VVLVALPARLANTVAGAALGQTVTLTLH (SEQ ID NO: 65) |
| Rv0995 | ATGGCCGTGGGCCCCCTGAGGGTGAGCGCCGGCGTGATCAGGCTGAGGCCCGTGAGGATGAGG<br>GACGGCGTGCACTGGAGCAGGATCAGGCTGGCCGACAGGGCCCACCTGGAGCCCTGGGAGCCC<br>AGCGCCGACGGCGAGTGGACCGTGAGGCACACCGTGGCCGCCTGGCCCGCCGTGTGCAGCGGC<br>CTGAGGAGCGAGGCCAGGAACGGCAGGATGCTGCCCTACGTGATCGAGCTGGACGGCCAGTTC<br>TGCGGCCAGCTGACCATCGGCAACGTGACCCACGGCGCCCTGAGGAGCGCCTGGATCGGCTAC<br>TGGGTGCCCAGCGCCGCCACCGGCGGCGGCGTGGCCACCGGCGCCCTGGCCCTGGGCCTGGAC<br>CACTGCTTCGGCCCCGTGATGCTGCACAGGGTGGAGGCCACCGTGAGGCCCGAGAACGCCGCC<br>AGCAGGGCCGTGCTGGCCAAGGTGGGCTTCAGGGAGGAGGGCCTGCTGAGGAGGTACCTGGAG<br>GTGGACAGGGCCTGGAGGGACCACCTGCTGATGGCCATCACCGTGGAGGAGGTGTACGGCAGC<br>GTGGCCAGCACCCTGGTGAGGGCCGGCCACGCCAGCTGGCCCTGA (SEQ ID NO: 66)<br>MAVGPLRVSAGVIRLRPVRMRDGVHWSRIRLADRAHLEPWEPSADGEWTVRHTVAAWPAVCSG<br>LRSEARNGRMLPYVIELDGQFCGQLTIGNVTHGALRSAWIGYWVPSAATGGGVATGALALGLD<br>HCFGPVMLHRVEATVRPENAASRAVLAKVGFREEGLLRRYLEVDRAWRDHLLMAITVEEVYGS<br>VASTLVRAGHASWP (SEQ ID NO: 67) |

In some embodiments, a composition comprises at least two of the variable antigens. In some embodiments, the composition comprises at least three of the variable antigens. In some embodiments, the composition comprises at least four of the variable antigens. In some embodiments, the composition comprises at least five of the variable antigens. In some embodiments, the composition comprises all six variable antigens. In some embodiments, the composition comprises from at least two to six of the variable antigens. In some embodiments, the composition comprises from at least three to six of the variable antigens. In some embodiments, the composition comprises from at least four to six of the variable antigens. In some embodiments, the composition comprises five or six of the variable antigens. In some embodiments, the composition further comprises a pharmaceutically acceptable carrier.

In some embodiments, the fusion protein comprises at least two of the variable antigens. In some embodiments, the fusion protein comprises at least three of the variable antigens. In some embodiments, the fusion protein comprises at least four of the variable antigens. In some embodiments, the fusion protein comprises at least five of the variable antigens. In some embodiments, the fusion protein comprises all six variable antigens. In some embodiments, the fusion protein comprises from at least two to six of the variable antigens. In some embodiments, the fusion protein comprises from at least three to six of the variable antigens. In some embodiments, the fusion protein comprises from at least four to six of the variable antigens. In some embodiments, the fusion protein comprises five or six of the variable antigens.

In some embodiments, the fusion protein comprises Rv2719c, Rv0010c, and Rv1872c. In some embodiments, the fusion protein comprises Rv0012, Rv0990c, and Rv0995.

In any of the embodiments of fusion proteins set forth herein, the individual variable antigens can be present in any order. For example, for a fusion protein comprising Rv0012, Rv0990c, and Rv0995 antigens, the first (or N-terminal) antigen may be Rv0012, Rv0990c, or Rv0995; the second antigen may be Rv0012, Rv0990c, or Rv0995 (whichever one is not the first variable antigen); and the third antigen may be Rv0012, Rv0990c, or Rv0995 (whichever one is not the first or second variable antigen). Likewise for every fusion protein disclosed herein.

Individual variable antigens may be linked together in a C-terminus to N-terminus or N-terminus to C-terminus manner without any linker. Alternately, a linker may be present between any two variable antigens within any of the fusion proteins disclosed herein. In some embodiments, the linker is a segment of DNA or RNA optionally containing one or more restrictions sites, wherein the linker is inserted between nucleic acid molecules encoding two variable antigens of any of the fusion proteins disclosed herein.

In some embodiments, the fusion protein comprises Rv2719c-Rv0010c-Rv1872c (Construct F; see Table 8). The nucleotide sequence is SEQ ID NO:68, and the corresponding amino acid sequence is SEQ ID NO:69 (including a C-terminal HA tag (YPYDVPDYA; SEQ ID NO:17) added).

In some embodiments, the fusion protein comprises Rv0012-Rv0990c-Rv0995 (Construct G; see Table 8). The nucleotide sequence is SEQ ID NO:70, and the corresponding amino acid sequence is SEQ ID NO:71 (including a C-terminal HA tag (YPYDVPDYA; SEQ ID NO:17) added).

TABLE 8

Variable Antigen Cassette

| Construct | nucleotide sequence<br>amino acid sequence |
|---|---|
| F | ATGACCCCCGTGAGGCCCCCCACACCCCCGACCCCCTGAACCTGAGGGGCCCCCTGGACGGC<br>CCCAGGTGGAGGAGGGCCGAGCCCGCCCAGAGCAGGAGGCCCGGCAGGAGCAGGCCCGGCGGC<br>GCCCCCCTGAGGTACCACAGGACCGGCGTGGGCATGAGCAGGACCGGCCACGGCAGCAGGCCC<br>GTGCCCCCGCCACCACCGTGGGCCTGGCCCTGCTGGCCGCCGCCATCACCCTGTGGCTGGGC<br>CTGGTGGCCCAGTTCGGCCAGATGATCACCGGCGGCAGCGCCGACGGCAGCGCCGACAGCACC<br>GGCAGGGTGCCCGACAGGCTGGCCGTGGTGAGGGTGGAGACCGGCGAGAGCCTGTACGACGTG<br>GCCGTGAGGGTGGCCCCCAACGCCCCCACCAGGCAGGTGGCCGACAGGATCAGGGAGCTGAAC<br>GGCCTGCAGACCCCCGCCCTGGCCGTGGGCCAGACCCTGATCGCCCCCGTGGGCATGCAGCAG<br>ACCGCCTGGGCCCCAGGACCAGCGGCATCGCCGGCTGCGGCGCCGGCGGCGTGGTGATGGCC<br>ATCGCCAGCGTGACCCTGGTGACCGACACCCCCGGCAGGGTGCTGACCGGCGTGGCCGCCCTG<br>GGCCTGATCCTGTTCGCCAGCGCCACCTGGAGGGCCAGGCCCAGGCTGGCCATCACCCCCGAC<br>GGCCTGGCCATCAGGGGCTGGTTCAGGACCCAGCTGCTGAGGCACAGCAACATCAAGATCATC<br>AGGATCGACGAGTTCAGGAGGTACGGCAGGCTGGTGAGGCTGCTGGAGATCGAGACCGTGAGC<br>GGCGGCCTGCTGATCCTGAGCAGGTGGGACCTGGGCACCGACCCCGTGGAGGTGCTGGACGCC<br>CTGACCGCCGCCGGCTACGCCGGCAGGGGCCAGAGGATGGCCGTGAACAGGAGGGTGCCCAGG<br>GTGAGGGACCTGGCCCCCCTGCTGCAGTTCAACAGGCCCCAGTTCGACACCAGCAAGAGGAGG<br>CTGGGCGCCGCCCTGACCATCCAGGACCTGAGGAGGATCGCCAAGAGGAGGACCCCCAGGGCC<br>GCCTTCGACTACGCCGACGGCGGCGCCGAGGACGAGCTGAGCATCGCCAGGGCCAGGCAGGGC<br>TTCAGGGACATCGAGTTCCACCCCACCATCCTGAGGGACGTGACCACCGTGTGCGCCGGCTGG<br>AACGTGCTGGGCCAGCCCACCGTGCTGCCCTTCGGCATCGCCCCCACCGGCTTCACCAGGCTG<br>ATGCACACCGAGGGCGAGATCGCCGGCGCCAGGGCCGCCGCCGCCGCCGGCATCCCCTTCAGC<br>CTGAGCACCCTGGCCACCTGCGCCATCGAGGACCTGGTGATCGCCGTGCCCCAGGGCAGGAAG<br>TGGTTCCAGCTGTACATGTGGAGGGACAGGGACAGGAGCATGGCCCTGGTGAGGAGGGTGGCC<br>GCCGCCGGCTTCGACACCATGCTGGTGACCGTGGACGTGCCCGTGGCCGGCGCCAGGCTGAGG<br>GACGTGAGGAACGGCATGAGCATCCCCCCCGCCCTGACCCTGAGGACCGTGCTGGACGCCATG<br>GGCCACCCCAGGTGGTGGTTCGACCTGCTGACCACCGAGCCCCTGGCCTTCGCCAGCCTGGAC<br>AGGTGGCCCGGCACCGTGGGCGAGTACCTGAACACCGTGTTCGACCCCAGCCTGACCTTCGAC<br>GACCTGGCCTGGATCAAGAGCCAGTGGCCCGGCAAGCTGGTGGTGAAGGGCATCCAGACCCTG<br>GACGACGCCAGGGCCGTGGTGGACAGGGGCGTGGACGGCATCGTGCTGAGCAACCAGGCGGCA<br>GGCAGCTGGACAGGGCCCCCGTGCCCTTCCACCTGCTGCCCCACGTGGCCAGGGAGCTGGGCA<br>AGCACACCGAGATCCTGGTGGACACCGGCATCATGAGCGGCGCCGACATCGTGGCCGCCATCG<br>CCCTGGGCGCCAGGTGCACCCTGATCGGCAGGGCCTACCTGTACGGCCTGATGGCCGGCGGCG<br>AGGCCGGCGTGAACAGGGCCATCGAGATCCTGCAGACCGGCGTGATCAGGACCATGAGGCTGC<br>TGGGCGTGACCTGCCTGGAGGAGCTGAGCCCCAGGCACGTGACCCAGCTGAGGAGGCTGGGCC<br>CCATCGGCGCCCCCACCTACCCCTACGACGTGCCCGACTACGCCTGA<br>(SEQ ID NO: 68)<br>MTPVRPPHTPDPLNLRGPLDGPRWRRAEPAQSRRPGRSRPGGAPLRYHRTGVGMSRTGHGSRP<br>VPPATTVGLALLAAAITLWLGLVAQFGQMITGGSADGSADSTGRVPDRLAVVRVETGESLYDV<br>AVRVAPNAPTRQVADRIRELNGLQTPALAVGQTLIAPVGMQQTAWAPRTSGIAGCGAGGVVMA<br>IASVTLVTDTPGRVLTGVAALGLILFASATWRARPRLAITPDGLAIRGWFRTQLLRHSNIKII<br>RIDEFRRYGRLVRLLEIETVSGGLLILSRWDLGTDPVEVLDALTAAGYAGRGQRMAVNRRVPR<br>VRDLAPLLQFNRPQFDTSKRRLGAALTIQDLRRIAKRRTPRAAFDYADGGAEDELSIARARQG<br>FRDIEFHPTILRDVTTVCAGWNVLGQPTVLPFGIAPTGFTRLMHTEGEIAGARAAAAAGIPFS<br>LSTLATCAIEDLVIAVPQGRKWFQLYMWRDRDRSMALVRRVAAAGFDTMLVTVDVPVAGARLR<br>DVRNGMSIPPALTLRTVLDAMGHPRWWFDLLTTEPLAFASLDRWPGTVGEYLNTVFDPSLTFD<br>DLAWIKSQWPGKLVVKGIQTLDDARAVVDRGVDGIVLSNHGGRQLDRAPVPFHLLPHVARELG<br>KHTEILVDTGIMSGADIVAAIALGARCTLIGRAYLYGLMAGGEAGVNRAIEILQTGVIRTMRL<br>LGVTCLEELSPRHVTQLRRLGPIGAPTYPYDVPDYA (SEQ ID NO: 69) |
| G | ATGAGGCTGACCCACCCCACCCCCTGCCCCGAGAACGGCGAGACCATGATCGACAGGAGGAGG<br>AGCGCCTGGAGGTTCAGCGTGCCCCTGGTGTGCCTGCTGGCCGGCTGCTGCTGGCCGCCACCC<br>ACGGCGTGAGCGGCGGCACCGAGATCAGGAGGAGCGACGCCCCCAGGCTGGTGGACCTGGTGA<br>GGAGGGCCCAGGCCAGCGTGAACAGGCTGGCCACCGAGAGGGAGGCCCTGACCACCAGGATCG<br>ACAGCGTGCACGGCAGGAGCGTGGACACCGCCCTGGCCGCCATGCAGAGGAGGAGCGCCAAGC<br>TGGCCGGCGTGGCCGCCATGAACCCCGTGCACGGCCCCGGCCTGGTGGTGACCCTGCAGGACG<br>CCCAGAGGGACGCCAACGGCAGGTTCCCCAGGGACGCCAGCCCCGACGACCTGGTGGTGCACC<br>AGCAGGACATCGAGGCCGTGCTGAACGCCCTGTGGAACGCCGGCGCGGAGGCCATCCAGATGC<br>AGGACCAGAGGATCATCGCCATGAGCATCGCCAGGTGCGTGGGCAACACCCTGCTGCTGAACG<br>GCAGGACCTACAGCCCCCCCTACACCATCGCCGCCATCGGCGACGCCGCCGCCATGCAGGCCG<br>CCCTGGCCGCCGCCCCCTGGTGACCCTGTACAAGCAGTACGTGGTGAGGTTCGGCCTGGGCT<br>ACTGCGAGGAGGTGCACCCCGACCTGCAGATCGTGGGCTACGCCGACCCCGTGAGGATGCACT<br>TCGCCCAGCCCGCCGGCCCCCTGGACTACGTGGCCGAGAGGCCCTGAACCCCAGCCTGGTGA<br>GCAGGATCAGCGCCTTCCTGAGGCCCGACTGGACCAGGACCGTGAGGGCCAGGAGGTTCGCCG<br>CCGCCGGCCTGGTGATGCTGGCCGGCGTGGCCGCCCTGAGGAGCAACCCCGAGGACGACAGGA<br>GCGAGGTGGTGGTGGCCGCCCACGACCTGAGGCCCGGCACCGCCCTGACCCCCGGCGACGTGA<br>GGCTGGAGAAGAGGAGCGCCACCACCCTGCCCGACGGCAGCGGCGACCTGGACGCCGTGGTG<br>TGGGCAGCACCCTGGCCAGCCCCACCAGGAGGGGCGAGGTGCTGACCGACGTGAGGCTGCTGG<br>GCAGCAGGCTGGCCGAGAGCACCGCCGGCCCCGACGCCAGGATCGTGCCCCTGCACCTGGCCG<br>ACAGCGCCCTGGTGGACCTGGTGAGGGTGGGCGACGTGGTGGACGTGCTGGCCGCCCCCGTGA<br>CCGACAGCCCCGCCGCCCTGAGGCTGCTGGCCGACGCCGGCCATCGTGGTGCTGGTGAGCGCCC<br>AGCAGAAGGCCCAGGCCGCCGACAGCGACAGGGTGGTGCTGGTGGCCCTGCCCGCCAGGCTGG<br>CCAACACCGTGGCCGGCGCCGCCCTGGGCCAGACCGTGACCCTGACCCTGCACATGGCCGTGG<br>GCCCCCTGAGGGTGAGCGCCGGCGTGATCAGGCTGAGGCCCGTGAGGATGAGGGACGGCGTGC<br>ACTGGAGCAGGATCAGGCTGGCCGACAGGGCCCACCTGGAGCCCTGGGAGCCCAGCGCCGACG<br>GCGAGTGGACCGTGAGGCACACCGTGGCCGCCTGGCCCGCCGTGTGCAGCGGCCTGAGGAGCG |

TABLE 8-continued

Variable Antigen Cassette

| Construct | nucleotide sequence<br>amino acid sequence |
|---|---|
| | AGGCCAGGAACGGCAGGATGCTGCCCTACGTGATCGAGCTGGACGGCCAGTTCTGCGGCCAGC<br>TGACCATCGGCAACGTGACCCACGGCGCCCTGAGGAGCGCCTGGATCGGCTACTGGGTGCCCA<br>GCGCCGCCACCGGCGGCGGCGTGGCCACCGGCGCCCTGGCCCTGGGCCTGGACCACTGCTTCG<br>GCCCCGTGATGCTGCACAGGGTGGAGGCCACCGTGAGGCCCGAGAACGCCGCCAGCAGGGCCG<br>TGCTGGCCAAGGTGGGCTTCAGGGAGGAGGGCCTGCTGAGGAGGTACCTGGAGGTGGACAGGG<br>CCTGGAGGGACCACCTGCTGATGGCCATCACCGTGGAGGAGGTGTACGGCAGCGTGGCCAGCA<br>CCCTGGTGAGGGCCGGCCACGCCAGCTGGCCCTACCCCTACGACGTGCCCGACTACGCCTGA<br>(SEQ ID NO: 70)<br>MRLTHPTPCPENGETMIDRRRSAWRFSVPLVCLLAGLLLAATHGVSGGTEIRRSDAPRLVDLV<br>RRAQASVNRLATEREALTTRIDSVHGRSVDTALAAMQRRSAKLAGVAAMNPVHGPGLVVTLQD<br>AQRDANGRFPRDASPDDLVVHQQDIEAVLNALWNAGAEAIQMQDQRIIAMSIARCVGNTLLLN<br>GRTYSPPYTIAAIGDAAAMQAALAAAPLVTLYKQYVVRFGLGYCEEVHPDLQIVGYADPVRMH<br>FAQPAGPLDYVAESSLNPSLVSRISAFLRPDWTRTVRARRFAAAGLVMLAGVAALRSNPEDDR<br>SEVVVAAHDLRPGTALTPGDVRLEKRSATTLPDGSQADLDAVVGSTLASPTRRGEVLTDVRLL<br>GSRLAESTAGPDARIVPLHLADSALVDLVRVGDVVDVLAAPVTDSPAALRLLATDAIVVLVSA<br>QQKAQAADSDRVVLVALPARLANTVAGAALGQTVTLTLHMAVGPLRVSAGVIRLRPVRMRDGV<br>HWSRIRLADRAHLEPWEPSADGEWTVRHTVAAWPAVCSGLRSEARNGRMLPYVIELDGQFCGQ<br>LTIGNVTHGALRSAWIGYWVPSAATGGGVATGALALGLDHCFGPVMLHRVEATVRPENAASRA<br>VLAKVGFREEGLLRRYLEVDRAWRDHLLMAITVEEVYGSVASTLVRAGHASWPYPYDVPDYA<br>(SEQ ID NO: 71) |

Any Mtb antigen, including any Mtb antigen within any of the fusion proteins described herein, can have an amino acid sequence that is 100%, or from 70% to 99.9%, identical to the particular amino acid sequence listed in Tables 1 through 8. The amino acid sequence of any individual Mtb antigen, including any Mtb antigen within any of the fusion proteins described herein, can be at least 70%, at least 75%, at least 80%, at least 85%, at least 90%, at least 95%, at least 96%, at least 97%, at least 98%, or at least 99% identical to the particular amino acid sequence listed in Tables 1 through 8. Identity or similarity with respect to an amino acid or nucleotide sequence is defined herein as the percentage of amino acid residues (or nucleotide residues as the case may be) in the particular Mtb antigen that are identical (i.e., same residue) with the amino acid or nucleotide sequence for the Mtb antigen shown in Tables 1 through 8, after aligning the sequences and introducing gaps, if necessary, to achieve the maximum percent sequence identity. Percent sequence identity can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). Any amino acid number calculated as a % identity can be rounded up or down, as the case may be, to the closest whole number.

Any Mtb antigen, including any Mtb antigen within any of the fusion proteins described herein, can be fragments of the particular amino acid sequences listed in Tables 1, 3, 5, and 7. The amino acid sequence of any individual Mtb antigen, including any Mtb antigen within any of the fusion proteins described herein, can be missing consecutive amino acids constituting at least 20%, at least 15%, at least 10%, at least 5%, at least 4%, at least 3%, at least 2%, or at least 1%, of the particular amino acid sequences listed in Tables 1, 3, 5, and 7. The omitted consecutive amino acids may be from the C-terminus or N-terminus portion of the antigen. Alternately, the omitted consecutive amino acids may be from the internal portion of the antigen, thus retaining at least its C-terminus and N-terminus amino acids of the antigen.

Any Mtb antigen, including any Mtb antigen within any of the fusion proteins described herein, can have one or more amino acid additions, deletions, or substitutions compared to the particular amino acid sequences listed in Tables 1 through 8. Any individual Mtb antigen, including any Mtb antigen within any of the fusion proteins described herein, can have at least one, at least two, at least three, at least four, at least five, at least six, at least seven, at least eight, at least nine, at least ten, at least eleven, or at least twelve amino acid additions, deletions, or substitutions compared to the particular amino acid sequences listed in Tables 1 through 8. Any individual Mtb antigen, including any Mtb antigen within any of the fusion proteins described herein, can have one, two, three, four, five, six, seven, eight, nine, ten, eleven, or twelve amino acid additions, deletions, or substitutions compared to the particular amino acid sequences listed in Tables 1 through 8. The amino acid additions, deletions, or substitutions can take place at any amino acid position within the Mtb antigen.

Where a particular Mtb antigen, including any Mtb antigen within any of the fusion proteins described herein, comprises at least one or more substitutions, the substituted amino acid(s) can each be, independently, any naturally occurring amino acid or any non-naturally occurring amino acid. Thus, a particular Mtb antigen may comprise one or more amino acid substitutions that are naturally occurring amino acids and/or one or more amino acid substitutions that are non-naturally occurring amino acids. Individual amino acid substitutions are selected from any one of the following: 1) the set of amino acids with nonpolar sidechains, for example, Ala, Cys, Ile, Leu, Met, Phe, Pro, Val; 2) the set of amino acids with negatively charged side chains, for example, Asp, Glu; 3) the set of amino acids with positively charged sidechains, for example, Arg, His, Lys; and 4) the set of amino acids with uncharged polar sidechains, for example, Asn, Cys, Gln, Gly, His, Met, Phe, Ser, Thr, Trp, Tyr, to which are added Cys, Gly, Met and Phe. Substitutions of a member of one class with another member of the same class are contemplated herein. Naturally occurring amino acids include, for example, alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr), and valine (Val). Non-naturally occurring amino acids include, for example, norleucine, omithine, norvaline, homoserine, and other amino acid residue analogues such as those described in Ellman et al., Meth. Enzym., 1991, 202, 301-336. To generate such non-naturally occurring amino acid residues, the procedures of Noren et al., Science, 1989, 244, 182 and Ellman et al., supra, can be used. Briefly, these procedures involve chemically activating a suppressor tRNA with a non-naturally occurring amino acid residue followed by in vitro transcription and translation of the RNA.

The Mtb antigens, including any Mtb antigen within any of the fusion proteins described herein, which are modified as described herein retain their ability to elicit an immune response against *Mycobacterium tuberculosis*. That is, modification of a particular Mtb antigen, including any Mtb antigen within any of the fusion proteins described herein, will still allow the resultant Mtb antigen, or fusion protein comprising the same, to elicit an immune response against *Mycobacterium tuberculosis*.

The present disclosure also provides nucleic acid molecules encoding any of the fusion proteins described herein that comprise at least two Mtb antigens. The nucleic acid molecules described herein and in Tables 1 through 8 are representative. The specific sequences recited in Tables 1 through 8 are simply representative examples of nucleic acid molecules that can encode a particular Mtb antigen within a fusion protein. One skilled in the art having knowledge of the genetic code can routinely prepare and design a plethora of nucleic acid molecules encoding the same Mtb antigen. The length and nucleotide content of any particular nucleic acid molecule is dictated by the desired amino acid sequence of the encoded Mtb antigen. The nucleic acid molecule sequences shown in Tables 1 through 8 are DNA, although RNA nucleic acid molecules are also contemplated.

The present disclosure also provides vectors encoding any of the Mtb antigens, including Mtb antigens within any of the fusion proteins described herein, including any of the modified versions described herein. The vector can be capable of expressing an Mtb antigen in the cell of a mammal in a quantity effective to elicit an immune response in the mammal. The vector can be recombinant. The vector can comprise heterologous nucleic acid encoding the antigen. The vector can be a plasmid. In some embodiments, the plasmid is a DNA plasmid, such as a pVAX backbone vector. The vector can be useful for transfecting cells with nucleic acid encoding an Mtb antigen, which the transformed host cell is cultured and maintained under conditions wherein expression of the antigen takes place.

In some embodiments, coding sequences can be optimized for stability and high levels of expression. In some instances, codons are selected to reduce secondary structure formation of the RNA such as that formed due to intramolecular bonding.

In some embodiments, the vectors can comprise regulatory elements for gene expression of the coding sequences of the nucleic acid. The regulatory elements can be a promoter, an enhancer an initiation codon, a stop codon, or a polyadenylation signal. In some embodiments, the vector can comprise heterologous nucleic acid encoding an Mtb antigen and can further comprise an initiation codon, which is upstream of the antigen coding sequence, and a stop codon, which is downstream of the antigen coding sequence. The initiation and termination codon are in frame with the antigen coding sequence.

The vector can also comprise a promoter that is operably linked to the antigen coding sequence. The promoter operably linked to the Mtb antigen coding sequence can be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter, or the like. The promoter can also be a promoter from a human gene such as human actin, human myosin, human hemoglobin, human muscle creatine, or human metalothionein. The promoter can also be a tissue specific promoter, such as a muscle or skin specific promoter, natural or synthetic. Representative examples of promoters include the bacteriophage T7 promoter, bacteriophage T3 promoter, SP6 promoter, lac operator-promoter, tac promoter, mycobacterial Hsp60 promoter, SV40 late promoter, SV40 early promoter, RSV-LTR promoter, CMV IE promoter, SV40 early promoter or SV40 late promoter and the CMV IE promoter.

The vector can also comprise a polyadenylation signal, which can be downstream of the antigen coding sequence. The polyadenylation signal can be a SV40 polyadenylation signal, LTR polyadenylation signal, CMV polyadeylation signal, bovine growth hormone (bGH) polyadenylation signal, human growth hormone (hGH) polyadenylation signal, or human (3-globin polyadenylation signal. The SV40 polyadenylation signal can be a polyadenylation signal from a pCEP4 vector (Invitrogen, San Diego, Calif.).

The vector can also comprise an enhancer upstream of the consensus BoNT-A, BoNT-B, BoNT-E, and BoNT-F antigen sequences. The enhancer can be necessary for DNA expression. The enhancer can be human actin, human myosin, human hemoglobin, human muscle creatine or a viral enhancer such as one from CMV, HA, RSV or EBV. Polynucleotide function enhancers are described in U.S. Pat. Nos. 5,593,972, 5,962,428, and WO94/016737.

The vector can also comprise a mammalian origin of replication in order to maintain the vector extrachromosomally and produce multiple copies of the vector in a cell. The vector can be pVAX1, pCEP4 or pREP4 from Invitrogen (San Diego, Calif.), which can comprise the Epstein Barr virus origin of replication and nuclear antigen EBNA-1 coding region, which can produce high copy episomal replication without integration. The vector can be pVAX1 or a pVax1 variant with changes such as the variant plasmid described herein. The variant pVax1 plasmid is a 2998 basepair variant of the backbone vector plasmid pVAX1 (Invitrogen, Carlsbad Calif.). The CMV promoter is located at bases 137-724. The T7 promoter/priming site is at bases 664-683. Multiple cloning sites are at bases 696-811. Bovine GH polyadenylation signal is at bases 829-1053. The Kanamycin resistance gene is at bases 1226-2020. The pUC origin is at bases 2320-2993.

The vector can also comprise a regulatory sequence, which can be well suited for gene expression in a mammalian or human cell into which the vector is administered. The consensus coding sequence can comprise a codon, which can allow more efficient transcription of the coding sequence in the host cell.

The vector can be pSE420 (Invitrogen, San Diego, Calif.) or pET28b (EMD Millipore, Billerca, Mass.), which can be used for protein production in *Escherichia coli* (*E. coli*). The vector can also be pYES2 (Invitrogen, San Diego, Calif.), which can be used for protein production in *Saccharomyces* cerevisiae strains of yeast. The vector can also be of the MAXBAC™ complete baculovirus expression system (Invitrogen, San Diego, Calif.), which can be used for protein production in insect cells. The vector can also be pcDNA I or pcDNA3 (Invitrogen, San Diego, Calif.), which may be used for protein production in mammalian cells such as Chinese hamster ovary (CHO) cells. The vector can be expression vectors or systems to produce protein by routine techniques and readily available starting materials including Sambrook et al., Molecular Cloning and Laboratory Manual, Second Ed., Cold Spring Harbor (1989).

In some embodiments, the vector is a viral vector. Suitable viral vectors include, but are not limited to, an adenovirus vector, an adeno-associated virus vector, a poxvirus vector (such as, for example, vaccinia virus vector), a paramyxovirus vector, a fowlpox virus vector, an attenuated yellow fever vectors (such as, for example, YFV-17D), an alphavirus vector, a retrovirus vector (such as, for example, lentivirus vector), a Sendai virus vector, and cytomegalovirus (CMV) vector. Suitable adenovirus vectors include, but are not limited to, adenovirus 4, adenovirus 5, chimpanzee adenovirus 3, chimpanzee adenovirus 63, and chimpanzee adenovirus 68. A suitable vaccinia virus vector includes, but is not limited to, modified vaccinia Ankara (MVA). Suitable paramyxovirus vectors include, but are not limited to, modified parainfluenza virus (PIV2) and recombinant human parainfluenza virus (rHPIV2). Suitable CMV vectors include, but are not limited to, Rhesus Macaque CMV (RhCMV) vectors and Human CMV (HCMV) vectors. In some embodiments, the vector is present within a composition comprising a pharmaceutically acceptable carrier. One skilled in the art is readily familiar with numerous vectors, many of which are commercially available.

In some embodiments, the vector is a non-viral vector. In some embodiments, the non-viral vector is RNA, such as mRNA. In some embodiments, the mRNA is protamine-complexed mRNA, wherein the Mtb antigen or fusion protein is encoded by the mRNA, and the protamine complexes contribute a strong immunostimulatory signal. An exemplary mRNA vector platform is RNActive® (CureVac Inc).

The present disclosure also provides host cells comprising any of the nucleic acid molecules or vectors disclosed herein. The host cells can be used, for example, to express the Mtb antigens, or fragments of thereof. The Mtb antigens, or fragments thereof, can also be expressed in cells in vivo. The host cell that is transformed (for example, transfected) to produce the Mtb antigens, or fragments of thereof can be an immortalised mammalian cell line, such as those of lymphoid origin (for example, a myeloma, hybridoma, trioma or quadroma cell line). The host cell can also include normal lymphoid cells, such as B-cells, that have been immortalized by transformation with a virus (for example, the Epstein-Barr virus).

In some embodiments, the host cells include, but are not limited to: bacterial cells, such as *E. coli, Caulobacter crescentus, Streptomyces species,* and *Salmonella typhimurium*; yeast cells, such as *Saccharomyces cerevisiae, Schizosaccharomyces pombe, Pichia pastoris, Pichia methanolica*; insect cell lines, such as those from *Spodoptera frugiperda* (for example, Sf9 and Sf21 cell lines, and expresSF™ cells (Protein Sciences Corp., Meriden, Conn., USA)), *Drosophila* S2 cells, and *Trichoplusia* in High Five® Cells (Invitrogen, Carlsbad, Calif., USA); and mammalian cells, such as COS1 and COS7 cells, Chinese hamster ovary (CHO) cells, NSO myeloma cells, NIH 3T3 cells, 293 cells, Procell92S, perC6, HEPG2 cells, HeLa cells, L cells, HeLa, MDCK, HEK293, WI38, murine ES cell lines (for example, from strains 129/SV, C57/BL6, DBA-1, 129/SVJ), K562, Jurkat cells, and BW5147. Other useful mammalian cell lines are well known and readily available from the American Type Culture Collection ("ATCC") (Manassas, Va., USA) and the National Institute of General Medical Sciences (NIGMS) Human Genetic Cell Repository at the Coriell Cell Repositories (Camden, N.J., USA). In some embodiments, the cell is a recombinant BCG. These cell types are only representative and are not meant to be an exhaustive list.

Among other considerations, some of which are described above, a host cell strain may be chosen for its ability to process the expressed Mtb antigens, or fragment thereof, in the desired fashion. Post-translational modifications of the polypeptide include, but are not limited to, glycosylation, acetylation, carboxylation, phosphorylation, lipidation, and acylation, and it is an aspect of the present disclosure to provide Mtb antigens thereof with one or more of these post-translational modifications.

In some embodiments, the recombinant BCG has been genetically engineered to express a functional endosomalytic protein that is bioactive at pH values near neutrality (e.g. about pH 6-8 or about 6.5 to 7.5). The endosomalytic protein is active within Mycobacteria-containing endosomes, which typically have an internal pH near neutrality. The activity of the endosomalytic protein produced by the rBCG results in disruption of the endosome, permitting the rBCG to escape from the endosome and into the cytoplasm of the cell.

In some embodiments, the endosomalytic protein that is introduced into the rBCG by genetic engineering is Perfringolysin O (PfoA) from *Clostridium perfringens* or a mutant thereof, such as PfoA$_{G137Q}$, as described in WO 2007/058663.

In some embodiments, the Mycobacteria are attenuated, as exemplified by BCG. However, those of skill in the art will recognize that other attenuated and nonattenuated Mycobacteria exist which would also be suitable for use herein. Examples of additional types of Mycobacteria include, but are not limited to, *M. tuberculosis* strain CDC1551, *M. tuberculosis* strain Beijing, *M. tuberculosis* strain H37Ra (ATCC #:25177), *M. tuberculosis* strain H37Rv (ATCC #:25618), *M. bovis* (ATCC #:19211 and 27291), *M. fortuitum* (ATCC #:15073), *M. smegmatis* (ATCC #:12051 and 12549), *M. intracellulare* (ATCC #:35772 and 13209), *M. kansasii* (ATCC #:21982 and 35775) *M. avium* (ATCC #:19421 and 25291), *M. gallinarum* (ATCC #:19711), *M. vaccae* (ATCC #:15483 and 23024), *M. leprae* (ATCC #:), *M. marinarum* (ATCC #:11566 and 11567), and *M. microtti* (ATCC #:11152).

Examples of attenuated *Mycobacterium* strains include, but are not restricted To, *M. tuberculosis* pantothenate auxotroph strain, *M. tuberculosis* rpoV mutant strain, *M. tuberculosis* leucine auxotroph strain, BCG Danish strain (ATCC #35733), BCG Japanese strain (ATCC #35737), BCG Chicago strain (ATCC #27289), BCG Copenhagen strain (ATCC #: 27290), BCG Pasteur strain (ATCC #: 35734), BCG Glaxo strain (ATCC #: 35741), BCG Connaught strain (ATCC #35745), BCG Montreal (ATCC #35746), BCG1331 strain, BCG Tokyo strain, BCG Moreau strain, BCG-Pasteur Aeras, and BCG Moscow strain.

In some embodiments, the cell comprising the one or more vector(s) is present within a composition comprising a pharmaceutically acceptable carrier.

In some embodiments, the Mtb antigen, or fragment thereof, is labeled with a detectable marker. Detectable markers include, but are not limited to, radioactive isotopes (such as $P^{32}$ and $S^{35}$), enzymes (such as horseradish peroxidase, chloramphenicol acetyltransferase (CAT), β-galactosidase (β-gal), and the like), fluorochromes, chromophores, colloidal gold, dyes, and biotin. The labeled Mtb antigens, or fragments thereof, can be used to carry out diagnostic procedures in a variety of cell or tissue types. For imaging procedures, in vitro or in vivo, the Mtb antigens can be labeled with additional agents, such as NMR contrasting agents, X-ray contrasting agents, or quantum dots. Methods for attaching a detectable agent to polypeptides are known in the art. The Mtb antigens can also be attached to an insoluble support (such as a bead, a glass or plastic slide, or the like).

In some embodiments, the Mtb antigens, or fragment thereof, can be conjugated to a therapeutic agent including, but not limited to, radioisotopes (such as $^{111}$In or $^{90}$Y), toxins (such as tetanus toxoid or ricin), toxoids, and chemotherapeutic agents.

In some embodiments, the Mtb antigens, or fragments thereof, can be conjugated to an imaging agent. Imaging agents include, for example, a labeling moiety (such as biotin, fluorescent moieties, radioactive moieties, histidine tag or other peptide tags) for easy isolation or detection.

The present disclosure also provides compositions comprising at least two Mtb antigens or at least one Mtb fusion protein. In some embodiments, the at least two Mtb antigens are not present in a fusion protein. In some embodiments, the at least two Mtb antigens are in the form of a protein and not nucleic acid molecules encoding the Mtb antigens.

The present disclosure also provides any of the Mtb compositions described herein in which the composition comprises at least one nucleic acid molecule encoding at least one of the Mtb antigens. In some embodiments, the composition comprises one Mtb antigen in protein form and one or two nucleic acid molecules encoding two Mtb antigens. In some embodiments, the composition comprises two Mtb antigens in protein form, optionally as a fusion protein, and one nucleic acid molecule encoding one Mtb antigen. Thus, the present composition can be a mixture of a protein Mtb antigen(s) and nucleic acid molecule(s) encoding an Mtb antigen(s) to make up any of the compositions described herein.

In some embodiments, at least two Mtb antigens, or a fusion protein comprising the same, are encoded by one or more nucleic acid molecules within one or more vectors. In some embodiments, the one or more vectors is one or more viral vectors. In some embodiments, the one or more viral vectors are any one or more of an adenovirus vector, an adeno-associated virus vector, a poxvirus vector (such as, for example, vaccinia virus vector), a paramyxovirus vector, a fowlpox virus vector, an attenuated yellow fever vectors (such as, for example, YFV-17D), an alphavirus vector, a retrovirus vector (such as, for example, lentivirus vector), a Sendai virus vector, and CMV vector. In some embodiments, the adenovirus vector is adenovirus 4, adenovirus 5, chimpanzee adenovirus 3, chimpanzee adenovirus 63, or chimpanzee adenovirus 68. In some embodiments, the vaccinia virus vector is MVA. In some embodiments, the paramyxovirus vector is PIV2 or rHPIV2. In some embodiments, the CMV vector is a RhCMV vector of an HCMV vector. In some embodiments, the vector is present within a composition comprising a pharmaceutically acceptable carrier. In some embodiments, the at least two Mtb antigens are encoded by a single nucleic acid molecule within the same expression vector as a fusion protein.

In some embodiments, the one or more vectors is a non-viral vector. In some embodiments, the non-viral vector is RNA, such as mRNA. In some embodiments, the mRNA is protamine-complexed mRNA. An exemplary mRNA vector platform is RNActive® (CureVac Inc).

In some embodiments, where a rBCG is used as the vehicle to deliver the Mtb antigens, or fusion proteins, or nucleic acids and or vectors comprising or encoding the same, expression of all or part of the Dos R regulon is not up-regulated in the rBCG. In some embodiments, one or more of the following Dos R regulon antigens are not up-regulated in the rBCG: Rv1738, Rv2623, Rv2031c, Rv2032, Rv2626c, Rv2005c, Rv3127, Rv1733c, Rv1996, Rv2628c, Rv0079, Rv3130c, Rv3131, Rv1813c, Rv2006, Rv2029c, Rv2627c, Rv2030c, Rv3132c, and Rv2629. In some embodiments, the rBCG does not comprise up-regulation of: 1) one or more Mtb antigens, including "classical" Mtb antigens such as 85A,
85B and TB 10.4; and 2) at least one Mtb resuscitation antigen selected from Rv0867c, Rv1009, Rv1884c, Rv2389c, Rv2450c, Rv0288, Rv1009, Rv0685, Rv0824c, Rv1349, Rv2744c, Rv3347c, Rv1130, and Rv1169c. In some embodiments, the rBCG does not include the expression of the following combinations: classical antigens Rv1886c, Rv3804c; resuscitation antigens Rv0867c, Rv1884c, Rv2389c; and Mtb-specific antigen Rv3407. In some embodiments, the rBCG does not include the expression of the following combination: Rv3804c, Rv1886c, and Rv3407, or in addition with Rv3133c, and with the combination of Rv0867c, Rv1884c, and Rv2389c. In some embodiments, the rBCG does not include the expression of the following combination: TB10.4, Ag85B, Ag85A, and Rv3407. In some embodiments, the cell is not a rBCG.

The present disclosure also provides compositions comprising any one or more of the fusion proteins, Mtb antigens, nucleic acid molecules encoding Mtb antigens, including fusion proteins thereof, cells, and/or vectors and a pharmaceutically acceptable carrier. Compositions include, for example, pharmaceutical compositions. A pharmaceutically acceptable carrier refers to at least one component of a pharmaceutical preparation that is normally used for administration of active ingredients. As such, a carrier can contain any pharmaceutical excipient used in the art and any form of vehicle for administration. Carriers include, but are not limited to, phosphate buffered saline, physiological saline, water, citrate/sucrose/Tween formulations and emulsions such as, for example, oil/water emulsions.

The compositions can also include an active therapeutic agent and a variety of other pharmaceutically acceptable components. See Remington's Pharmaceutical Science (15th ed., Mack Publishing Company, Easton, Pa. (1980)). The desired form depends on the intended mode of administration and therapeutic application. The compositions can also include, depending on the formulation desired, pharmaceutically acceptable, non-toxic carriers or diluents, which are defined as vehicles commonly used to formulate pharmaceutical compositions for animal or human administration. The diluent is selected so as not to affect the biological activity of the combination. Examples of such diluents include, but are not limited to, distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Solid formulations of the compositions for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, without limitation, microcrystalline cellulose, corn starch, sodium starch glycolate, and alginic acid. Tablet binders that can be used include acacia, methylcellulose, sodium carboxymethylcellulose, polyvinylpyrrolidone (Povidone™) hydroxypropyl methylcellulose, sucrose, starch, and ethylcellulose. Lubricants that can be used include magnesium stearates, stearic acid, silicone fluid, talc, waxes, oils, and colloidal silica. Additional excipients include, for example, colorants, taste-masking agents, solubility aids, suspension agents, compressing agents, enteric coatings, sustained release aids, and the like.

In some embodiments, the compositions can be administered in the form of a depot injection or implant preparation, which can be formulated in such a manner as to permit a sustained release. An exemplary composition comprises any one or more of the compositions described herein formulated in aqueous buffer.

In some embodiments, liquid formulations of a pharmaceutical composition for oral administration prepared in water or other aqueous vehicles can contain various suspending agents such as methylcellulose, alginates, tragacanth, pectin, kelgin, carrageenan, acacia, polyvinylpyrrolidone, and polyvinyl alcohol. Liquid formulations of pharmaceutical compositions can also include solutions, emulsions, syrups and elixirs containing, together with the active compound(s), wetting agents, sweeteners, and coloring and flavoring agents. Various liquid and powder formulations of the pharmaceutical compositions can be prepared by conventional methods for inhalation into the lungs of the mammal to be treated.

In some embodiments, liquid formulations of a pharmaceutical composition for injection can comprise various carriers such as vegetable oils, dimethylacetamide, dimethylformamide, ethyl lactate, ethyl carbonate, isopropyl myristate, ethanol, polyols such as, for example, glycerol, propylene glycol, liquid polyethylene glycol, and the like. In some embodiments, the composition includes a citrate/sucrose/tween carrier. For intravenous injections, water soluble versions of the compositions can be administered by the drip method, whereby a pharmaceutical formulation containing the antifungal agent and a physiologically acceptable excipient is infused. Physiologically acceptable excipients can include, for example, 5% dextrose, 0.9% saline, Ringer's solution or other suitable excipients. A suitable insoluble form of the composition can be prepared and administered as a suspension in an aqueous base or a pharmaceutically acceptable oil base, such as an ester of a long chain fatty acid such as, for example, ethyl oleate.

The compositions can be, for example, injectable solutions, aqueous suspensions or solutions, non-aqueous suspensions or solutions, solid and liquid oral formulations, salves, gels, ointments, intradermal patches, creams, aerosols, lotions, tablets, capsules, sustained release formulations, and the like. In some embodiments, for topical applications, the pharmaceutical compositions can be formulated in a suitable ointment. In some embodiments, a topical semi-solid ointment formulation typically comprises a concentration of the active ingredient from about 1 to 20%, or from 5 to 10%, in a carrier, such as a pharmaceutical cream base. Some examples of formulations of a composition for topical use include, but are not limited to, drops, tinctures, lotions, creams, solutions, and ointments containing the active ingredient and various supports and vehicles.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or microparticles such as polylactide, polyglycolide, or copolymer for enhanced adjuvant effect (see Langer, Science, 1990, 249, 1527 and Hanes, Advanced Drug Delivery Reviews, 1997, 28, 97). A sterile injectable preparation such as, for example, a sterile injectable aqueous or oleaginous suspension can also be prepared. This suspension may be formulated according to techniques known in the art using suitable dispersing, wetting, and suspending agents. In some embodiments, the pharmaceutical composition can be delivered in a microencapsulation device so as to reduce or prevent a host immune response against the protein.

In some embodiments, any of the Mtb antigens, constructs, vectors, or cells described herein, or compositions comprising the same, can be combined into a single therapeutic or prophylactic regimen. For example, in some embodiments, an antigen matched BCG can be combined or used with a recombinant protein vaccine.

In some embodiments, any of the Mtb antigens, constructs, vectors, or cells described herein, or compositions comprising the same, can be administered to a mammal as an aerosol. In some embodiments, the aerosol inocula comprises saline. Conventional aerosol delivery devices include, but are not limited to, a pressurized metered dose inhaler (pMDI) and a dry power inhaler (DPI), both of which deliver a dry powder formulation, and nebulizers such as the PARI eFlow device, which delivers an aqueous dose as a fine mist. In some embodiments, the aerosol delivery device is a Pari eFlow portable electronic aerosol delivery platform attached to a delivery mask. In some embodiments, the average particle size is from about 1 μm to about 10 μm, from about 1 μm to about 5 μm, from about 3 μm to about 5 μm, from about 4 μm to about 5 μm, or from about 3.9 μm to about 4.9 μm. In some embodiments, the aerosol is in a volume from about 0.1 ml to about 5 ml, from about 0.1 ml to about 2 ml, from about 0.1 ml to about 1.5 ml, from about 0.5 ml to about 1.5 ml, from about 0.5 ml to about 1.2 ml, from about 0.7 ml to about 1.2 ml, or about 1 ml.

Effective doses of the compositions of the present disclosure, for the treatment of a condition vary depending upon many different factors, including means of administration, target site, physiological state of the subject, whether the subject is human or an animal, other medications administered, and whether treatment is prophylactic or therapeutic. Usually, the subject is a human but non-human mammals including transgenic mammals can also be treated.

In some embodiments, the compositions can be administered to a subject by injection intravenously, subcutaneously, intraperitoneally, intramuscularly, intramedullarily, intraventricularly, intraepidurally, intraarterially, intravascularly, intraarticularly, intrasynovially, intrasternally, intrathecally, intrahepatically, intraspinally, intratumorly, intracranially, enteral, intrapulmonary, transmucosal, intrauterine, sublingual, or locally at sites of inflammation or tumor growth by using standard methods. In some embodiments, the compositions can be administered to a subject by injection intravenously. Alternately, the compositions can be administered to a subject by routes including oral, nasal, ophthalmic, rectal, or topical. The most typical route of administration is intravascular, subcutaneous, or intramuscular, although other routes can be effective. In some embodiments, compositions are administered as a sustained release composition or device, such as a Medipad™ device. The composition can also be administered via the respiratory tract, for example, using a dry powder inhalation device, nebulizer, or a metered dose inhaler. The composition can also be administered by traditional syringes, needleless injection devices, "microprojectile bombardment gone guns," or other physical methods such as electroporation ("EP"), "hydrodynamic method", or ultrasound.

In some embodiments, the composition can be administered to a subject by sustained release administration, by such means as depot injections of erodible implants directly applied during surgery or by implantation of an infusion pump or a biocompatible sustained release implant into the subject. Alternately, the composition can be administered to a subject by injectable depot routes of administration, such as by using 1-, 3-, or 6-month depot injectable or biodegradable materials and methods, or by applying to the skin of the subject a transdermal patch containing the composition, and leaving the patch in contact with the subject's skin, generally for 1 to 5 hours per patch.

In some embodiments, the compositions comprise about 1 nanogram to about 10 mg of nucleic acid. In some embodiments, the compositions comprise: 1) at least 10, 15, 20, 25, 30, 35, 40, 45, 50, 55, 60, 65, 70, 75, 80, 85, 90, 95 or 100 nanograms, or at least 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995 or 1000 micrograms, or at least 1.5, 2, 2.5, 3, 3.5, 4, 4.5, 5, 5.5, 6, 6.5, 7, 7.5, 8, 8.5, 9, 9.5 or 10 mg or more; and 2) up to and including 15, 20, 25, 30, 35, 40, 45, 50, 55, 60, 65, 70, 75, 80, 85, 90, 95 or 100 nanograms, or up to and including 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, or 1000 micrograms, or up to and including 1.5, 2, 2.5, 3, 3.5, 4, 4.5, 5, 5.5, 6, 6.5, 7, 7.5, 8, 8.5, 9, 9.5 or 10 mg.

In some embodiments, the compositions comprise about 5 ng to about 10 mg of nucleic acid molecule. In some embodiments, the compositions comprise about 25 ng to about 5 mg of nucleic acid molecule. In some embodiments, the compositions contain about 50 ng to about 1 mg of nucleic acid molecule. In some embodiments, the compositions contain about 0.1 to about 500 μg of nucleic acid molecule. In some embodiments, the compositions contain about 1 μg to about 350 μg of nucleic acid molecule. In some embodiments, the compositions contain about 5 μg to about 250 μg of nucleic acid molecule. In some embodiments, the compositions contain about 10 μg to about 200 μg of nucleic acid molecule. In some embodiments, the compositions contain about 15 μg to about 150 μg of nucleic acid molecule. In some embodiments, the compositions contain about 20 μg to about 100 μg of nucleic acid molecule. In some embodiments, the compositions contain about 25 μg to about 75 μg of nucleic acid molecule. In some embodiments, the compositions contain about 30 μg to about 50 μg of nucleic acid molecule. In some embodiments, the compositions contain about 35 μg to about 40 μg of nucleic acid molecule. In some embodiments, the compositions contain about 100 μg to about 200 μg of nucleic acid molecule. In some embodiments, the compositions comprise about 10 μg to about 100 μg of nucleic acid molecule. In some embodiments, the compositions comprise about 20 μg to about 80 μg of nucleic acid molecule. In some embodiments, the compositions comprise about 25 μg to about 60 μg of nucleic acid molecule. In some embodiments, the compositions comprise about 30 ng to about 50 μg of nucleic acid molecule. In some embodiments, the compositions comprise about 35 ng to about 45 μg of nucleic acid molecule. In some embodiments, the compositions contain about 0.1 μg to about 500 μg of nucleic acid molecule. In some embodiments, the compositions contain about 1 μg to about 350 μg of nucleic acid molecule. In some embodiments, the compositions contain about 25 μg to about 250 μg of nucleic acid molecule. In some embodiments, the compositions contain about 100 μg to about 200 μg of nucleic acid molecule.

In some embodiments, the delivery platforms described herein can be used either in a single administration alone or in combinations as matched antigen prime-boost approaches. In addition, the use of these antigens in a single vector system, which is envisioned to be used as an antigen matched prime for a boost with any of the modalities above, including protein, viral vectors, nucleic acids, or others. For example, the same Mtb antigen construct can be used as both the prime and the boost. In other embodiments, a first Mtb antigen construct can be used as the prime and a second different Mtb antigen construct can be used as the boost (i.e., heterologous prime-boost). In some embodiments, the prime is a DNA or RNA (such as mRNA) prime and the boost is a viral vector boost. In some embodiments, the prime is a viral vector prime and the boost is a DNA or RNA (such as mRNA) boost.

The compositions can be formulated according to the mode of administration to be used. In cases where compositions are injectable pharmaceutical compositions, they are sterile, pyrogen free and particulate free. An isotonic formulation can be used. Generally, additives for isotonicity can include sodium chloride, dextrose, mannitol, sorbitol and lactose. In some cases, isotonic solutions such as phosphate buffered saline are suitable. Stabilizers include gelatin and albumin. In some embodiments, a vasoconstriction agent is added to the formulation.

The compositions can further comprise a pharmaceutically acceptable excipient. The pharmaceutically acceptable excipient can be functional molecules as vehicles, adjuvants, carriers, or diluents. The pharmaceutically acceptable excipient can be a transfection facilitating agent, which can include surface active agents, such as immune-stimulating complexes (ISCOMS), Freund's incomplete adjuvant, LPS analog including monophosphoryl lipid A, muramyl peptides, quinone analogs, vesicles such as squalene and squalane, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more suitably, the poly-L-glutamate is present in the composition at a concentration less than 6 mg/ml. The transfection facilitating agent can also include surface active agents such as immune-stimulating complexes (ISCOMS), Freunds incomplete adjuvant, LPS analog including monophosphoryl lipid A, muramyl peptides, quinone analogs and vesicles such as squalene and squalane, and hyaluronic acid can also be used administered in conjunction with the genetic construct. In some embodiments, the plasmid compositions can also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. In some embodiments, the transfection facilitating agent is a polyanion, polycation, including poly-L-glutamate (LGS), or lipid. Concentration of the transfection agent in the composition is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient may be an adjuvant. The adjuvant may be other genes that are expressed in alternative plasmid or are delivered as proteins in combination with the plasmid above. The adjuvant may be selected from the group consisting of: α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. The adjuvant may be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof.

Other genes which may be useful adjuvants include those encoding: MCP-1, MIP-1a, MIP-1p, IL-8, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, 1 kB, Inactive NIK, SAP K, SAP-1, JNK, interferon response genes, NFkB, Bax, TRAIL, TRAILrec, TRAIL-recDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The present disclosure also provides kits comprising any of the Mtb antigens, fragments thereof, fusion proteins, nucleic acid molecules, vectors, or cells, described herein. The kit can include, for example, container(s), package(s) or dispenser(s) along with labels and instructions for administration or use.

The present disclosure also provides methods of eliciting an immune response against *Mycobacterium tuberculosis* in a mammal comprising administering to the mammal an immunologically sufficient amount of one or more fusion proteins described herein. Any of the fusion proteins described herein can be administered. In some embodiments, the fusion protein comprises Rv3872-Rv1788-Rv3893c-Rv0285-Rv1818c-Rv0159c-Rv1172c (Construct A; see Table 2). In some embodiments, the fusion protein comprises Rv3873-Rv1387-Rv3892c (Construct B; see Table 4). In some embodiments, the fusion protein comprises Rv1789-Rv1800-Rv1039c (Construct C; see Table 4). In some embodiments, the fusion protein comprises Rv3017c-Rv3020c-Rv3019c-Rv3891c-Rv2346c-Rv3445c (Construct D; see Table 6). In some embodiments, the fusion protein comprises Rv3619c-Rv3875-Rv3874 (Construct E; see Table 6). In some embodiments, the fusion protein comprises Rv2719c-Rv0010c-Rv1872c (Construct F; see Table 8). In some embodiments, the fusion protein comprises Rv0012-Rv0990c-Rv0995 (Construct G; see Table 8).

The present disclosure also provides methods of eliciting an immune response against *Mycobacterium tuberculosis* in a mammal comprising administering to the mammal an immunologically sufficient amount of any of the Mtb compositions described herein. Any of the compositions comprising two or more Mtb antigens can be administered. In some embodiments, the composition comprises Rv3872, Rv1788, Rv3893c, Rv0285, Rv1818c, Rv0159c, and Rv1172c. In some embodiments, the composition comprises Rv3873, Rv1387, and Rv3892c. In some embodiments, the composition comprises Rv1789, Rv1800, and Rv1039c. In some embodiments, the composition comprises Rv3017c, Rv3020c, Rv3019c, Rv3891c, Rv2346c, and Rv3445c. In some embodiments, the composition comprises Rv3619c, Rv3875, and Rv3874. In some embodiments, the composition comprises Rv2719c, Rv0010c, and Rv1872c. In some embodiments, the composition comprises Rv0012, Rv0990c, and Rv0995.

The present disclosure also provides methods of eliciting an immune response against *Mycobacterium tuberculosis* in a mammal comprising administering to the mammal an immunologically sufficient amount of a composition comprising at least two or three Mtb antigens, and a pharmaceutically acceptable carrier; wherein the composition comprises at least one nucleic acid molecule encoding at least one of the Mtb antigens. Any of the compositions comprising a mixture of one or more Mtb antigen proteins and one of more nucleic acid molecules encoding one or more Mtb antigens described herein can be administered.

The fusion proteins and compositions described herein can be used to treat or prevent tuberculosis. In some embodiments, the method comprises administering to a human a therapeutically- or prophylactically-effective amount of any of the fusion proteins or compositions described herein such that the tuberculosis infection is diminished or prevented.

In some embodiments, the subject being treated will have been previously diagnosed as having tuberculosis. Such subjects will, thus, have been diagnosed as being in need of such treatment. Alternately, the treatment may be intended to prevent a tuberculosis infection in a subject that does not yet have tuberculosis or to a subject that is travelling to an area where tuberculosis is prevalent.

Treatment of a subject suffering from tuberculosis can be monitored using standard methods. Some methods entail determining a baseline value, for example, of an antibody level or profile in a subject, before administering a dosage of agent, and comparing this with a value for the profile or level after treatment. A significant increase such as, for example, greater than the typical margin of experimental error in repeat measurements of the same sample, expressed as one standard deviation from the mean of such measurements in value of the level or profile signals a positive treatment outcome (i.e., that administration of the agent has achieved a desired response). If the value for immune response does not change significantly, or decreases, a negative treatment outcome is indicated.

In some embodiments, a control value such as a mean and standard deviation, of level or profile is determined for a control population. Typically the individuals in the control population have not received prior treatment. Measured values of the level or profile in a subject after administering a therapeutic agent are then compared with the control value. A significant increase relative to the control value, such as greater than one standard deviation from the mean, signals a positive or sufficient treatment outcome. A lack of significant increase or a decrease signals a negative or insufficient treatment outcome. Administration of the therapeutic is generally continued while the level is increasing relative to the control value. As before, attainment of a plateau relative to control values is an indicator that the administration of treatment can be discontinued or reduced in dosage and/or frequency.

In other embodiments, a control value of the level or profile, such as a mean and standard deviation, is determined from a control population of individuals who have undergone treatment with a therapeutic agent and whose levels or profiles have plateaued in response to treatment. Measured values of levels or profiles in a subject are compared with the control value. If the measured level in a subject is not significantly different, such as by more than one standard deviation, from the control value, treatment can be discontinued. If the level in a subject is significantly below the control value, continued administration of agent is warranted. If the level in the subject persists below the control value, then a change in treatment may be indicated.

In some embodiments, a subject who is not presently receiving treatment but has undergone a previous course of treatment is monitored for antibody levels or profiles to determine whether a resumption of treatment is required. The measured level or profile in the subject can be compared with a value previously achieved in the subject after a previous course of treatment. A significant decrease relative to the previous measurement, such as greater than a typical margin of error in repeat measurements of the same sample, is an indication that treatment can be resumed. Alternately, the value measured in a subject can be compared with a control value (mean plus standard deviation) determined in a population of subjects after undergoing a course of treatment. Alternately, the measured value in a subject can be compared with a control value in populations of prophylactically treated subjects who remain free of symptoms of disease, or populations of therapeutically treated subjects who show amelioration of disease characteristics. In all of these cases, a significant decrease relative to the control level, such as more than a standard deviation, is an indicator that treatment should be resumed in a subject.

In some methods, a baseline measurement of antibody to a given antigen in the subject is made before administration, a second measurement is made soon thereafter to determine the peak antibody level, and one or more further measurements are made at intervals to monitor decay of antibody levels. When the level of antibody has declined to baseline or a predetermined percentage of the peak less baseline, such as 50%, 25% or 10%, administration of a further dosage of antigen is administered. In some embodiments, peak or subsequent measured levels less background are compared with reference levels previously determined to constitute a beneficial prophylactic or therapeutic treatment regime in other subjects. If the measured antibody level is significantly less than a reference level, such as less than the mean minus one standard deviation of the reference value in population of subjects benefiting from treatment, administration of an additional dosage of antigen is indicated.

In some embodiments, the subject(s) that can be treated by the above-described methods is an animal, including mammals and non-mammals. Suitable mammals, include, but are not limited to, humans, non-human primates, rodents (including rats, mice, hamsters and guinea pigs) cow, horse, sheep, badger, opossum, goat, pig, dog and cat. In most instances, the mammal is a human. In some embodiments, the non-mammal is a fish Immunization of animals with any one or more of the vaccines described herein can prevent zoonotic transmission (i.e., transition of a disease, such as TB, from an animal to a human).

The present disclosure also provides fusion proteins for use in the preparation of a medicament for treating or preventing a *Mycobacterium tuberculosis* infection. Any of the fusion proteins described herein can be administered. In some embodiments, the fusion protein comprises Rv3872-Rv1788-Rv3893c-Rv0285-Rv1818c-Rv0159c-Rv1172c (Construct A; see Table 2). In some embodiments, the fusion protein comprises Rv3873-Rv1387-Rv3892c (Construct B; see Table 4). In some embodiments, the fusion protein comprises Rv1789-Rv1800-Rv1039c (Construct C; see Table 4). In some embodiments, the fusion protein comprises Rv3017c-Rv3020c-Rv3019c-Rv3891c-Rv2346c-Rv3445c (Construct D; see Table 6). In some embodiments, the fusion protein comprises Rv3619c-Rv3875-Rv3874 (Construct E; see Table 6). In some embodiments, the fusion protein comprises Rv2719c-Rv0010c-Rv1872c (Construct F; see Table 8). In some embodiments, the fusion protein comprises Rv0012-Rv0990c-Rv0995 (Construct G; see Table 8).

The present disclosure also provides fusion proteins for use in treating or preventing a *Mycobacterium tuberculosis* infection. Any of the fusion proteins described herein can be administered. In some embodiments, the fusion protein comprises Rv3872-Rv1788-Rv3893c-Rv0285-Rv1818c-Rv0159c-Rv1172c (Construct A; see Table 2). In some embodiments, the fusion protein comprises Rv3873-Rv1387-Rv3892c (Construct B; see Table 4). In some embodiments, the fusion protein comprises Rv1789-Rv1800-Rv1039c (Construct C; see Table 4). In some embodiments, the fusion protein comprises Rv3017c-Rv3020c-Rv3019c-Rv3891c-Rv2346c-Rv3445c (Construct D; see Table 6). In some embodiments, the fusion protein comprises Rv3619c-Rv3875-Rv3874 (Construct E; see Table 6). In some embodiments, the fusion protein comprises Rv2719c-Rv0010c-Rv1872c (Construct F; see Table 8). In some embodiments, the fusion protein comprises Rv0012-Rv0990c-Rv0995 (Construct G; see Table 8).

The present disclosure also provides use of a fusion protein in the preparation of a medicament for treating or preventing a *Mycobacterium tuberculosis* infection. Any of the fusion proteins described herein can be administered. In some embodiments, the fusion protein comprises Rv3872-Rv1788-Rv3893c-Rv0285-Rv1818c-Rv0159c-Rv1172c (Construct A; see Table 2). In some embodiments, the fusion protein comprises Rv3873-Rv1387-Rv3892c (Construct B; see Table 4). In some embodiments, the fusion protein comprises Rv1789-Rv1800-Rv1039c (Construct C; see Table 4). In some embodiments, the fusion protein comprises Rv3017c-Rv3020c-Rv3019c-Rv3891c-Rv2346c-

Rv3445c (Construct D; see Table 6). In some embodiments, the fusion protein comprises Rv3619c-Rv3875-Rv3874 (Construct E; see Table 6). In some embodiments, the fusion protein comprises Rv2719c-Rv0010c-Rv1872c (Construct F; see Table 8). In some embodiments, the fusion protein comprises Rv0012-Rv0990c-Rv0995 (Construct G; see Table 8).

The present disclosure also provides uses of a fusion protein in treating or preventing a *Mycobacterium tuberculosis* infection. Any of the fusion proteins described herein can be administered. In some embodiments, the fusion protein comprises Rv3872-Rv1788-Rv3893c-Rv0285-Rv1818c-Rv0159c-Rv1172c (Construct A; see Table 2). In some embodiments, the fusion protein comprises Rv3873-Rv1387-Rv3892c (Construct B; see Table 4). In some embodiments, the fusion protein comprises Rv1789-Rv1800-Rv1039c (Construct C; see Table 4). In some embodiments, the fusion protein comprises Rv3017c-Rv3020c-Rv3019c-Rv3891c-Rv2346c-Rv3445c (Construct D; see Table 6). In some embodiments, the fusion protein comprises Rv3619c-Rv3875-Rv3874 (Construct E; see Table 6). In some embodiments, the fusion protein comprises Rv2719c-Rv0010c-Rv1872c (Construct F; see Table 8). In some embodiments, the fusion protein comprises Rv0012-Rv0990c-Rv0995 (Construct G; see Table 8).

The present disclosure also provides compositions for use in the preparation of a medicament for treating or preventing a *Mycobacterium tuberculosis* infection. Any of the compositions comprising two or more Mtb antigens can be administered. In some embodiments, the composition comprises Rv3872, Rv1788, Rv3893c, Rv0285, Rv1818c, Rv0159c, and Rv1172c. In some embodiments, the composition comprises Rv3873, Rv1387, and Rv3892c. In some embodiments, the composition comprises Rv1789, Rv1800, and Rv1039c. In some embodiments, the composition comprises Rv3017c, Rv3020c, Rv3019c, Rv3891c, Rv2346c, and Rv3445c. In some embodiments, the composition comprises Rv3619c, Rv3875, and Rv3874. In some embodiments, the composition comprises Rv2719c, Rv0010c, and Rv1872c. In some embodiments, the composition comprises Rv0012, Rv0990c, and Rv0995.

The present disclosure also provides compositions for use in treating or preventing a *Mycobacterium tuberculosis* infection. Any of the compositions comprising two or more Mtb antigens can be administered. In some embodiments, the composition comprises Rv3872, Rv1788, Rv3893c, Rv0285, Rv1818c, Rv0159c, and Rv1172c. In some embodiments, the composition comprises Rv3873, Rv1387, and Rv3892c. In some embodiments, the composition comprises Rv1789, Rv1800, and Rv1039c. In some embodiments, the composition comprises Rv3017c, Rv3020c, Rv3019c, Rv3891c, Rv2346c, and Rv3445c. In some embodiments, the composition comprises Rv3619c, Rv3875, and Rv3874. In some embodiments, the composition comprises Rv2719c, Rv0010c, and Rv1872c. In some embodiments, the composition comprises Rv0012, Rv0990c, and Rv0995.

The present disclosure also provides uses of a composition in treating or preventing a *Mycobacterium tuberculosis* infection. Any of the compositions comprising two or more Mtb antigens can be administered. In some embodiments, the composition comprises Rv3872, Rv1788, Rv3893c, Rv0285, Rv1818c, Rv0159c, and Rv1172c. In some embodiments, the composition comprises Rv3873, Rv1387, and Rv3892c. In some embodiments, the composition comprises Rv1789, Rv1800, and Rv1039c. In some embodiments, the composition comprises Rv3017c, Rv3020c, Rv3019c, Rv3891c, Rv2346c, and Rv3445c. In some embodiments, the composition comprises Rv3619c, Rv3875, and Rv3874. In some embodiments, the composition comprises Rv2719c, Rv0010c, and Rv1872c. In some embodiments, the composition comprises Rv0012, Rv0990c, and Rv0995.

The present disclosure also provides compositions for use in the preparation of a medicament for treating or preventing a *Mycobacterium tuberculosis* infection, wherein the composition comprises at least two or three Mtb antigens, and a pharmaceutically acceptable carrier, wherein the composition comprises at least one nucleic acid molecule encoding at least one of the Mtb antigens.

The present disclosure also provides compositions for use in treating or preventing a *Mycobacterium tuberculosis* infection, wherein the composition comprises at least two or three Mtb antigens, and a pharmaceutically acceptable carrier, wherein the composition comprises at least one nucleic acid molecule encoding at least one of the Mtb antigens.

The present disclosure also provides uses of a composition in the preparation of a medicament for treating or preventing a *Mycobacterium tuberculosis* infection, wherein the composition comprises at least two or three Mtb antigens, and a pharmaceutically acceptable carrier, wherein the composition comprises at least one nucleic acid molecule encoding at least one of the Mtb antigens.

The present disclosure also provides uses of a composition in treating or preventing a *Mycobacterium tuberculosis* infection, wherein the composition comprises at least two or three Mtb antigens, and a pharmaceutically acceptable carrier, wherein the composition comprises at least one nucleic acid molecule encoding at least one of the Mtb antigens.

The present disclosure also provides any of the fusion proteins described herein, or any of the compositions described herein, or any of the cells described herein, or any of the vectors described herein, or any of the methods described herein, or any of the uses described herein, substantially as described herein.

Various modifications of the described subject matter, in addition to those described herein, will be apparent to those skilled in the art from the foregoing description. Such modifications are also intended to fall within the scope of the appended claims Each reference (including, but not limited to, journal articles, U.S. and non-U.S. patents, patent application publications, international patent application publications, gene bank accession numbers, and the like) cited in the present application is incorporated herein by reference in its entirety.

What is claimed is:

1. A fusion protein comprising at least three Mtb PPE antigens chosen from Rv3873, Rv1387, Rv3892c, Rv1789, Rv1800, and Rv1039c, wherein: Rv3873 comprises the amino acid sequence set forth in SEQ ID NO:19, Rv1387 comprises the amino acid sequence set forth in SEQ ID NO:21, Rv3892c comprises the amino acid sequence set forth in SEQ ID NO:23, Rv1789 comprises the amino acid sequence set forth in SEQ ID NO:25, Rv1800 comprises the amino acid sequence set forth in SEQ ID NO:27, and/or Rv1039c comprises the amino acid sequence set forth in SEQ ID NO:29.

2. The fusion protein according to claim 1 comprising: Rv3873, Rv1387, and Rv3892c; or Rv1789, Rv1800, and Rv1039c.

3. The fusion protein according to claim 1 comprising Rv3873-Rv1387-Rv3892c.

4. A pharmaceutical composition comprising the fusion protein according to claim 1 and a pharmaceutically acceptable carrier.

5. A fusion protein comprising at least two Mtb PPE antigens chosen from Rv3873, Rv1387, Rv3892c, Rv1789, Rv1800, and Rv1039c, wherein: Rv3873 comprises the amino acid sequence set forth in SEQ ID NO:19, Rv1387 comprises the amino acid sequence set forth in SEQ ID NO:21, Rv3892c comprises the amino acid sequence set forth in SEQ ID NO:23, Rv1789 comprises the amino acid sequence set forth in SEQ ID NO:25, Rv1800 comprises the amino acid sequence set forth in SEQ ID NO:27, and/or Rv1039c comprises the amino acid sequence set forth in SEQ ID NO:29, wherein when the fusion protein comprises Rv3873, the fusion protein does not comprise Rv1789, and wherein when the fusion protein comprises Rv1789, the fusion protein does not comprise Rv3873.

6. A fusion protein comprising at least two Mtb PPE antigens chosen from an Rv3873 fragment, Rv1387, Rv3892c, an Rv1789 fragment, Rv1800, and Rv1039c, wherein: the Rv3873 fragment comprises the amino acid sequence set forth in SEQ ID NO:19, Rv1387 comprises the amino acid sequence set forth in SEQ ID NO:21, Rv3892c comprises the amino acid sequence set forth in SEQ ID NO:23, the Rv1789 fragment comprises the amino acid sequence set forth in SEQ ID NO:25, Rv1800 comprises the amino acid sequence set forth in SEQ ID NO:27, and/or Rv1039c comprises the amino acid sequence set forth in SEQ ID NO:29 NO:29, and when the fusion protein comprises an Rv3873 fragment, the fusion protein does not comprise an Rv1789 fragment, and wherein when the fusion protein comprises an Rv1789 fragment, the fusion protein does not comprise an Rv3873 fragment.

\* \* \* \* \*